US008114857B2

(12) United States Patent
Wallace et al.

(10) Patent No.: US 8,114,857 B2
(45) Date of Patent: Feb. 14, 2012

(54) DERIVATIVES OF 4- OR 5-AMINOSALICYLIC ACID

(75) Inventors: John L. Wallace, Ancaster (CA);
Giuseppe Cirino, Naples (IT);
Giuseppe Caliendo, Napoli (IT); Anna Sparatore, Milan (IT); Vicenzo Santagada, Cosenza (IT); Stefano Fiorucci, Perugia (IT)

(73) Assignee: Antibe Therapeutics Inc., Calgary (CA)

( * ) Notice: Subject to any disclaimer, the term of this patent is extended or adjusted under 35 U.S.C. 154(b) by 0 days.

(21) Appl. No.: 12/980,985

(22) Filed: Dec. 29, 2010

(65) Prior Publication Data

US 2011/0130368 A1    Jun. 2, 2011

Related U.S. Application Data

(60) Division of application No. 12/368,846, filed on Feb. 10, 2009, now Pat. No. 7,879,827, which is a continuation of application No. 11/278,395, filed on Mar. 31, 2006, now Pat. No. 7,498,355, which is a continuation-in-part of application No. 11/139,871, filed on May 27, 2005, now abandoned.

(51) Int. Cl.
*A61K 31/655* (2006.01)
*A61K 31/60* (2006.01)
*C07C 241/00* (2006.01)
*C07C 229/00* (2006.01)

(52) U.S. Cl. ......... 514/150; 514/159; 562/439; 562/453

(58) Field of Classification Search ................... 514/150, 514/159; 562/439, 453
See application file for complete search history.

(56) References Cited

U.S. PATENT DOCUMENTS

| | | | |
|---|---|---|---|
| 4,412,992 | A | 11/1983 | Chan et al. |
| 4,440,763 | A | 4/1984 | Lover |
| 5,013,727 | A | 5/1991 | Halskov |
| 6,197,341 | B1 | 3/2001 | Friess et al. |
| 6,458,776 | B1 | 10/2002 | Ekwuribe et al. |
| 6,602,915 | B2 | 8/2003 | Uhrich et al. |

FOREIGN PATENT DOCUMENTS

| | | |
|---|---|---|
| CA | 2204747 | 3/1997 |
| WO | WO 2005/072113 | 8/2005 |
| WO | WO 2006/037623 | 4/2006 |
| WO | WO 2006/066894 | 6/2006 |

OTHER PUBLICATIONS

Golub et al. Science (1999), vol. 286 531-537.*
Lala et al. Cancer and Metastasis Reviews (1998), 17(1), 91-106.*
Galvez, Julio, et al., "Intestinal anti-inflammatory activity of UR-12746, a novel 5-ASA conjugate, on acute and chronic experimental colitis in the rat", British Journal of Pharmacology, 2000, vol. 130, No. 8, pp. 1949 through 1959.

Wahl, Christian, et al., "Sulfasalazine: a Potent and Specific Inhibitor of Nuclear Factor Kappa B", The American Society for Clinical Investigation, Inc., vol. 101, No. 5, Mar. 1998, pp. 1163 through 1174.
Bai, Ai-Ping, et al., "Diallyl Trisulfide Inhibits Tumor Necrosis Factor-α Expression in Inflammed Mucosa of Ulcerative Colitis", Digestive Diseases and Sciences, vol. 50, No. 8, Aug. 2005, pp. 1426 through 1431.
Li, Ling, et al., "Hydrogen sulphide—a novel mediator of inflammation?", Current Opinion in Pharmacology 2006, No. 6, pp. 125 through 129.
Ohge, Hiroki, et al., "Association Between Fecal Hydrogen Sulfide Production and Pouchitis", Dis Colon Rectum, Mar. 2005, vol. 48, No. 3, pp. 469 through 475.
Schmedes, Anne, et al., "Low S-adenosylmethionine concentrations found in patients with sever inflammatory bowel disease", Clin Chem Lab Med, 2004, vol. 42, No. 6, pp. 648 through 653.
Wang, Rui, "Two's company, three's a crowd: can H2S be the third endogenous gaseous transmitter?", the FASEB Journal, vol. 16, Nov. 2002, pp. 1792 through 1798.
Aharonowitz et al. Journal of Bacteriology, vol. 175, 1993, p. 623-629.
Google search results under term "hydrogen sulfide relseasing moiety" (in part).
Pellicciari, et al., "Brush-Border-Enzyme-Mediated Intestine-Specific Drug Delivery, Amino Acid Prodrugs of 5-Aminosalicylic Acid", J. Med. Chem, 1993, vol. 36, pp. 4201-4207.
Distrutti, et al., "Evidence That Hydrogen Sulfide Exerts Antinocicieptive Effects in the Gastrointestinal Tract by Activating KATP Channels", J. Pharm. and Exp. Ther., 2005, vol. 316, pp. 325-335.
Teague, et al., "The Smooth Muscle Relaxant Effect of Hydrogen Sulfide in Vitro: Evidence for a Physiological Role to Control Intestinal Contractility", Br. J. Pharmacol, vol. 137, pp. 139-145, 2002.
Dzierzewicz, et al., "Susceptibility of Desulfovibrio desulfuuricans intestinal strains to sulfasalazine and its biotransformation products", Med. Sci. Monit., 2004, vol. 10, No. 6, BR185-190. Edmond, et al., "The effect of 5-aminosalicylic acid-containing drugs on sulfide production by sulfate-reducing bacteria and amino acid-fermenting bacteria", Inflammatory Bowel Diseases, 2003, vol. 9, No. 1, pp. 10-17.
Fiorucci, et al., :Inhibition of Hydrogen Sulfide Generation Contributes to Gastric Injury Caused by Anti-Inflammmatory Nonsteroidal Drugs, Gastroenterology, Oct. 2005, vol. 129, No. 4, pp. 1210-1224.
Sidhu, et al., "L-Cysteine and Sodium Hydrogensulfide Inhibit Spontaneous Contractibility in Isolaged Pregnant Rat Uterine Strips in Vivo", Pharmacology & Toxicology, 2001, vol. 88, pp. 198-203.
Zhao, et al., "The vasorelaxant effect of H2S as a novel endogenous gaseous KATP channel opener", EMBO Journal, 2001, vol. 2, No. 21, pp. 6008-6016.

(Continued)

*Primary Examiner* — Rebecca Anderson
*Assistant Examiner* — Samantha Shterengarts
(74) *Attorney, Agent, or Firm* — Bennett Jones LLP

(57) ABSTRACT

The present invention provides new derivatives of 4- or 5-aminosalicylic acid, and a pharmaceutical composition containing these derivatives of 4- or 5-aminosalicylic acid as active ingredients, useful for the treatment of intestinal diseases such as inflammatory bowel disease (IBD) and irritable bowel syndrome (IBS) and for the prevention/treatment of colon cancer. More particularly, these derivatives comprise a hydrogen sulfide releasing moiety linked via an azo, an ester, an anhydride, a thioester or an amide linkage to a molecule of 4- or 5-aminosalicylic acid. Furthermore, the present invention provides a process for preparing these compounds and their use for treating IBD and IBS and the prevention/treatment of colon cancer.

5 Claims, 22 Drawing Sheets

OTHER PUBLICATIONS

Zhao, et al., "H2S-Induced vasolrelaxation and underlying cellular and molecular mechanisms", Am. J. Physiol. Heart Circ. Physiol., 2002, vol. 283: H474-480.

Abe, et al., "The possible role of hydrogen sulfide as an endogenous neuromodulator", The Journal of Neuroscience, 1996, vol. 16, No. 3, pp. 1066-1071.

Carceller, et al., "Novel Azo derivatives as prodrugs of 5-aminosalicylic acid and amino derivatives with potent platelet activating factor antagonist activity", J. Med. Chem., 2001, vol. 44, No. 18, pp. 3001-3013.

M C L Pitcher, et al., "The contribution of sulphate reducing bacteria and 5-aminosalicylic acid to faecal sulphide in patients with ulcerative colitis", Gut 2000, vol. 46, pp. 64 through 72.

Xu, Xi-Ming, et al., "Effects of garlicin on apoptosis in rat model of colitis", World J Gastoenterol, Aug. 7, 2005, vol. 11, No. 29, pp. 4579 through 4582.

* cited by examiner

**p<0.01

*p<0.05

*p<0.05

*p<0.05

**p<0.01

**p<0.01

*p<0.05, **p<0.01

*p<0.05, **p<0.01

*$p<0.05$

*p<0.05

DERIVATIVES OF 4- OR 5-AMINOSALICYLIC ACID

This application is a divisional of U.S. patent application Ser. No. 12/368,846, filed Oct. 2, 2009, which is a continuation of U.S. patent application Ser. No. 11/278,395, filed Mar. 31, 2006, which is a continuation-in-part of U.S. patent application Ser. No. 11/139,871, filed May 27, 2005.

FIELD OF THE INVENTION

The present invention relates to compounds useful in the treatment of an intestinal disease such as inflammatory bowel disease (IBD) and irritable bowel syndrome (IBS) and in colon cancer chemoprevention. In particular, 4- and 5-aminosalicylic acid derivatives have been developed having a hydrogen sulfide releasing moiety linked via an azo, an ester, an anhydride, a thioester or an amide linkage to a molecule of 5- or 4-aminosalicylic acid.

BACKGROUND OF THE INVENTION

Inflammatory bowel disease (IBD) is the general name for diseases that cause inflammation in the small intestine and colon. Ulcerative colitis is the most common inflammatory bowel disease and it affects various portions of the gastrointestinal (GI) tract, particularly the lower GI tract, and more particularly the colon and/or rectum. A second IBD is Crohn's disease, which predominates in the small intestine (ileum) and the large intestine (colon).

Ulcerative colitis can be difficult to diagnose in that its symptoms are similar to other intestinal disorders and to Crohn's disease. Crohn's disease differs from ulcerative colitis because it causes deeper inflammation into the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop this disease. Ulcerative colitis affects men and women equally and appears to run in some families.

It is also important to consider that about 5 percent of people with ulcerative colitis develop colon cancer. The risk of cancer increases with the duration and the extent of involvement of the colon. For example, if only the lower colon and rectum are involved, the risk of cancer is no higher than normal. However, if the entire colon is involved, the risk of cancer may be as much as 32 times the normal rate. Thus, it is possible that drugs useful in the treatment of IBD may also be useful in the prevention of colon cancer.

The pathogenesis of IBD likely involves multifactorial interactions among genetic factors, immunological factors and environmental triggers. Recent evidence suggests that a pathologic activation of the mucosal immune system in response to antigens is a key factor in the pathogenesis of IBD.

The presentation of antigen in the inflammatory process is closely followed by generation of cytokines, small glycoprotein peptide molecules, which provide signals for the communication among different cell populations determining the direction of subsequent immune and inflammatory response. Pro-inflammatory cytokines include interleukin (IL)-1, IL-6, IL-8 and tumor necrosis factor-alpha (TNF-α). Macrophages are the major source of cytokines, with epithelial cells also being able to produce a number of these peptide factors.

T helper (Th) cells are a further important source of cytokines. Th1 cells, which are associated with a cell-mediated immune response, produce IL-2, interferon gamma (IFN-☐γ) and TNF-α. A key transcription factor involved in the regulation of inflammation, NFkB, which is specifically implicated in the pathogenesis of IBD, regulates the amount of cytokines produced by the Th1 cells (see Neurath et al. (1996) *Nature Med.* 2: 998-1004). Th2 cells enhance antibody synthesis by B cells and produce IL-4, IL-5, IL-6, and IL-10.

Chemokines are also thought to contribute to the pathogenesis of colitis. Chemokines are pro-inflammatory proteins that participate in immune and inflammatory responses through the chemoattraction and activation of leukocytes. For example, RANTES is a C—C chemokine that promotes the recruitment and activation of inflammatory cells such as monocytes, lymphocytes, mast cells and eosinophils. RANTES has recently been shown to be elevated during the chronic phase of colitis (see Ajuebor et al. (2001) *J. Immunol.* 166: 552-558).

Treatment for ulcerative colitis depends on the seriousness of the illness. Most people are treated with medication. In severe cases, a patient may need surgery to remove the diseased colon.

Irritable bowel syndrome (IBS) is a common but poorly understood disorder that causes a variety of bowel symptoms including abdominal pain, diarrhea and/or constipation, bloating, gassiness and cramping. While these symptoms may be caused by a number of different bowel diseases, IBS is usually diagnosed only after exclusion of a more serious problem. There is increasing evidence suggesting the role of inflammation in the pathogenesis of IBS.

The goal of therapy is to induce and maintain remission, and to improve the quality of life for people with IBD/IBS. Several types of drugs are available.

Aminosalicylates, which are drugs that contain 5-aminosalicylic acid (5-ASA; mesalamine) or 4-aminosalicylic acid (4-ASA), help to control the inflammation. However, both mesalamine and 4-ASA may be absorbed as it passes through the GI tract and may adversely affect the amount of mesalamine that reaches the lower GI tract, particularly the colon and rectum. Thus, various mesalamine formulations have been introduced in an attempt to protect mesalamine as it passes through the gut and upper GI tract.

In addition, several pro-drugs of mesalamine have been introduced which can aid in colon-specific delivery of mesalamine. These pro-drugs are generally less readily absorbed in the gut and upper GI tract and thus can more easily reach the colon.

Sulfasalazine is a combination of sulfapyridine and 5-ASA and is employed to induce and maintain remission. Sulfasalazine is metabolized in the body to form 5-ASA and sulfapyridine. The sulfapyridine component carries the anti-inflammatory 5-ASA to the intestine.

However, sulfapyridine may lead to side effects, such as nausea, vomiting, heartburn, diarrhea, and headache. These adverse side effects are usually attributed to the activity of sulfapyridine in the GI tract, as well as that absorbed into the system.

Other 5-ASA agents such as olsalazine, ipsalazide and balsalazide, each of which have a different carrier, offer fewer side effects, and may be used by people who cannot take sulfasalazine. Unlike sulfasalazine, the breakdown of these 5-ASA compounds in the intestinal tract may not give rise to undesirable metabolic products.

In general, 5-ASA compounds are given orally, through an enema, or in a suppository, depending on the location of the inflammation in the colon. Most people with mild or moderate ulcerative colitis are treated with this group of drugs first. However, in general, this therapy cannot be considered optimal, mainly because of the poor potency of the drug that causes also a poor compliance for the patient.

Other drugs that are used are corticosteroids such as prednisone, hydrocortisone, budesonide etc. and immunomodulators such as azathioprine and 6-mercaptopurine (6-MP). These drugs can cause side effects such as hypertension, increased risk of infections etc.

Sulfasalazine, olsalazide and balsalazide are mesalamine derivatives where the non-mesalamine carrier is linked to mesalamine via a diazo bond. These pro-drugs are not as readily absorbed in the gut and upper GI tract and thus can reach the colon where they are split by azo-reductases of the colonic microflora to release the mesalamine and carrier directly in the colon.

Other derivatives of mesalamine comprise a carrier attached to mesalamine via the carboxylic and hydroxyl functional groups of the molecule. Among these, the preparation of esters or amides with amino acids such as L-serine and L-glycine or the addition of other biological compound such as taurine has been reported. These pro-drugs base their activity on the action of carboxypeptidases and aminopeptidases A for releasing mesalamine. (R. Pellicciari et al. (1993) *Journal of Medicinal Chemistry*, 36, pg. 4201-7).

Most of the prior art carrier moieties attached to mesalamine are inert. Thus, it is desirable to link carrier moieties to either 5-ASA or 4-ASA, which are also biologically active and useful in the treatment of IBD/IBS.

SUMMARY OF THE INVENTION

In general, a hydrogen sulfide ($H_2S$) releasing moiety that is capable of releasing $H_2S$ in tissue is linked via an azo, an ester, an anhydride, a thioester or an amide linkage to a molecule of 4- or 5-aminosalicylic acid (4- or 5-ASA) to form a 4- or 5-ASA derivative of the present invention. By covalently attaching the $H_2S$ releasing moiety to 4- or 5-ASA, the derivatives of the present invention may act as pro-drugs that are generally less readily absorbed in the gut and upper GI tract and thus can more easily reach the colon.

The anti-inflammatory properties of 4- or 5-ASA and their use to treat ulcerative colitis are well documented. 4- or 5-ASA reduces bowel inflammation, diahhrea (stool frequency), rectal bleeding and stomach pain. $H_2S$ has been recently shown to function as a neuromodulatory and to exert anti-inflammatory actions. Further, $H_2S$ has been shown to modulate nociception to colorectal distention (see Distrutti et al. (2005) Evidence That Hydrogen Sulfide Exerts Antinociceptive Effects in the Gastrointestinal Tract by Activating $K_{ATP}$ Channels. *J. Pharm. and Exp. Ther.* 316: 325-335, incorporated herein by reference). Finally, $H_2S$ has been shown to be a smooth muscle relaxant in intestinal tissues (see Teague, B. et al. (2002) The Smooth Muscle Relaxant effect of Hydrogen Sulfide In Vitro: Evidence for a Physiological Role to Control Intestinal Contractility. *Br. J. Pharmacol.* 137: 139-145, incorporated herein by reference).

Surprisingly, covalently attaching the $H_2S$ releasing moiety to 4- or 5-ASA improves the $H_2S$ releasing capabilities of the $H_2S$ moiety as compared to the $H_2S$ moiety alone. This suggests that $H_2S$ may be released both while the $H_2S$ releasing moiety is covalently attached to 4- or 5-ASA as well as after the $H_2S$ releasing moiety is cleaved from the 4- or 5-ASA by hydrolysis or cleavage by various enzymes present in the GI tract to release the two active ingredients, namely, 4- or 5-aminosalicylic acid and the $H_2S$ releasing moiety for further action.

The derivatives of the present invention are superior to 4- or 5-ASA alone, $H_2S$ releasing moiety alone and a mixture of 4- or 5-ASA and $H_2S$ releasing moiety in reducing inflammation, reducing diahhrea and fecal occult blood in subjects with colitis, and reducing visceral pain associated with colorectal distention. Further, the derivatives of the present invention also reduce mRNA levels of cyclooxygenase (COX)-1, COX-2, constitutive endothelial nitric oxide synthase (eNOS), and inducible NOS (iNOS), all of which are enzymes believed to be involved in inflammation.

Thus, in one aspect of the invention, the derivatives of the present invention are useful in treating an inflammatory condition of the gastrointestinal (GI) tract, such as inflammatory bowel disease (IBD) and irritable bowel syndrome (IBS). Without being bound to theory, it is thought that the hydrogen sulfide released from the hydrogen sulfide releasing moiety exerts anti-inflammatory effects via the inhibition of NFkB, the transcription factor that regulates the expression of several of the pro-inflammatory genes. Further, it is thought that the antinociceptive effects of $H_2S$ may involve the ATP-sensitive $K^+$ ($K_{ATP}$) channels.

In another aspect of the invention, the 4- or 5-ASA derivatives of the present invention are effective in decreasing the viability of HT-29 human colon cancer cells and thus are useful in the prevention and/or treatment of colon cancer.

Broadly stated, compounds of the invention have the following general formula:

where:
A is

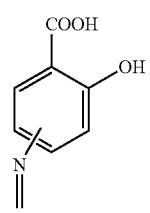

where —N= is either at position 4 or 5,

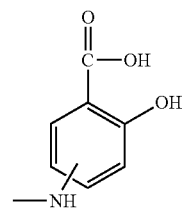

where —NH is either at position 4 or 5,

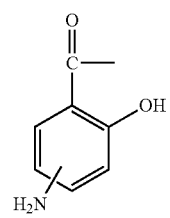

where —NH$_2$ is either at position 4 or 5,
or

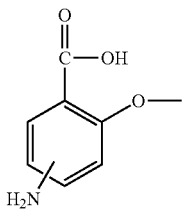

where —NH$_2$ is either at position 4 or 5;

L is either O, O—C═O, S, N or a covalent bond to form an ester linkage, an anhydride linkage, a thioester linkage, an amide linkage or an azo linkage; and R is a hydrogen sulfide releasing moiety that releases H$_2$S in tissue. It is understood that any non-toxic, effective hydrogen sulfide releasing moiety that releases H2S in the presence of tissue can be used in the present invention.

In a preferred embodiment, R is selected from the group consisting of:

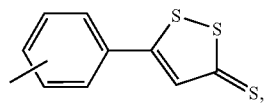

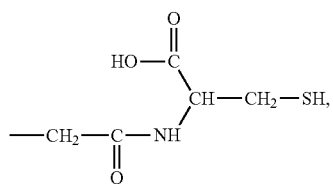

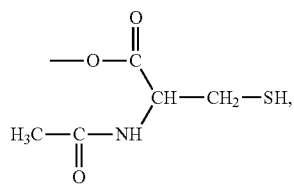

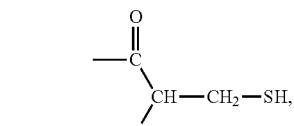

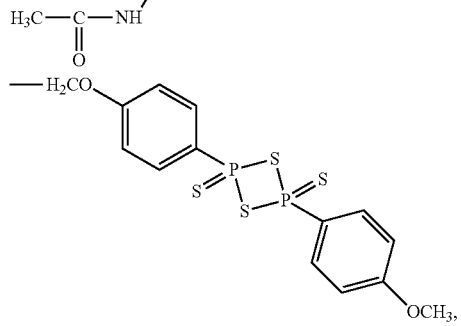

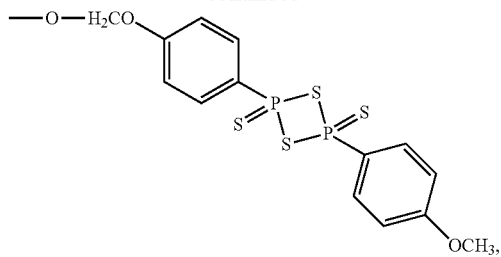

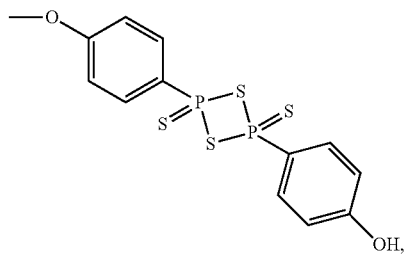

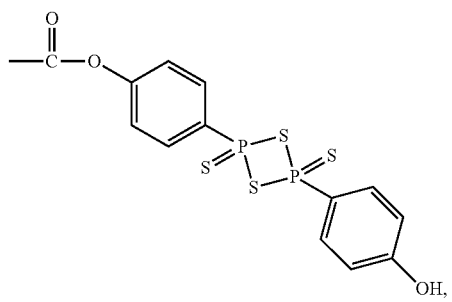

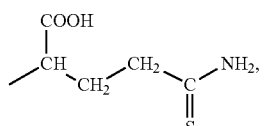

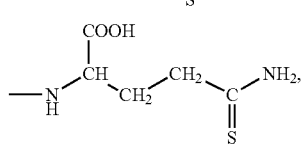

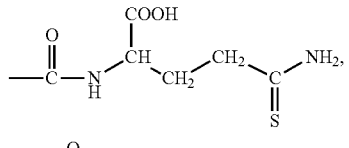

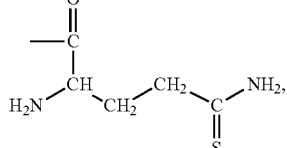

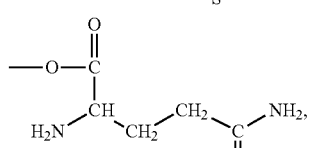

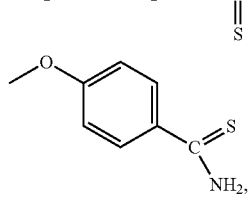

-continued

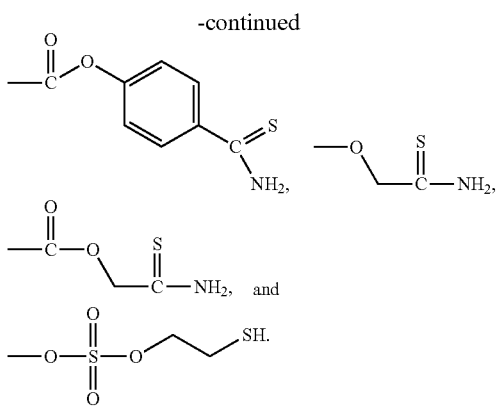

All of the above moieties release H₂S in biological tissues; however, most of the H₂S releasing moieties do so by a different mechanism than N-acetylcysteine. It is well known that N-acetylcysteine is converted to cysteine in various tissues, and that cysteine metabolism in vivo produces H₂S. H₂S is produced mainly by two types of pyridoxal 5'-phosphate dependent enzymes responsible for metabolism of L-cysteine, namely, cystathione γ-lyase and cystathione β-synthase (see Fujii et al. (2005) Hydrogen Sulfide as an Endogenous Modulator of Biliary Bicarbonate Excretion in the Rat Liver. *Antioxid. Redox Signal.* 7: 788-794, incorporated herein by reference).

Pharmaceutical acceptable salts such as for example salts with alkaline metals and alkaline earth metals, non-toxic amines and amino acids are also part of the present invention. Preferred salts are the salts with arginine and agmatine. Also included are pharmaceutically acceptable acid addition salts.

In a further aspect the present invention provides a pharmaceutical composition of the compounds of the present invention, and a pharmaceutically acceptable excipient or carrier, particularly one for use in the treatment of an inflammatory condition of the GI tract.

According to other embodiments of the present invention, methods of treating an inflammatory condition of the GI tract, such as inflammatory bowel disease (IBD) and irritable bowel syndrome (IBS), in a subject in need of such treatment, include administering to the subject an effective amount of 4- or 5-ASA derivatives and their salts. Further, methods for the treatment or prevention of colon cancer in a subject in need thereof are provided comprising administering to the subject an effective amount of 4- or 5-ASA derivatives and their salts.

In a further embodiment, the present invention provides the use of 4- or 5-ASA derivatives and their salts of the present invention for the manufacture of a medicament for the treatment of an inflammatory condition of the GI tract. The present invention also provides the use of 4- or 5-ASA derivatives and their salts for the treatment of an inflammatory condition of the GI tract.

Preferred compounds are those of the following formulae:

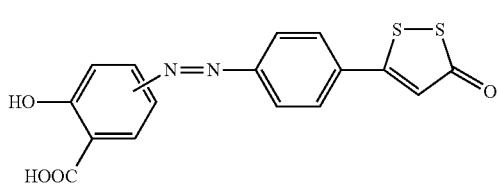

2-Hydroxy-4- or 5-[4-(5-thioxo-5H-[1,2]dithiol-3-yl)-phenylazo]-benzoic acid (II)

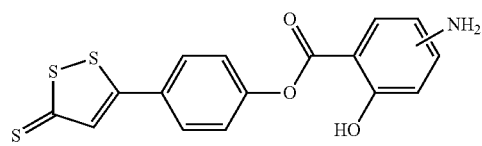

4- or 5-Amino-2-hydroxy-benzoic acid 4-(5-thioxo-5H-[1,2]dithiol-3-yl)-phenyl ester (III)

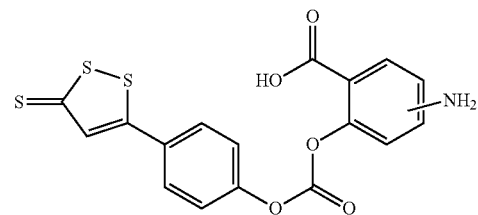

4 or 5-Amino-2-[4-(5-thioxo-5H-[1,2]dithiol-3-yl)-phenoxycarbonyloxy]-benzoic acid (IV)

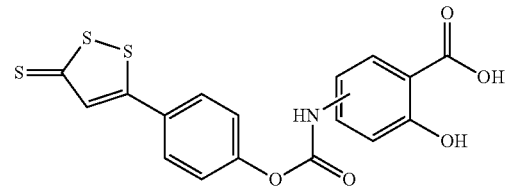

2-Hydroxy-4 or 5[4-(5-thioxo-5H-[1,2]dithiol-3-yl)-phenoxycarbonylamino]-benzoic acid (V)

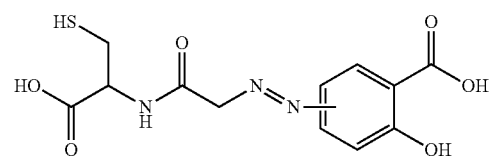

4- or 5-{[(1-Carboxy-2-mercapto-ethylcarbamoyl)-methyl]-azo}-2-hydroxy-benzoic acid (VI)

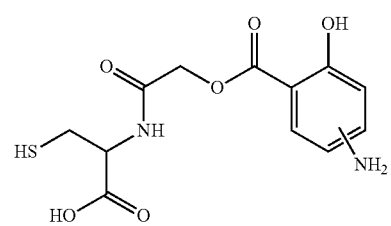

4- or 5-Amino-2-hydroxy-benzoic acid (1-carboxy-2-mercapto-ethylcarbamoyl)-methyl ester (VII)

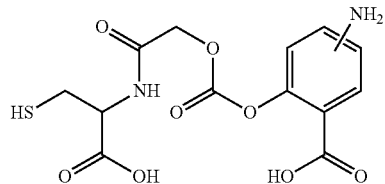

4- or 5-Amino-2-[(1-carboxy-2-mercapto-ethylcarbamoyl)-methoxycarbonyloxy]-benzoic acid (VIII)

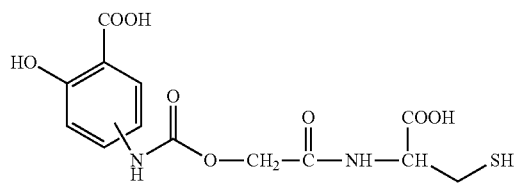

4- or 5-[(1-Carboxy-2-mercapto-ethylcarbamoyl)-methoxycarbonylamino]-2-hydroxy-benzoic acid (IX)

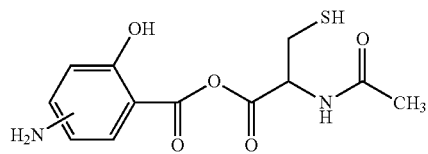

4- or 5-amino-2-hydroxy-benzoic acid anhydride with N-acetylcysteine (X),

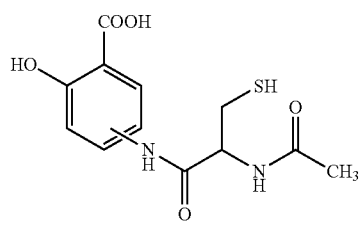

4- or 5-(2-Acetylamino-3-mercapto-propionylamino)-2-hydroxy-benzoic acid (XI)

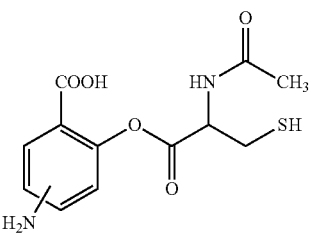

2-(2-Acetylamino-3-mercapto-propionyloxy)-4 or 5-amino-benzoic acid (XII)

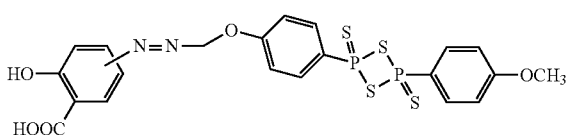

2-Hydroxy-4 or 5-({4-[4-(4-methoxy-phenyl)-2,4-dithioxo-2$\lambda^5$,4$\lambda^5$-[1,3,2,4]dithiadiphosphetan-2-yl]-phenoxymethyl}-azo)-benzoic acid (XIII)

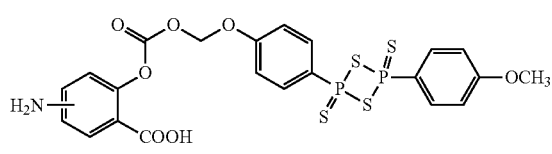

4- or 5-Amino-2-{4-[4-(4-methoxy-phenyl)-2,4-dithioxo-2$\lambda^5$,4$\lambda^5$-[1,3,2,4]dithiadiphosphetan-2-yl]-phenoxymethoxycarbonyloxy}-benzoic acid (XIV)

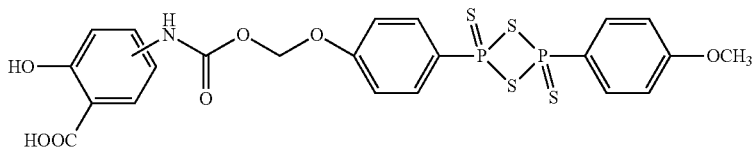

2-Hydroxy-4- or 5-{4-[4-(4-methoxy-phenyl)-2,4-dithioxo-2λ$^5$,4λ$^5$-[1,3,2,4]dithiadiphosphetan-2-yl]-phenoxymethoxycarbonylamino}-benzoic acid (XV)

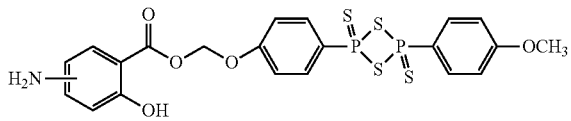

4- or 5-Amino-2-hydroxy-benzoic acid 4-[4-(4-methoxy-phenyl)-2,4-dithioxo-2λ$^5$,4λ$^5$-[1,3,2,4]dithiadiphosphetan-2-yl]-phenoxymethyl ester (XVI)

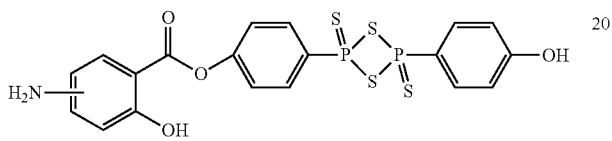

4- or 5-Amino-2-hydroxy-benzoic acid 4-[4-(4-hydroxy-phenyl)-2,4-dithioxo-2λ$^5$,4λ$^5$-[1,3,2,4]dithiadiphosphetan-2-yl]-phenyl ester (XVII)

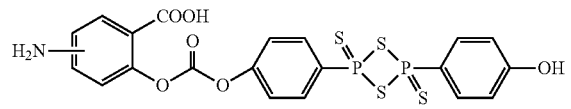

4- or 5-Amino-2-{4-[4-(4-hydroxy-phenyl)-2,4-dithioxo-2λ$^5$,4λ$^5$-[1,3,2,4]dithiadiphosphetan-2-yl]-phenoxycarbonyloxy}-benzoic acid (XVIII)

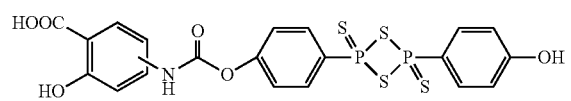

2-Hydroxy-4- or 5-{4-[4-(4-hydroxy-phenyl)-2,4-dithioxo-2λ$^5$,4λ$^5$-[1,3,2,4]dithiadiphosphetan-2-yl]-phenoxycarbonylamino}-benzoic acid (XIX)

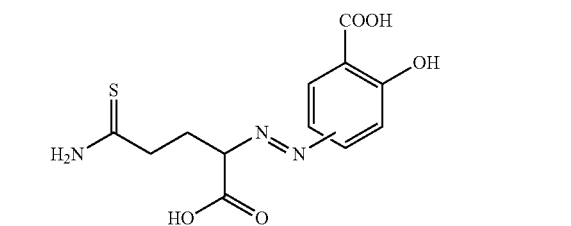

4- or 5-(1-Carboxy-3-thiocarbamoyl-propylazo)-2-hydroxy-benzoic acid (XX)

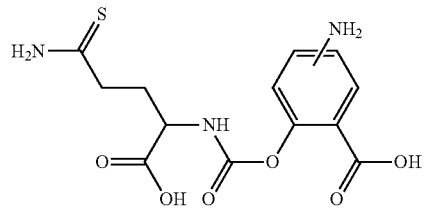

2-(4- or 5-Amino-2-hydroxy-benzoylamino)-4-thiocarbamoyl-butyric acid (XXI)

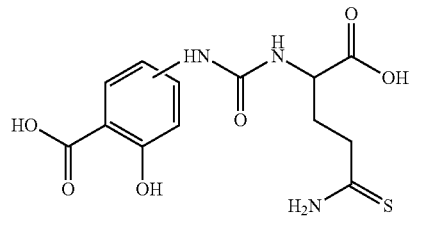

4- or 5-Amino-2-(1-carboxy-3-thiocarbamoyl-propylcarbamoyloxy)-benzoic acid (XXII)

2-Hydroxy-4- or 5-[3-(1-hydroxymethyl-3-thiocarbamoyl-propyl)-ureido]-benzoic acid (XXIII)

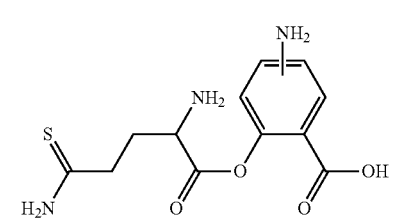

4- or 5-Amino-2-(2-amino-4-thiocarbamoyl-butyryloxy)-benzoic acid (XXIV)

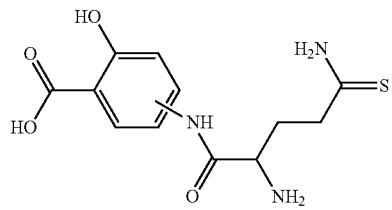

4- or 5-(2-Amino-4-thiocarbamoyl-butyrylamino)-2-hydroxy-benzoic acid (XXV)

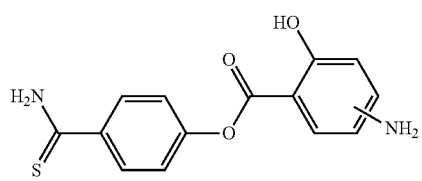

4- or 5-Amino-2-hydroxy-benzoic acid anhydride with 2-amino-4-thiocarbamoyl-butyric acid (XXVI)

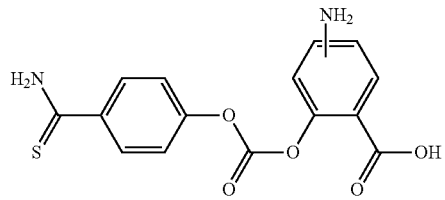

4-thiocarbamoylphenyl 4- or 5-amino-2-hydroxybenzoate (XXVII)

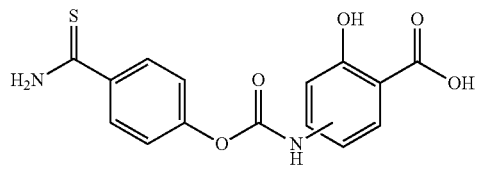

4- or 5-Amino-2-(4-thiocarbamoyl-phenoxycarbonyloxy)-benzoic acid (XXVIII)

2-Hydroxy-4- or 5-(4-thiocarbamoyl-phenoxycarbonylamino)-benzoic acid (XXIX)

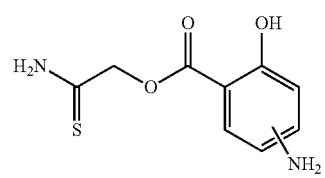

4- or 5-Amino-2-hydroxy-benzoic acid thiocarbamoylmethyl ester (XXX)

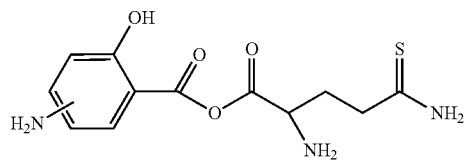

4- or 5-Amino-2-thiocarbamoylmethoxycarbonyloxy-benzoic acid (XXXI)

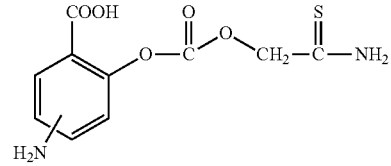

2-Hydroxy-4- or 5-thiocarbamoylmethoxycarbonylamino-benzoic acid (XXXII)

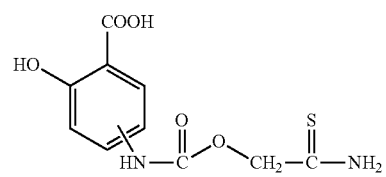

4- or 5-Amino-2-hydroxy-benzoic acid anhydride with sulfuric acid mono-(2-mercapto-ethyl)ester (XXXIII)

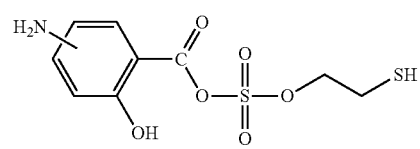

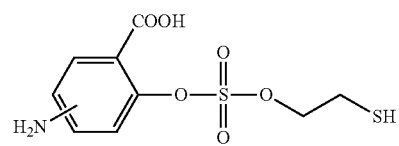

4- or 5-Amino-2-(2-mercapto-ethoxysulfonyloxy)-benzoic acid (XXXIV), and

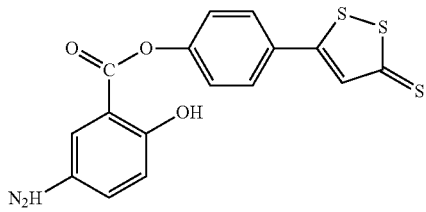

5-Amino-2-hydroxy-benzoic acid 4-(5-thioxo-5H-[1,2]dithiol-3-yl)-phenyl ester (XXXV)

The most preferred compounds are as follows:

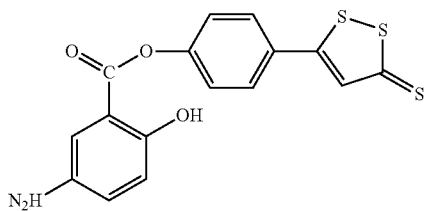

5-Amino-2-hydroxy-benzoic acid 4-(5-thioxo-5H-[1,2]dithiol-3-yl)-phenyl ester (XXXV)

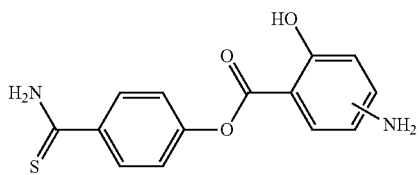

4-thiocarbamoylphenyl 4- or 5-amino-2-hydroxybenzoate (XXVII); and

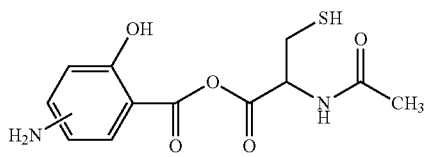

4- or 5-amino-2-hydroxy-benzoic acid anhydride with N-acetylcysteine (X)

DETAILED DESCRIPTION OF THE PREFERRED EMBODIMENT

Figure 1:
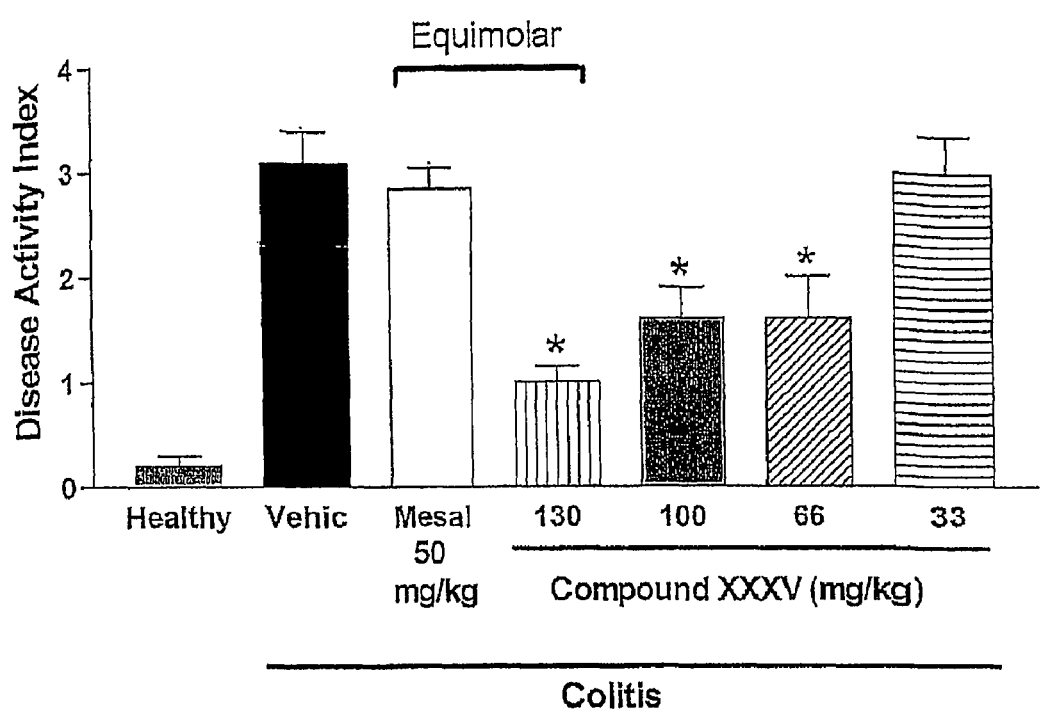
FIG. 1 shows the Disease Activity Score of mice having TNBS-induced colitis after treatment with increasing doses of mesalamine and Compound XXXV of the present invention.

The invention will now be described with respect to preferred embodiments described herein. It should be appreciated however that these embodiments are for the purpose of illustrating the invention, and are not to be construed as limiting the scope of the invention as defined by the claims.

The compounds of the present invention contain two active moieties, either 4- or 5-ASA and a hydrogen sulfide releasing moiety, linked together by an azo, ester, anhydride, thioester or amide linkage. The presence of azo-reductase enzymes allow for the release of 4- or 5-ASA from the azo bond pro-drugs thus allowing a targeted delivery to the colon and reducing at the same time the systemic absorption. Similarly, the presence of carboxypeptidases and aminopeptidases A also allow for the release of 4- or 5-ASA from the ester and amide bond pro-drugs, respectively. Esterases and thioesterases will also cleave ester and thioester linkages, respectively. Finally, lipases will cleave anhydride linkages. The compounds of the present invention can be made using known starting materials and reagents.

Compounds of the present invention may be utilized for the prophylaxis or treatment of various diseases, particularly inflammatory conditions of the GI tract including, but not limited to, inflammatory conditions of the mouth such as mucositis, infectious diseases (e.g., viral, bacterial and fungal diseases), and Crohn's disease; inflammatory conditions of the esophagus such as esophagitis, conditions resulting from chemical injury (e.g., lye ingestion), gastroesophageal reflux disease, bile acid reflux, Barrett's esophagus, Crohn's disease, and esophageal stricture; inflammatory conditions such as gastritis (e.g., *Helicobacter pylori*, acid-peptic disease and atrophic gastritis), celiac disease, peptic ulcer disease, precancerous lesions of the stomach, non-ulcer dyspepsia, and Crohn's disease; inflammatory conditions of the stomach such as Crohn's disease, bacterial overgrowth, peptic ulcer disease, and fissures of the intestine; inflammatory conditions of the colon such as Crohn's disease, ulcerative colitis, irritable bowel syndrome, infectious colitis (e.g., pseudomembranous colitis such as *Clostridium difficile* colitis, *salmonella enteritis, shigella* infections, yersiniosis, cryptospiridiosis, microspridial infections, and viral infections), radiation-induced colitis, colitis in the immunocompromised host (e.g., typhlitis), precancerous conditions of the colon (e.g., dysplasia, inflammatory conditions of the bowel, and colonic polyps), proctitis, inflammation associated with hemorrhoids, proctalgia fugax, and rectal fissures; liver gallbladder and/or bilary tract conditions such as cholangitis, sclerosing cholangitis, primary bilary cirrhosis, and cholecystitis; and intestinal abscess.

Depending on the specific condition or disease state to be treated, subjects may be administered compounds of the present invention at any suitable therapeutically effective and safe dosage, as may be readily determined within the skill of the art. These compounds are, most desirably, administered in dosages ranging from about 1 to about 2000 mg per day, in a single or divided doses, although variations will necessarily occur depending upon the weight and condition of the subject being treated and the particular route of administration chosen. However, a dosage level that is in the range of about 0.1 to about 100 mg/kg, preferably between about 5 and 90 mg/kg, and more preferably between about 5 and 50 mg/kg, is most desirable. Variations may nevertheless occur depending upon the weight and conditions of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such large doses are first divided into several small doses for administration throughout the day.

The compounds of the present invention can be administered in the form of any pharmaceutical formulation, the nature of which will depend upon the route of administration. These pharmaceutical compositions can be prepared by conventional methods, using compatible, pharmaceutically acceptable excipients or vehicles. Examples of such compositions include capsules, tablets, transdermal patches, lozenges, troches, sprays, syrups, powders, granulates, gels, elixirs, suppositories, and the like, for the preparation of extemporaneous solutions, injectable preparations, rectal, nasal, ocular, vaginal etc. A preferred route of administration is the oral and rectal route.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with sweetening or flavoring agents, coloring matter and, if so desired, emulsifying and/or suspending agents, together with such diluents as water, ethanol, propylene glycol, glycerin and various combinations thereof.

The dosage form can be designed for immediate release, controlled release, extended release, delayed release or targeted delayed release. The definitions of these terms are known to those skilled in the art. Furthermore, the dosage form release profile can be effected by a polymeric mixture composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. The aqueous solutions are suitable for intravenous injection purposes. The preparation of all these solutions under sterile conditions is readily accomplished by standard pharmaceutical techniques well known to those skilled in the art.

The following non-limiting examples further describe and enable a person ordinarily skilled in the art to make and use the invention.

Preparation of Compounds

EXAMPLE 1

Synthesis of 2-Hydroxy-5-[4-(5-thioxo-5H-[1,2] dithiol-3-yl)-phenylazo]-benzoic acid (4) [Compound of Formula II]

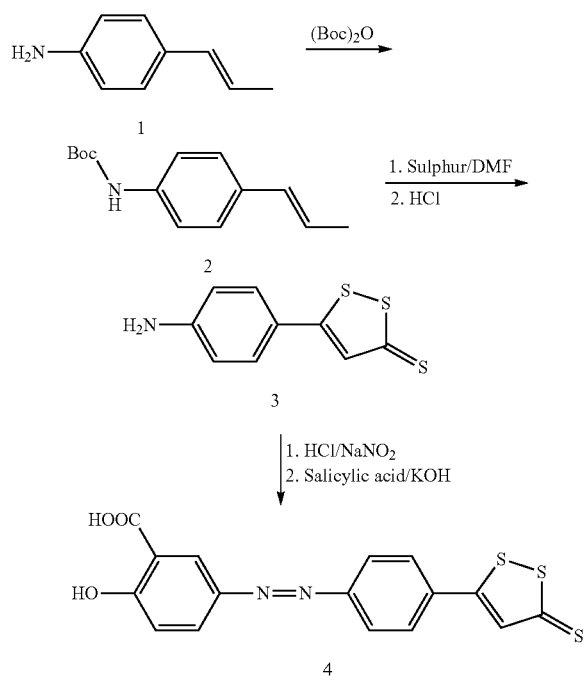

Synthesis of (4-Propenyl-phenyl)-carbamic acid tert-butyl ester (2)

To the solution of 4-propenyl-phenylamine (1) (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3 M HCl (15 mL), was added drop wise to the residue. The precipitate is filtered, washed with water and dried. The residue was loaded on a silica gel open column and eluted with CH$_2$Cl$_2$/MeOH (9/1), from which (4-Propenyl-phenyl)-carbamic acid tert-butyl ester (2) was obtained (90% yield).

Synthesis of 5-(4-Amino-phenyl)-[1,2]dithiole-3-thione (3)

(4-Propenyl-phenyl)-carbamic acid tert-butyl ester (2, 4.5 mmol) and sulphur (31.5 mmol) were heated in dimethyl formamide (500 ml) for 8 hr; the residue after removal of solvent was almost completely soluble in toluene. An attempt to extract the toluene liquors with 2N aqueous sodium hydroxide, gave a precipitate of an orange solid. This product was dissolved in boiling water, treated with 4N hydrochloric acid for 30 min at room temperature; addition of 4N NaOH furnished the desired product (3) (yield 55%).

Synthesis of 2-Hydroxy-5-[4-(5-thioxo-5H-[1,2] dithiol-3-yl)-phenylazo]-benzoic acid (4)

5-(4-Amino-phenyl)-[1,2]dithiole-3-thione (3, 0.56 mmol) was dissolved in a mixture of 5 mL of concentrated HCl and 2.5 mL of water and diazotized with a solution of sodium nitrite (0.56 mmol). In the meantime salicylic acid (0.56 mmol), potassium hydroxide (1.12 mmol) and sodium carbonate are dissolved in water. The diazo suspension is added in portions to the alkaline solution of salicylic acid and the alkalinity maintained at a sufficiently high level during the whole reaction by means of addition of further quantities of potassium hydroxide solution. After 2 days the reaction mixture is heated for 30 min at 50° C. The azo compound (4) was precipitated by means of HCl and filtered off (yield 85%), to yield the compound of Formula II, 2-Hydroxy-5-[4-(5-thioxo-5H-[1,2]dithiol-3-yl)-phenylazo]-benzoic acid.

EXAMPLE 2

Synthesis of 2-Hydroxy-4-[4-(5-thioxo-5H-[1,2] dithiol-3-yl)-phenylazo]-benzoic acid (2) [Compound of Formula II]

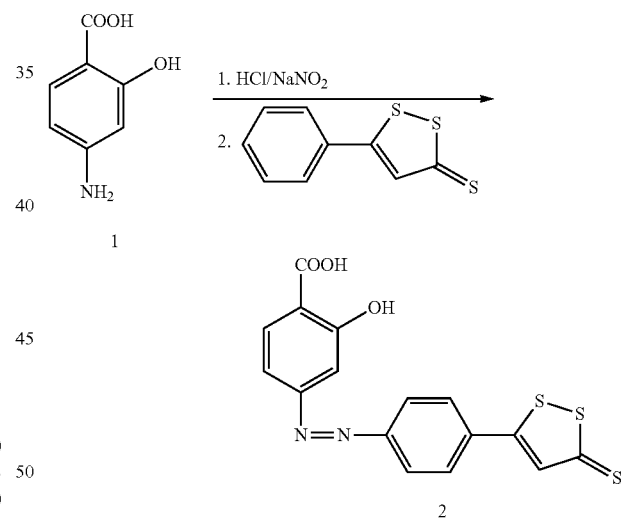

Synthesis of 2-Hydroxy-4-[4-(5-thioxo-5H-[1,2] dithiol-3-yl)-phenylazo]-benzoic acid (2)

4-Amino-2-hydroxy-benzoic acid (1, 1 mmol) was dissolved in a mixture of 10 mL of concentrated HCl and 5 mL of water and diazotized with a solution of sodium nitrite (1 mmol). The diazo suspension is added in portions to a solution of 5-phenyl-[1,2]dithiole-3-thione (1 mmol) in dimethylformamide. After 2 days the reaction mixture is heated for 30 min at 50° C. After cooling the azo compound (2) was precipitated by means of HCl and filtered off (yield 65%), to yield the compound of Formula II, 2-Hydroxy-5-[4-(5-thioxo-5H-[1,2]dithiol-3-yl)-phenylazo]-benzoic acid.

EXAMPLE 3
General Synthetic Procedure of
4- or 5-Amino-2-hydroxy-benzoic acid 4-(5-thioxo-5H-[1,2]dithiol-3-yl)-phenyl ester (4) [Compound of Formula XXXV]
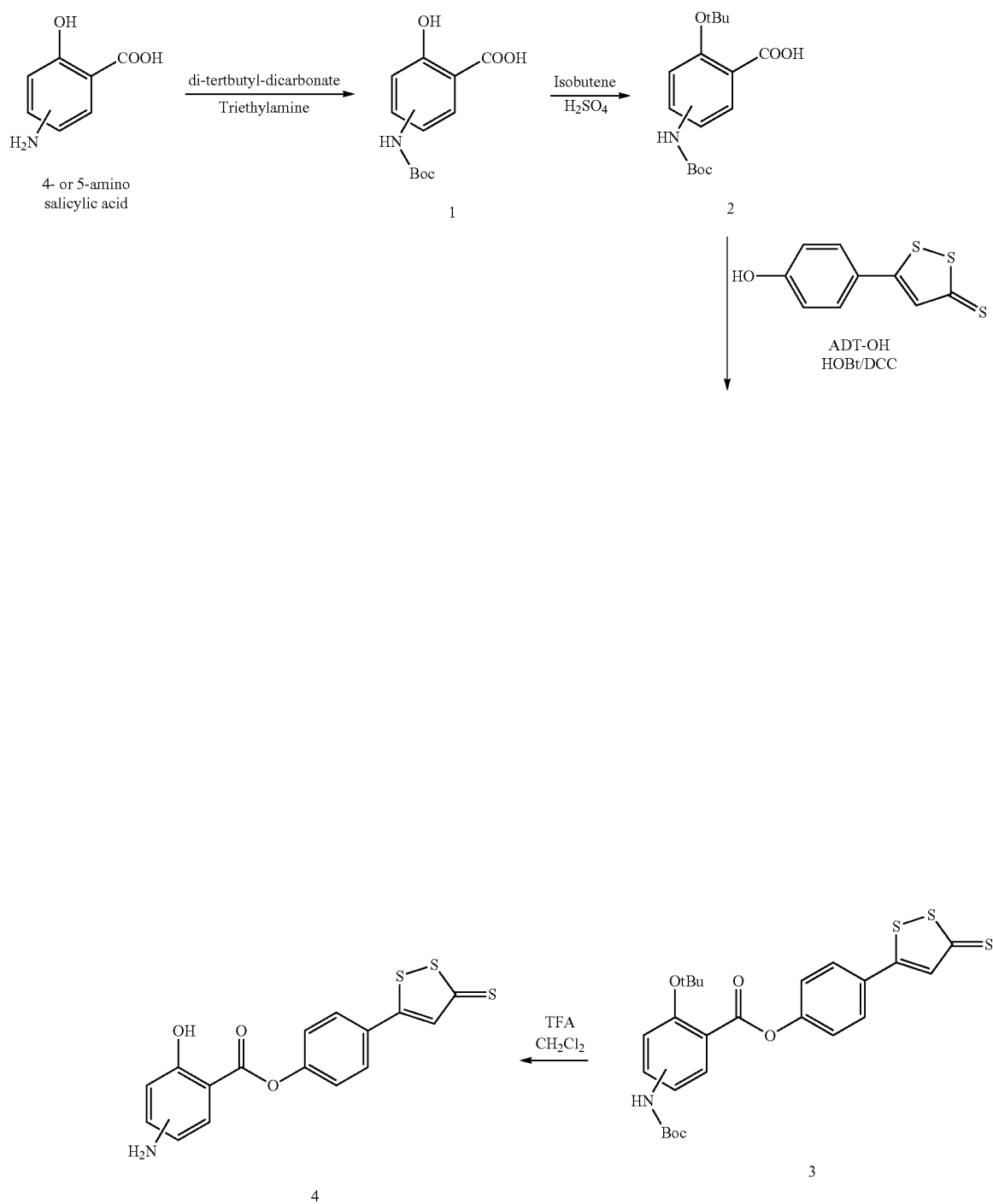

Synthesis of 5-p-hydroxyphenyl-1,2-dithione-3-thione (ADT-OH)

Anethole (1) (32.5 g; 0.21 mol) and sulphur (45 g; 1.40 mol) were heated in dimethylformamide (250 ml) for 8 hr; the residue after removal of solvent was almost completely soluble in toluene. An attempt to extract the toluene liquors with 2N-aqueous sodium hydroxide, gave a precipitate of an orange solid (8.5 g). m.p. over 300° C. This product was dissolved in boiling water and gave an orange precipitate (2) after addition of hydrochloric acid (Yield 50%), m.p. 188-189° C. $^1$H NMR (DMSO) δ 6.86 (d, 2H), 7.68 (s, 1H), 7.75 (d, 2H), 10.51 (s, —OH); MS (ESI), m/z 225 (M$^-$).

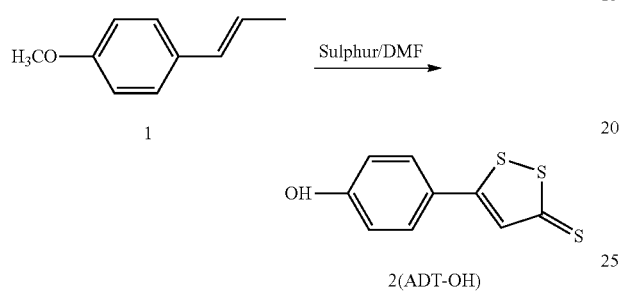

Synthesis of 4- or 5-tert-Butoxycarbonylamino-2-hydroxy-benzoic acid (1)

To the solution of 4- or 5-amino salicylic acid (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3M HCl (15 mL), was added drop wise to the residue. The precipitate is filtered, washed with water and dried. The residue was loaded on a silica gel open column and eluted with CH$_2$Cl$_2$/MeOH (9/1), from which 4- or 5-tert-Butoxycarbonylamino-2-hydroxy-benzoic acid (1) was obtained (80% yield).

Synthesis of 4- or 5-tert-Butoxycarbonylamino-2-tert-butoxy-benzoic acid (2)

Compound (1) (12.0 mmol), conc. H$_2$SO$_4$ (6.0 mmol), and DCM (100 mL) were stirred under isobutylene gas (5 psi) for 6 h at room temperature. The solution was washed with cold 10% NaHCO$_3$ (2×100 mL) and brine (100 mL), dried (Na$_2$SO$_4$) and evaporated. The residue was dissolved in 1:1 MeOH/CCl$_4$ (400 mL), washed with water (300 mL), and then extracted with 1:1 MeOH/water (2×200 mL). The extract was dried (Na$_2$SO$_4$) and evaporated to a white solid (2), which was recrystallized by DCM/hexane (83% yield).

Synthesis of 4- or 5-Amino-2-hydroxy-benzoic acid 4-(5-thioxo-5H-[1,2]dithiol-3-yl)-phenyl ester (4)

To the solution of 4- or 5-tert-butoxycarbonylamino-2-hydroxy-benzoic acid (2) (3.0 mmol) in 50 mL of dimethyl-formamide, hydroxybenzotriazole (3.3 mmol) and DCC (3.3 mmol) were added with stirring at 0° C. for 1 h. To the reaction mixture, 5-p-hydroxyphenyl-1,2-dithione-3-thione (ADT-OH) (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous MgSO$_4$, filtered and the solvent evaporated. The crude intermediate (3) was treated with a solution of 40% TFA in CH$_2$Cl$_2$. After 2 h the solvent was removed to obtain compound 3 as a crude residue. The residue was loaded on a silica gel open column and eluted with CH$_2$Cl$_2$/MeOH (8/2), from which 4- or 5-amino-2-hydroxy-benzoic acid 4-(5-thioxo-5H-[1,2]dithiol-3-yl)-phenyl ester (4) [compound of Formula XXXV] was obtained (40% yield).

Compound 5-amino-2-hydroxy-benzoic acid 4-(5-thioxo-5H-[1,2]dithiol-3-yl)-phenyl ester (4): $^1$H NMR (DMSO) δ 7.07 (d, 2H), 7.38 (d, 2H), 7.46 (d, 2H), 7.79 (s, 1H), 7.85 (s, 1H), 8.01 (d, 2H), 10.35 (s, —OH); MS (ESI), m/z 362 (M$^+$).

EXAMPLE 4

General Synthetic Procedure of

2-(tert-butoxycarbonyl)-4- or 5-aminophenyl hydrogen carbonate (5)

3-(tert-butoxycarbonyl)-4- or 5-hydroxyphenyl-carbamic acid (6)

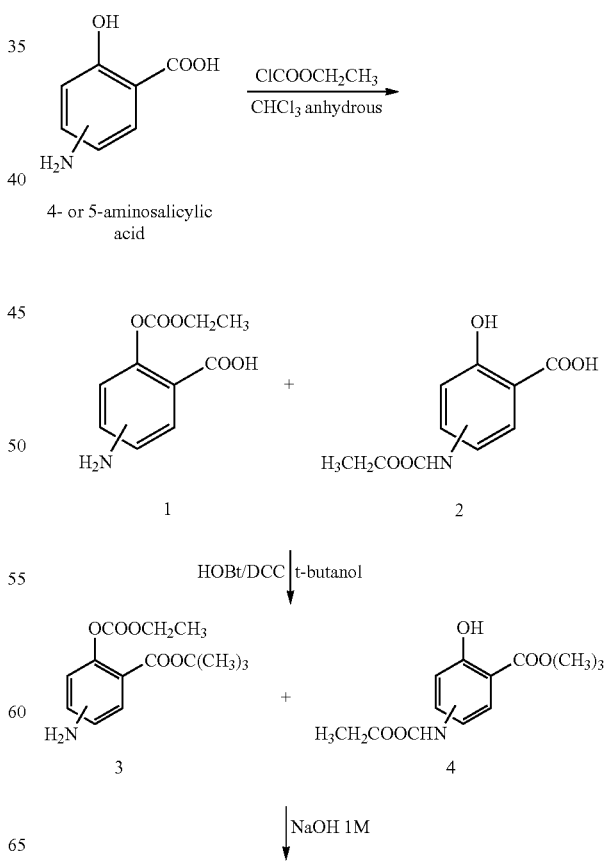

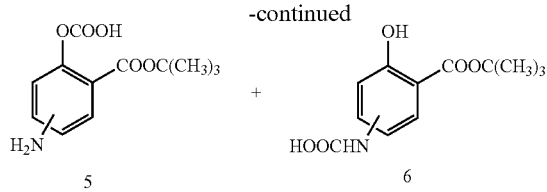

Synthesis of 4- or 5-Amino-2-ethoxycarbonyloxy-benzoic acid (1) and 4- or 5-ethoxycarbonylamino-2-hydroxy-benzoic acid (2)

4- or 5-amino salicylic acid (3.0 mmol) was dissolved in 40 mL chloroform in round-bottomed flask fitted with a drying tube. Ethyl chloroformate (3.0 mmol) was added gradually and the solution refluxed for 2 hours. The chloroform was evaporated in vacuo and the residue then taken up in ether. The ether phase was decolorized using charcoal, filtered and the solvent removed in vacuo. The residue obtained was then dissolved in ethanol and the product recovered by precipitation using n-hexane as a crude oily semisolid. The crude product was purified by Flash-chromatography on silica gel eluting with diethyl ether/hexane (7:3, v/v) to obtain the title compounds: 4- or 5-Amino-2-ethoxycarbonyloxy-benzoic acid (1: yield: 58%) and 4- or 5-Ethoxycarbonylamino-2-hydroxy-benzoic acid (2: yield: 34%).

Synthesis of 4- or 5-Amino-2-ethoxycarbonyloxy-benzoic acid tert-butyl ester (3)

To the solution of (1) (3.0 mmol) in 50 mL of dimethylformamide, hydroxybenzotriazole (3.3 mmol) and DCC (3.3 mmol) were added with stirring at 0° C. for 1 h. To the reaction mixture, t-butanol (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous MgSO$_4$, filtered and the solvent evaporated. The residue was loaded on a silica gel open column and eluted with CH$_2$Cl$_2$/MeOH (9.5/0.5), from which 4- or 5-Amino-2-ethoxycarbonyloxy-benzoic acid tert-butyl ester (3) was obtained (55% yield).

Synthesis of 4- or 5-ethoxycarbonylamino-2-hydroxy-benzoic acid tert-butyl ester (4)

Compound (4) was obtained according the procedure reported to obtain compound (3). Yield: 74%

Synthesis of 2-(tert-butoxycarbonyl)-4- or 5-aminophenyl hydrogen carbonate (5)

To a solution of the compound (3) (3.5 g; 0.011 mol) in ethanol (80 ml) was added NaOH 1N (40 ml). The reaction mixture was stirred 2 h at room temperature. Then the solution was made neutral with HCl 1N. Ethanol was removed and the extraction performed with ethyl acetate (3×150 ml); the organic layers were washed with brine, dried on anhydrous MgSO$_4$, filtered and the solvent evaporated: 2-(tert-butoxycarbonyl)-4- or 5-aminophenyl hydrogen carbonate (5) was obtained (3 g; 0.010 mol; yield: 89%) as a white solid.

Synthesis of 3-(tert-butoxycarbonyl)-4- or 5-hydroxyphenyl-carbamic acid (6)

Compound (6) was obtained according the procedure reported to obtain compound (5). Yield: 91%

EXAMPLE 5

General Synthetic Procedure of 4- or 5-Amino-2-(1-carboxy-3-thiocarbamoyl-propylcarbamoyloxy)-benzoic acid (11) [Compound of Formula XXII]

4- or 5-[3-(1-Carboxy-3-thiocarbamoyl-propyl)-ureido]-2-hydroxy-benzoic acid (12)

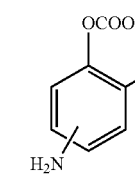 or 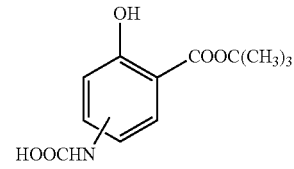

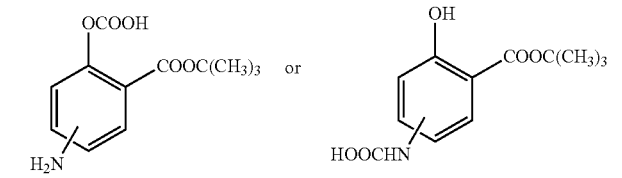

-continued
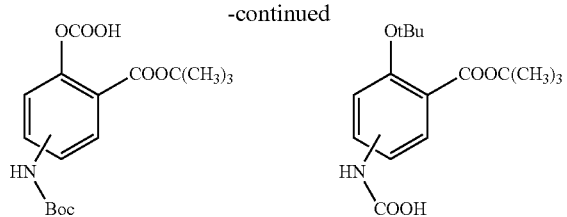
7    8
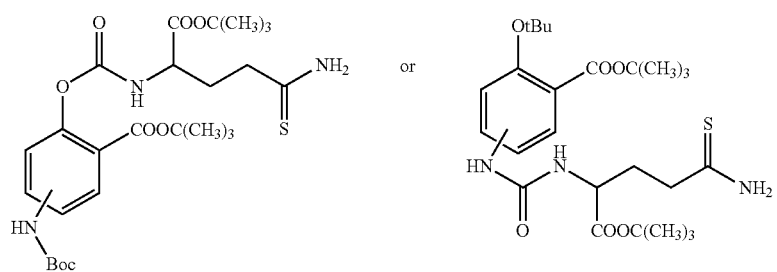
HOBt/DCC
TioGlutamine-OtBu
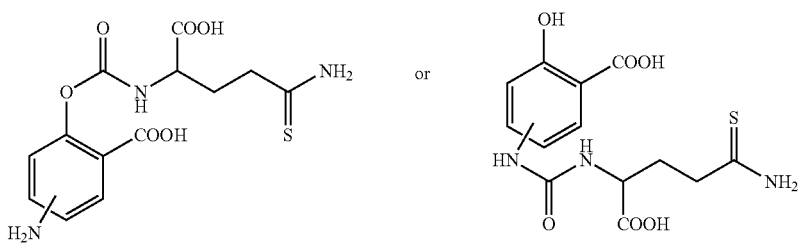
9    10
TFA
CH₂Cl₂
11    12

Synthesis of 5-thio-L-glutamine-OtBu (2)

L-glutamine-OtBu.HCl (1) (1.2 mmol; 0.3 g) and Lawesson's reagent (0.75 mmol; 0.3 g) were added to benzene (20 mL) and the mixture was heated under reflux for 15 min. The reaction was then cooled and evaporated under vacuum. The crude product was chromatographed over 100 g of silica gel eluted with mixtures of ethyl acetate and n-hexane. There was obtained 0.2 g (76% yield) of product (2) as a white solid: $^1$H NMR (CDCl$_3$) δ 1.4 (s, 9H), 1.8-2.8 (m, 5H), 4.0-4.8 (m, 3H); MS (ESI), m/z 219 (M$^+$)

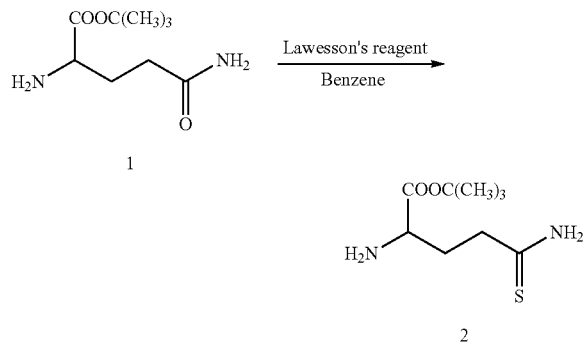

Synthesis of 2-(tert-butoxycarbonyl)-4- or 5-tert-Butoxycarbonylaminophenyl hydrogen carbonate (7)

To the solution of (5) (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3 M HCl (15 mL) was added drop wise to the residue. The precipitate is filtered, washed with water and dried. The residue was loaded on a silica gel open column and eluted with CH$_2$Cl$_2$/MeOH (9/1), from which 2-(tert-butoxycarbonyl)-4- or 5-tert-Butoxycarbonylaminophenyl hydrogen carbonate (7) was obtained (80% yield).

Synthesis of 3-(tert-butoxycarbonyl)-4- or 5-hydroxyphenyl-carbamic acid (8)

Compound 6 (12.0 mmol), conc. H$_2$SO$_4$ (6.0 mmol), and DCM (100 mL) were stirred under isobutylene gas (5 psi) for 6 h at room temperature. The solution was washed with cold 10% NaHCO$_3$ (2×100 mL) and brine (100 mL), dried (Na$_2$SO$_4$) and evaporated. The residue was dissolved in 1:1 MeOH/CCl$_4$ (400 mL), washed with water (300 mL), and then extracted with 1:1 MeOH/water (2×200 mL). The extract was dried (Na$_2$SO$_4$) and evaporated to a white solid (8), which was recrystallized by DCM/hexane (83% yield).

Synthesis of 4- or 5-Amino-2-(1-carboxy-3-thiocarbamoyl-propylcarbamoyloxy)-benzoic acid (11)

To the solution of (7) (3.0 mmol) in 50 mL of dimethylformamide, hydroxybenzotriazole (3.3 mmol) and DCC (3.3 mmol) were added with stirring at 0° C. for 1 h. To the reaction mixture, 2-amino-4-thiocarbamoyl-butyric acid tert-butyl ester (3.0 mmol) and triethylamine (3.0 mmol) were added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous MgSO$_4$, filtered and the solvent evaporated. The crude intermediate (9) was treated with a solution of 40% TFA in CH$_2$Cl$_2$. After 2 h the solvent was removed to obtain compound (11) as a crude residue. The residue was loaded on a silica gel open column and eluted with CH$_2$Cl$_2$/MeOH (8/2), from which 4- or 5-Amino-2-(1-carboxy-3-thiocarbamoyl-propylcarbamoyloxy)-benzoic acid (11) was obtained (45% yield), Compound of Formula XXII.

Synthesis of 4- or 5-[3-(1-Carboxy-3-thiocarbamoyl-propyl)-ureido]-2-hydroxy-benzoic acid (12)

Compound (12) was obtained according the procedure reported to obtain compound (11). Yield: 38%

EXAMPLE 6

General Synthetic Procedure of

4- or 5-Amino-2-[4-(5-thioxo-5H-[1,2]dithiol-3-yl)-phenoxycarbonyloxy]-benzoic acid (15) [Compound of Formula IV]

2-Hydroxy-4- or 5-[4-(5-thioxo-5H-[1,2]dithiol-3-yl)-phenoxycarbonylamino]-benzoic acid (16) [Compound of Formula V]

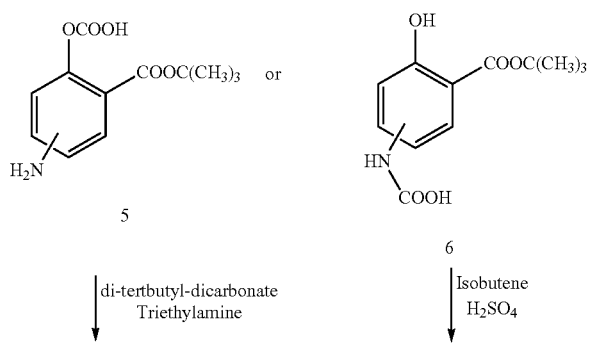

-continued
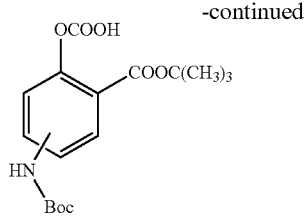
7
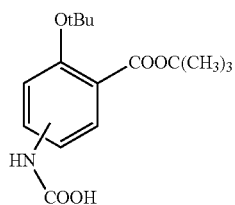
8
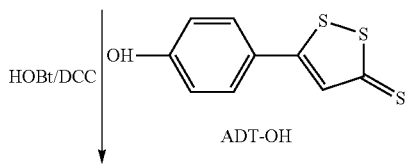
HOBt/DCC  ADT-OH
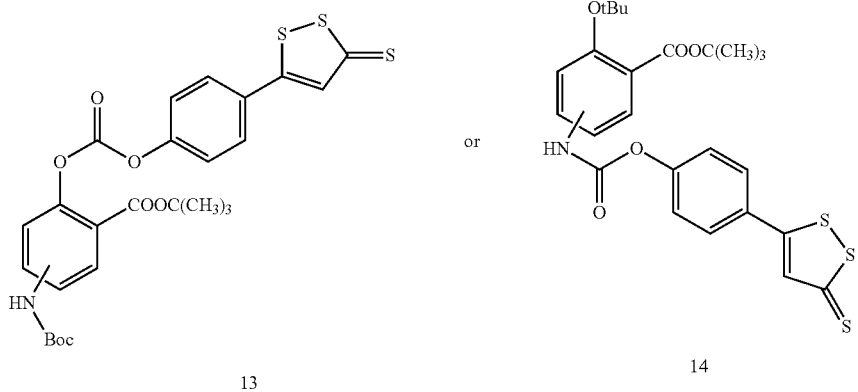
13  or  14
TFA
CH₂Cl₂
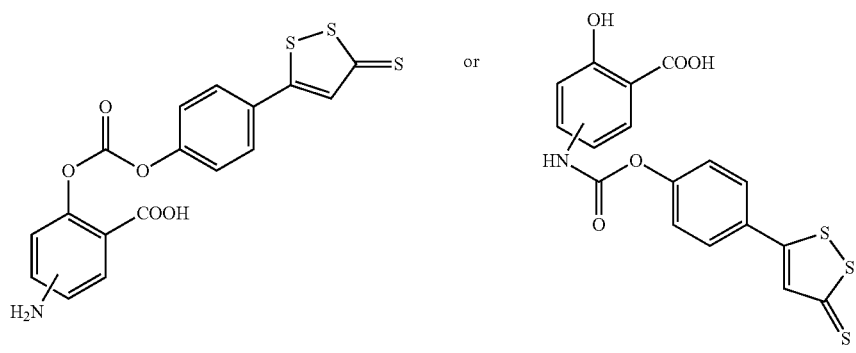
15  or  16

Synthesis of 5-p-hydroxyphenyl-1,2-dithione-3-thione (ADT-OH)

Anethole (1) (32.5 g; 0.21 mol) and sulphur (45 g; 1.40 mol) were heated in dimethylformamide (250 ml) for 8 hr; the residue after removal of solvent was almost completely soluble in toluene. An attempt to extract the toluene liquors with 2 N-aqueous sodium hydroxide, gave a precipitate of an orange solid (8.5 g). m.p. over 300° C. This product was dissolved in boiling water and gave an orange precipitate (2) after addition of hydrochloric acid (Yield 50%), m.p. 188-189° C. $^1$H NMR (DMSO) δ 6.86 (d, 2H), 7.68 (s, 1H), 7.75 (d, 2H), 10.51 (s, —OH); MS (ESI), m/z 225 (M$^-$).

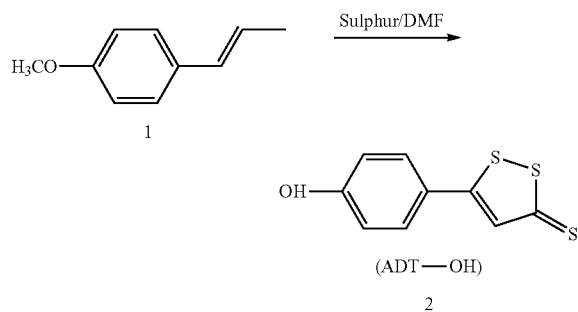

Synthesis of 2-(tert-butoxycarbonyl)-4- or 5-tert-butoxycarbonylaminophenyl hydrogen carbonate (7)

To the solution of (5) (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3 M HCl (15 mL) was added drop wise to the residue. The precipitate is filtered, washed with water and dried. The residue was loaded on a silica gel open column and eluted with $CH_2Cl_2$/MeOH (9/1), from which 2-(tert-butoxycarbonyl)-4- or 5-tert-Butoxycarbonylaminophenyl hydrogen carbonate (7) was obtained (80% yield).

Synthesis of 3-(tert-butoxycarbonyl)-4- or 5-hydroxyphenyl-carbamic acid (8)

Compound (6) (12.0 mmol), concentrated $H_2SO_4$ (6.0 mmol), and DCM (100 mL) were stirred under isobutene gas (5 psi) for 6 h at room temperature. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (8), which was recrystallized by DCM/hexane (83% yield).

Synthesis of 4- or 5-Amino-2-[4-(5-thioxo-5H-[1,2]dithiol-3-yl)-phenoxycarbonyloxy]-benzoic acid (15)

To the solution of (7) (3.0 mmol) in 50 mL of dimethylformamide, hydroxybenzotriazole (3.3 mmol) and DCC (3.3 mmol) were added with stirring at 0° C. for 1 h. To the reaction mixture, 5-p-hydroxyphenyl-1,2-dithione-3-thione (ADT-OH) (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude intermediate (13) was treated with a solution of 40% TFA in $CH_2Cl_2$. After 2 h the solvent was removed to obtain compound (15) as a crude residue. The residue was loaded on a silica gel open column and eluted with $CH_2Cl_2$/MeOH (8/2), from which 4- or 5-Amino-2-[4-(5-thioxo-5H-[1,2]dithiol-3-yl)-phenoxycarbonyloxy]-benzoic acid (15) was obtained (45% yield), compound of Formula IV.

Synthesis of 2-Hydroxy-4- or 5-[4-(5-thioxo-5H-[1,2]dithiol-3-yl)-phenoxycarbonylamino]-benzoic acid (16)

Compound (16), compound of Formula V, was obtained according the procedure reported to obtain compound (15). Yield: 38%

EXAMPLE 7

General Synthetic Procedure of 4- or 5-Amino-2-{4-[4-(4-hydroxy-phenyl)-2,4-dithioxo-2λ$^5$,4λ$^5$-[1,3,2,4]dithiadiphosphetan-2-yl]-phenoxycarbonyloxy}-benzoic acid (19) [Compound of Formula XIV]

2-Hydroxy-4- or 5-{4-[4-(4-hydroxy-phenyl)-2,4-dithioxo-2λ$^5$,4λ$^5$-[1,3,2,4]dithiadiphosphetan-2-yl]-phenoxycarbonylamino}-benzoic acid (20) [Compound of Formula XIII]

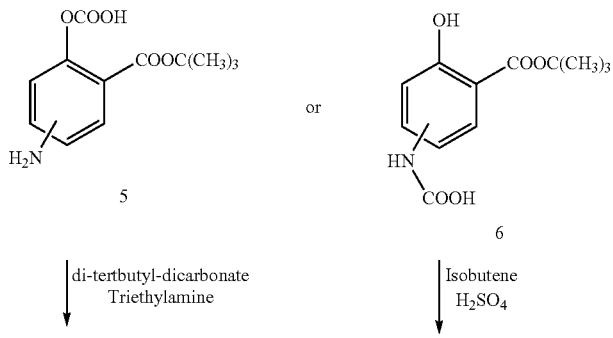

-continued
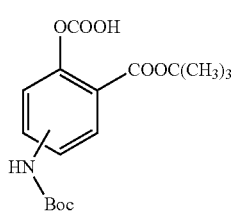
7
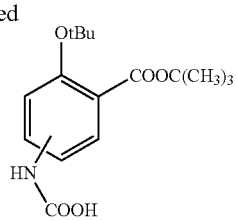
8
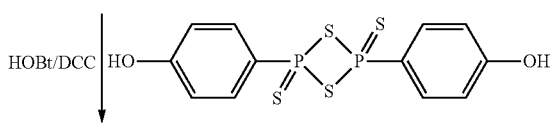
HOBt/DCC
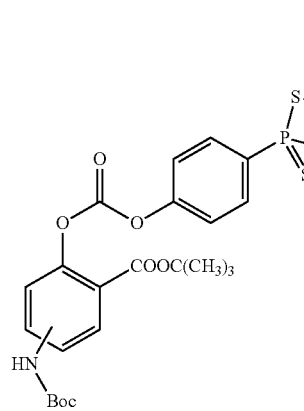
17
or
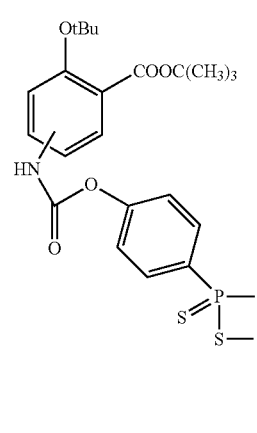
18
TFA
CH$_2$Cl$_2$
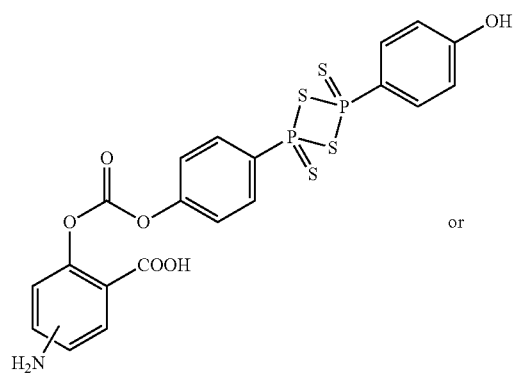
19
or
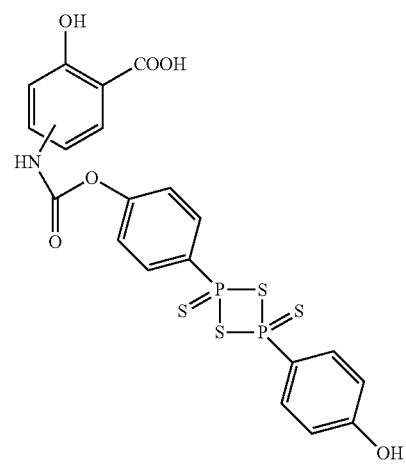
20

Synthesis of (p-hydroxyphenyl)dithiophosphonic anhydride

Red P (4 g; 0.129 mol), S (4 g; 0.125 mol) and PhOH (4 g; 0.042 mol) were heated for 5.5 hr at 155-158° C.; the reaction mixture was cooled at room temperature and a precipitate was collected (5.5 g 34% yield). m.p. 224-226° C. The NMR and MS analysis are consistent with p-hydroxyphenyl dithiophosphonic anhydride.

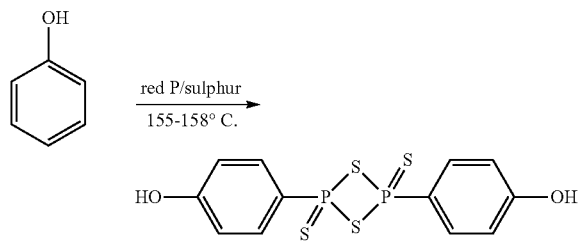

Synthesis of 2-(tert-butoxycarbonyl)-4- or 5-tert-butoxycarbonylaminophenyl hydrogen carbonate (7)

To the solution of (5) (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3 M HCl (15 mL) was added drop wise to the residue. The precipitate is filtered, washed with water and dried. The residue was loaded on a silica gel open column and eluted with $CH_2Cl_2$/MeOH (9/1), from which 2-(tert-butoxycarbonyl)-4- or 5-tert-Butoxycarbonylaminophenyl hydrogen carbonate (7) was obtained (80% yield).

Synthesis of 3-(tert-butoxycarbonyl)-4- or 5-hydroxyphenyl-carbamic acid (8)

Compound (6) (12.0 mmol), concentrated $H_2SO_4$ (6.0 mmol), and DCM (100 mL) were stirred under isobutene gas (5 psi) for 6 h at room temperature. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (8), which was recrystallized by DCM/hexane (83% yield).

Synthesis of 4- or 5-Amino-2-{4-[4-(4-hydroxy-phenyl)-2,4-dithioxo-2$\lambda^5$,4$\lambda^5$-[1,3,2,4]dithiadiphosphetan-2-yl]-phenoxycarbonyloxy}-benzoic acid (19)

To the solution of (7) (3.0 mmol) in 50 mL of dimethylformamide, hydroxybenzotriazole (3.3 mmol) and DCC (3.3 mmol) were added with stirring at 0° C. for 1 h. To the reaction mixture, p-hydroxyphenyldithiophosphonic anhydride (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude intermediate (17) was treated with a solution of 40% TFA in $CH_2Cl_2$. After 2 h the solvent was removed to obtain compound (19) as a crude residue. The residue was loaded on a silica gel open column and eluted with $CH_2Cl_2$/MeOH (8/2), from which 4- or 5-Amino-2-{4-[4-(4-hydroxy-phenyl)-2,4-dithioxo-2□$^5$, 4□$^5$-[1,3,2,4]dithiadiphosphetan-2-yl]-phenoxycarboyloxy}-benzoic acid (19) was obtained (65% yield), compound of Formula XIV.

Synthesis of 2-Hydroxy-4- or 5-{4-[4-(4-hydroxy-phenyl)-2,4-dithioxo-2$\lambda^5$,4$\lambda^5$-[1,3,2,4]dithiadiphosphetan-2-yl]-phenoxycarbonylamino}-benzoic acid (20)

Compound (20), a compound of Formula XIII, was obtained according the procedure reported to obtain compound (19). Yield: 48%

EXAMPLE 8

General synthetic procedure of 4- or 5-Amino-2-(4-thiocarbamoyl-phenoxycarbonyloxy)-benzoic acid (23) [Compound of Formula XXVIII]

2-Hydroxy-4- or 5-(4-thiocarbamoyl-phenoxycarbonylamino)-benzoic acid (24) [Compound of Formula XXIX]

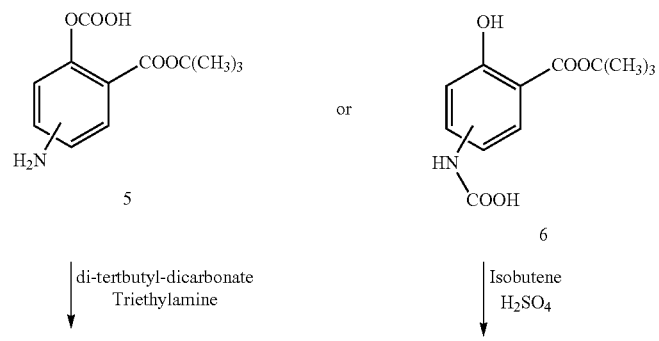

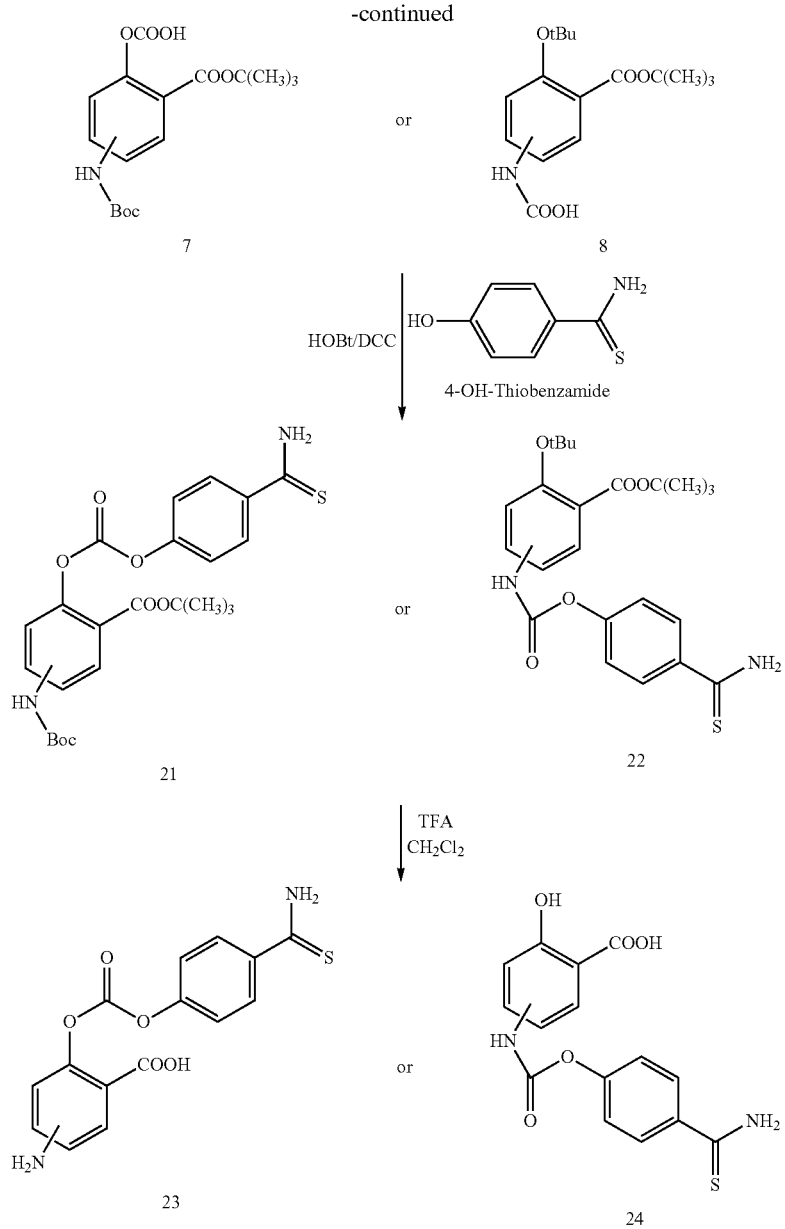

Synthesis of 2-(tert-butoxycarbonyl)-4- or 5-tert-butoxycarbonylaminophenyl hydrogen carbonate (7)

To the solution of (5) (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3 M HCl (15 mL) was added drop wise to the residue. The precipitate is filtered, washed with water and dried. The residue was loaded on a silica gel open column and eluted with $CH_2Cl_2$/MeOH (9/1), from which 2-(tert-butoxycarbonyl)-4- or 5-tert-Butoxycarbonylaminophenyl hydrogen carbonate (7) was obtained (80% yield).

Synthesis of 3-(tert-butoxycarbonyl)-4- or 5-hydroxyphenyl-carbamic acid (8)

Compound (6) (12.0 mmol), concentrated $H_2SO_4$ (6.0 mmol), and DCM (100 mL) were stirred under isobutene gas (5 psi) for 6 h at rt. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (8), which was recrystallized by DCM/hexane (83% yield).

Synthesis of 4- or 5-Amino-2-(4-thiocarbamoyl-phenoxycarbonyloxy)-benzoic acid (23)

To the solution of (7) (3.0 mmol) in 50 mL of dimethylformamide, hydroxybenzotriazole (3.3 mmol) and DCC (3.3 mmol) were added with stirring at 0° C. for 1 h. To the reaction mixture, 4-hydroxy-thiobenzamide (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude intermediate (21) was treated with a solution of 40% TFA in $CH_2Cl_2$. After 2 h the solvent was removed to obtain compound (23) as a crude residue. The residue was loaded on a silica gel open column and eluted with $CH_2Cl_2$/MeOH (8/2), from which 4- or 5-Amino-2-(4-thiocarbamoyl-phenoxycarbonyloxy)-benzoic acid (23) was obtained (71% yield), compound of Formula XXVII.

Synthesis of 2-Hydroxy-4- or 5-(4-thiocarbamoyl-phenoxycarbonylamino)-benzoic acid (24)

Compound (24), compound of Formula XXIX, was obtained according the procedure reported to obtain compound (23). Yield: 68%

EXAMPLE 9

General Synthetic Procedure of 2-(4- or 5-Amino-2-hydroxy-benzoylamino)-4-thiocarbamoyl-butyric acid (6) [Compound of Formula XXI]

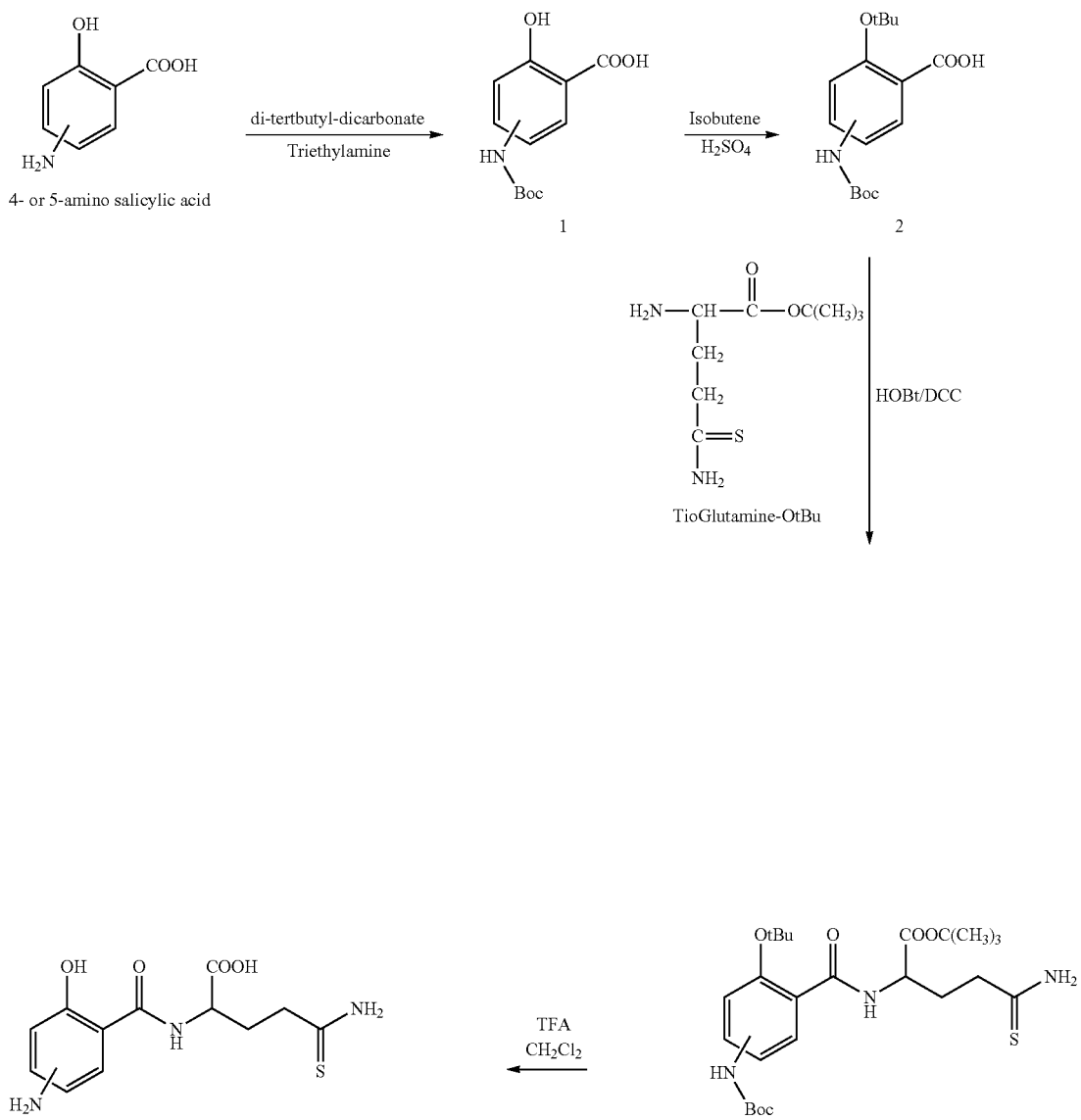

Synthesis of 5-thio-L-glutamine-OtBu (2)

L-glutamine-OtBu.HCl (1) (1.2 mmol; 0.3 g) and Lawesson's reagent (0.75 mmol; 0.3 g) were added to benzene (20 mL) and the mixture was heated under reflux for 15 min. The reaction was then cooled and evaporated under vacuum. The crude product was chromatographed over 100 g of silica gel eluted with mixtures of ethyl acetate and n-hexane. There was obtained 0.2 g (76% yield) of product (2) as a white solid: $^1$H NMR (CDCl$_3$) δ 1.4 (s, 9H), 1.8-2.8 (m, 5H), 4.0-4.8 (m, 3H); MS (ESI), m/z 219 (M$^+$).

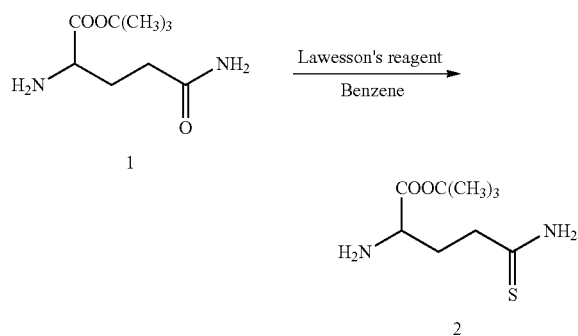

Synthesis of 4- or 5-tert-Butoxycarbonylamino-2-hydroxy-benzoic acid (1)

To the solution of 4- or 5-amino salicylic acid (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3M HCl (15 mL), was added drop wise to the residue. The precipitate is filtered, washed with water and dried. The residue was loaded on a silica gel open column and eluted with CH$_2$Cl$_2$/MeOH (9/1), from which 4- or 5-tert-Butoxycarbonylamino-2-hydroxy-benzoic acid (1) was obtained (80% yield).

Synthesis of 4- or 5-tert-Butoxycarbonylamino-2-tert-butoxy-benzoic acid (2)

Compound (1) (12.0 mmol), conc. H$_2$SO$_4$ (6.0 mmol), and DCM (100 mL) were stirred under isobutylene gas (5 psi) for 6 h at rt. The solution was washed with cold 10% NaHCO$_3$ (2×100 mL) and brine (100 mL), dried (Na$_2$SO$_4$) and evaporated. The residue was dissolved in 1:1 MeOH/CCl$_4$ (400 mL), washed with water (300 mL), and then extracted with 1:1 MeOH/water (2×200 mL). The extract was dried (Na$_2$SO$_4$) and evaporated to a white solid (2), which was recrystallized by DCM/hexane (83% yield).

Synthesis of 2-(4- or 5-amino-2-hydroxy-benzoylamino)-4-thiocarbamoyl-butyric acid (6)

To the solution of 4- or 5-tert-butoxycarbonylamino-2-tert-butoxy-benzoic acid (2) (3.0 mmol) in 50 mL of dimethylformamide, hydroxybenzotriazole (3.3 mmol) and DCC (3.3 mmol) were added with stirring at 0° C. for 1 h. To the reaction mixture, 2-amino-4-thiocarbamoyl-butyric acid tert-butyl ester (3.0 mmol) and triethylamine (3.0 mmol) were added and stirred mechanically for 3 h at 0° C. and 72 h at room temperature. After filtration, the filtrate was evaporated under reduced pressure to remove the solvent. The oily residue thus obtained was dissolved in ethyl acetate; the organic layers were washed with brine, dried on anhydrous MgSO$_4$, filtered and the solvent evaporated. The crude intermediate (5) was treated with a solution of TFA (40%) in CH$_2$Cl$_2$. After 2 h the solvent was removed to obtain compound (6) as a crude residue. The residue was loaded on a silica gel open column and eluted with CH$_2$Cl$_2$/MeOH (8/2), from which 2-(4- or 5-Amino-2-hydroxy-benzoylamino)-4-thiocarbamoyl-butyric acid (6), compound of Formula XXI, was obtained (80% yield). MS (ESI), m/z 298 (M$^+$).

EXAMPLE 10

General Synthetic Procedure of 4- or 5-Amino-2-hydroxy-benzoic acid 4-thiocarbamoyl-phenyl ester (8) [Compound of Formula XXVII]

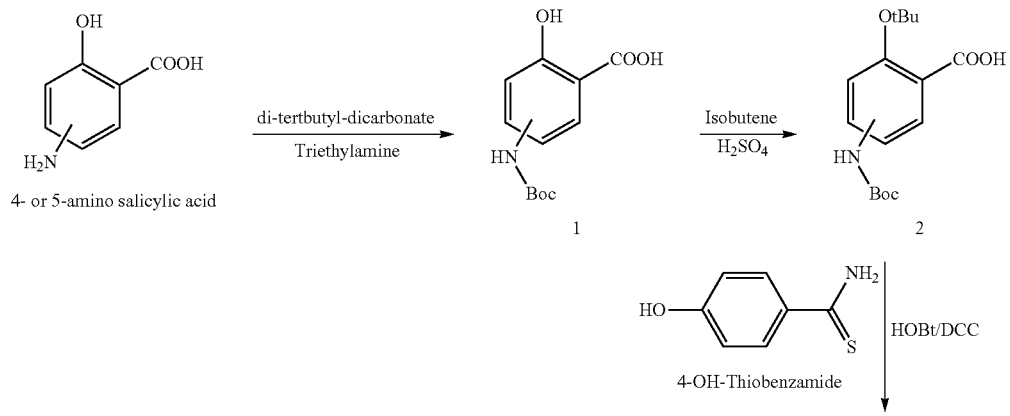

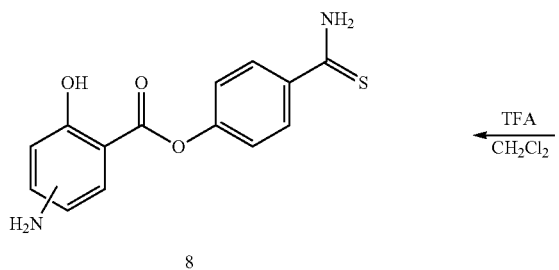
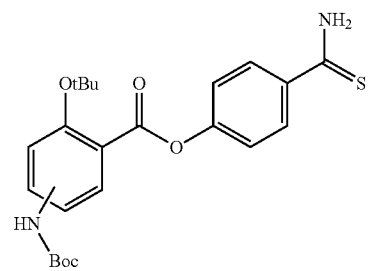

Synthesis of 4- or 5-tert-Butoxycarbonylamino-2-hydroxy-benzoic acid (1)

To the solution of 4- or 5-amino salicylic acid (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3M HCl (15 mL) was added drop wise to the residue. The precipitate is filtered, washed with water and dried. The residue was loaded on a silica gel open column and eluted with $CH_2Cl_2$/MeOH (9/1), from which 4- or 5-tert-Butoxycarbonylamino-2-hydroxy-benzoic acid (1) was obtained (80% yield).

Synthesis of 4- or 5-tert-Butoxycarbonylamino-2-tert-butoxy-benzoic acid (2)

Compound (1) (12.0 mmol), conc. $H_2SO_4$ (6.0 mmol), and DCM (100 mL) were stirred under isobutylene gas (5 psi) for 6 h at rt. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (2), which was recrystallized by DCM/hexane (83% yield).

Synthesis of 4- or 5-Amino-2-hydroxy-benzoic acid 4-thiocarbamoyl-phenyl ester (8)

To the solution of 4- or 5-tert-butoxycarbonylamino-2-hydroxy-benzoic acid (2) (3.0 mmol) in 50 mL of dimethyl-formamide, hydroxybenzotriazole (3.3 mmol) and DCC (3.3 mmol) were added with stirring at 0° C. for 1 h. To the reaction mixture, 4-hydroxythiobenzamide (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude intermediate (7) was treated with a solution of 40% TFA in $CH_2Cl_2$. After 2 h the solvent was removed to obtain compound (8) as a crude residue. The residue was loaded on a silica gel open column and eluted with $CH_2Cl_2$/MeOH (8/2), from which 4- or 5-Amino-2-hydroxy-benzoic acid 4-thiocarbamoylphenyl ester (8), compound of Formula XXVII, was obtained (48% yield).

EXAMPLE 11

General Synthetic Procedure of 4- or 5-Amino-2-hydroxy-benzoic acid 4-[4-(4-hydroxy-phenyl)-2,4-dithioxo-$2\lambda^5,4\lambda^5$-[1,3,2,4]dithiadiphosphetan-2-yl]-phenyl ester (10) [Compound of Formula XVII]

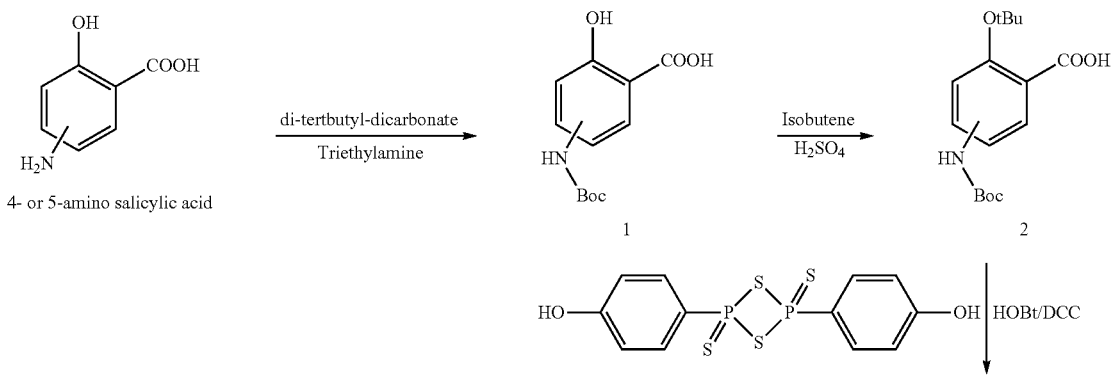

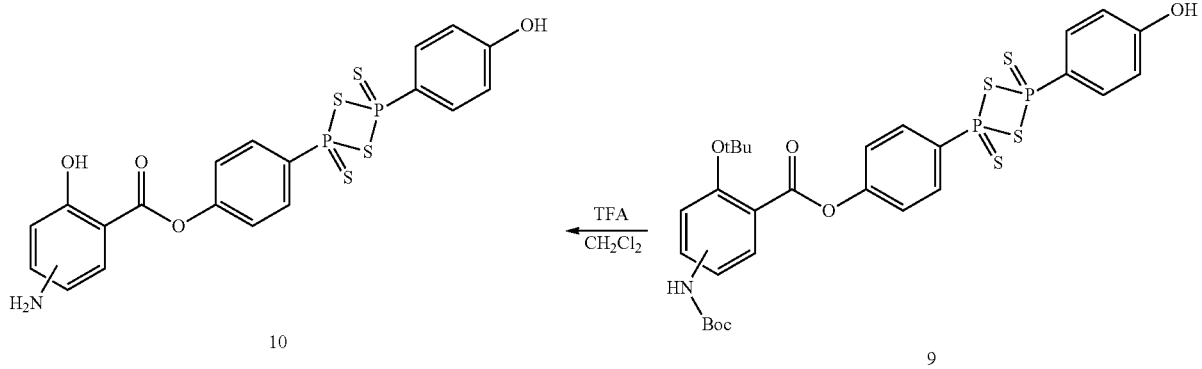

Synthesis of (p-hydroxyphenyl)dithiophosphonic anhydride

Red P (4 g; 0.129 mol), S (4 g; 0.125 mol) and PhOH (4 g; 0.042 mol) were heated for 5.5 hr at 155-158° C.; the reaction mixture was cooled at room temperature and a precipitate was collected (5.5 g, 34% yield). m.p. 224-226° C. The NMR and MS analysis are consistent with p-hydroxyphenyl dithiophosphonic anhydride.

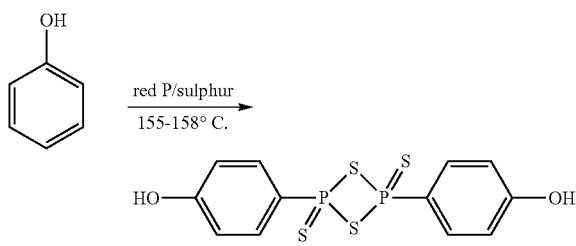

Synthesis of 4- or 5-tert-Butoxycarbonylamino-2-hydroxy-benzoic acid (1)

To the solution of 4- or 5-amino salicylic acid (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3M HCl (15 mL) was added drop wise to the residue. The precipitate is filtered, washed with water and dried. The residue was loaded on a silica gel open column and eluted with $CH_2Cl_2$/MeOH (9/1), from which 4- or 5-tert-Butoxycarbonylamino-2-hydroxy-benzoic acid (1) was obtained (80% yield).

Synthesis of 4- or 5-tert-Butoxycarbonylamino-2-tert-butoxy-benzoic acid (2)

Compound (1) (12.0 mmol), conc. $H_2SO_4$ (6.0 mmol), and DCM (100 mL) were stirred under isobutylene gas (5 psi) for 6 h at rt. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (2), which was recrystallized by DCM/hexane (83% yield).

Synthesis of 4- or 5-Amino-2-hydroxy-benzoic acid 4-[4-(4-hydroxy-phenyl)-2,4-dithioxo-$2\lambda^5,4\lambda^5$-[1,3,2,4]dithiadiphosphetan-2-yl]-phenyl ester (10)

To the solution of 4- or 5-tert-butoxycarbonylamino-2-tert-butoxy-benzoic acid (2) (3.0 mmol) in 50 mL of dimethylformamide, hydroxybenzotriazole (3.3 mmol) and DCC (3.3 mmol) were added with stirring at 0° C. for 1 h. To the reaction mixture, p-hydroxyphenyldithiophosphonic anhydride (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude intermediate 9 was treated with a solution of TFA (40%) in $CH_2Cl_2$. After 2 h the solvent was removed to obtain compound 10 as a crude residue. The residue was loaded on a silica gel open column and eluted with $CH_2Cl_2$/MeOH (8/2), from which 4- or 5-amino-2-hydroxy-benzoic acid 4-[4-(4-hydroxy-phenyl-2,4-dithioxo-$2\lambda^5,4\lambda^5$-[1,3,2,4]dithiadiphosphetan-2-yl]-phenyl ester (10), compound of Formula XVII, was obtained (73% yield).

Synthesis of 4- or 5-amino-2-hydroxy-benzoic acid mercaptoethanesulfonate (2)

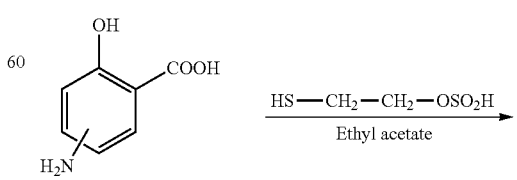

-continued

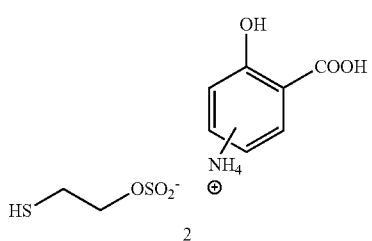

A mixture of sulfurous acid 2-mercapto-ethyl ester (0.1 mol) in 100 ml of ethyl acetate was added to the 4- or 5-aminosalicylic acid (1) (0.1 mole in 100 ml of ethyl acetate) solution in 30-45 min at 20-25° C. under an inert atmosphere. Then the mixture was stirred at 0-5° C. for 1 hour and filtered to give 4- or 5-amino-2-hydroxy-benzoic acid mercaptoethanesulfonate (2) (yield: 98%).

EXAMPLE 12

Synthesis of 4 or 5-amino-2-(2-Acetylamino-3-mercapto-propionyloxy)-benzoic acid (3) [Compound of Formula XII]

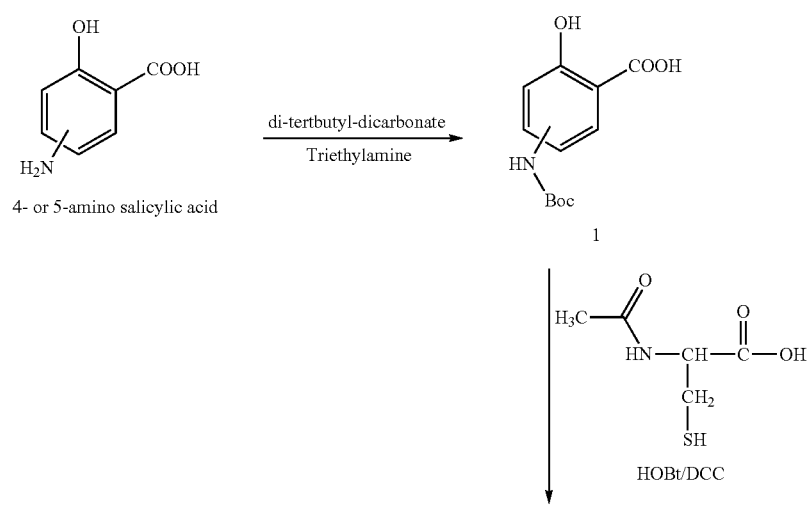

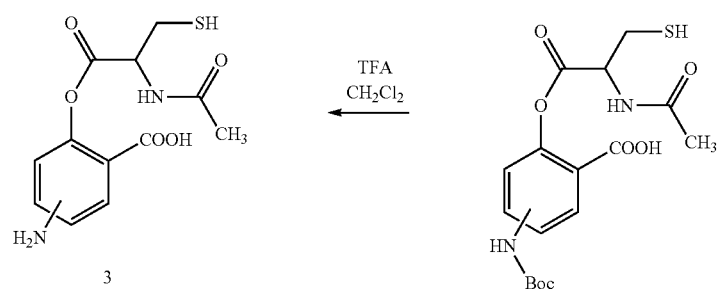

Synthesis of 4- or 5-tert-Butoxycarbonylamino-2-hydroxy-benzoic acid (1)

To the solution of 4- or 5-amino salicylic acid (10.0 mmol) in 25 mL of dioxane and 12.5 mL of water, triethylamine (15.0 mmol) and di-tertbutyl-dicarbonate (15.0 mmol) were added with stirring at 0° C. for ½ h. The reaction mixture was stirred mechanically for 24 h at room temperature. After evaporation of the solvent, 3 M HCl (15 mL) was added drop wise to the residue. The precipitate is filtered, washed with water and dried. The residue was loaded on a silica gel open column and eluted with $CH_2Cl_2$/MeOH (9/1), from which 4- or 5-tert-Butoxycarbonylamino-2-hydroxy-benzoic acid (1) was obtained (80% yield).

Synthesis of 4 or 5-amino-2-(2-Acetylamino-3-mercapto-propionyloxy)-benzoic acid (3)

To the solution of 2-acetylamino-3-mercapto-propionic acid (3.0 mmol) in 50 mL of dimethylformamide, hydroxybenzotriazole (3.3 mmol) and DCC (3.3 mmol) were added with stirring at 0° C. for 1 h. To the reaction mixture, 4- or 5-tert-Butoxycarbonylamino-2-hydroxy-benzoic acid (2) (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude intermediate (2) was treated with a solution of TFA (40%) in $CH_2Cl_2$. After 2 h the solvent was removed to obtain compound (3) as a crude residue. The residue was loaded on a silica gel open column and eluted with $CH_2Cl_2$/MeOH (8/2), from which 4 or 5-amino-2-(2-Acetylamino-3-mercapto-propionyloxy)-benzoic acid (3), compound of Formula XII, was obtained (52% yield).

EXAMPLE 13

Synthesis of 4 or 5-Amino-2-hydroxy-benzoic acid anhydride with 2-Acetylamino-3-mercapto-propionic acid (4) [Compound of Formula X]

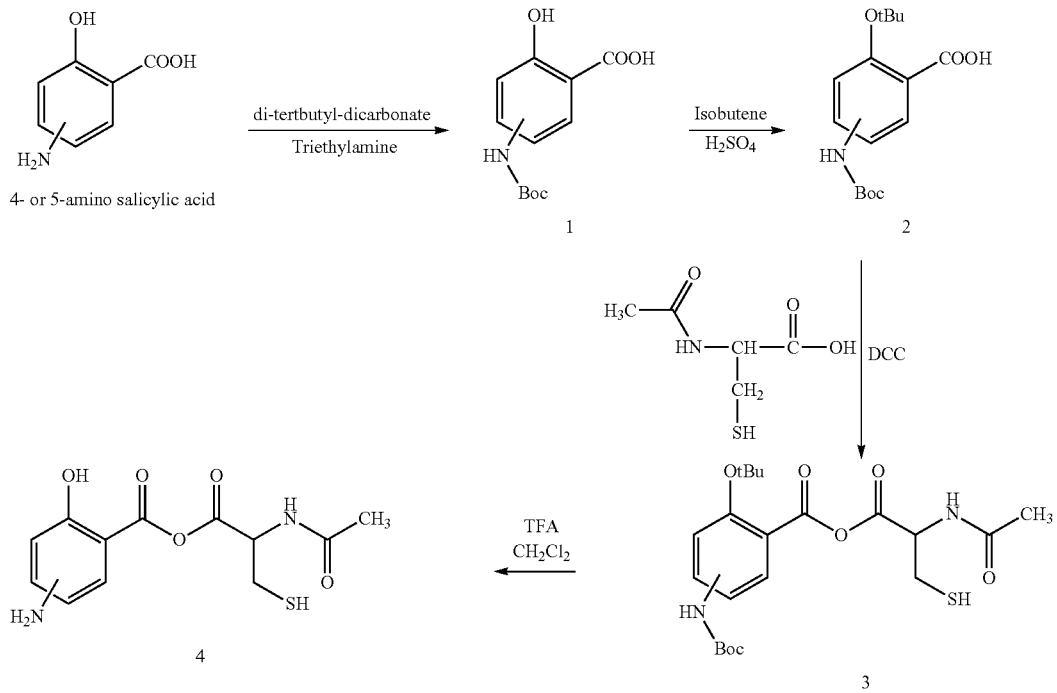

Synthesis of 4- or 5-tert-Butoxycarbonylamino-2-hydroxy-benzoic acid (1)

To the solution of 5-amino salicylic acid (10.0 mmol) in 25 mL of dioxane and 12.5 mL of water, triethylamine (15.0 mmol) and di-tertbutyl-dicarbonate (15.0 mmol) were added with stirring at 0° C. for ½ h. The reaction mixture was stirred mechanically for 24 h at room temperature. After evaporation of the solvent, 3M HCl (15 mL), was added drop wise to the residue. The precipitate is filtered, washed with water and dried. The residue was loaded on a silica gel open column and eluted with $CH_2Cl_2$/MeOH (9/1), from which 4- or 5-tert-Butoxycarbonylamino-2-hydroxy-benzoic acid (1) was obtained (80% yield).

Synthesis of 4- or 5-tert-Butoxycarbonylamino-2-tert-butoxy-benzoic acid (2)

Compound (1) (12.0 mmol), conc. $H_2SO_4$ (6.0 mmol), and DCM (100 mL) were stirred under isobutylene gas (5 psi) for 6 h at rt. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (2), which was recrystallized by DCM/hexane (83% yield).

Synthesis of 4 or 5-Amino-2-hydroxy-benzoic acid anhydride with 2-Acetylamino-3-mercapto-propionic acid (4)

To the solution of 4- or 5-tert-butoxycarbonylamino-2-tert-butoxy-benzoic acid (2) (3.0 mmol) in 50 mL of dimethylformamide, DCC (3.3 mmol) was added with stirring at 0° C. for 1 h. To the reaction mixture, 2-acetylamino-3-mercapto-propionic acid (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layers were washed with brine, dried on anhydrous $MgSO_4$, filtered and the solvent evaporated. The crude intermediate (3) was treated with a solution of TFA (40%) in $CH_2Cl_2$. After 2 h the solvent was removed to obtain compound 4 as a crude residue. The residue was loaded on a silica gel open column and eluted with $CH_2Cl_2$/MeOH (8/2), from which 4 or 5-Amino-2-hydroxy-benzoic acid anhydride with 2-Acetylamino-3-mercapto-propionic acid (4), compound of Formula X, was obtained (68% yield).

EXAMPLE 14

Synthesis of 4 or 5-(2-Acetylamino-3-mercapto-propionylamino)-2-hydroxy-benzoic acid (5) [Compound of Formula XI]

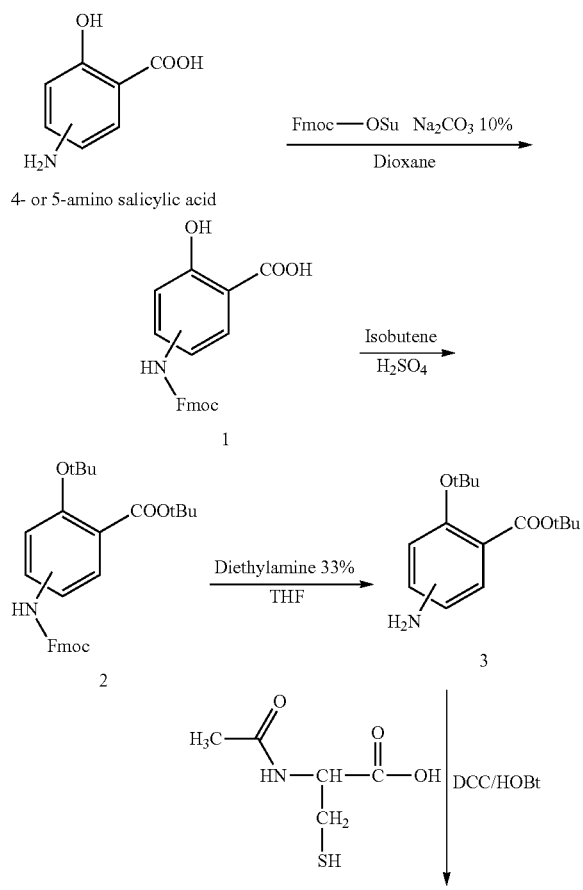

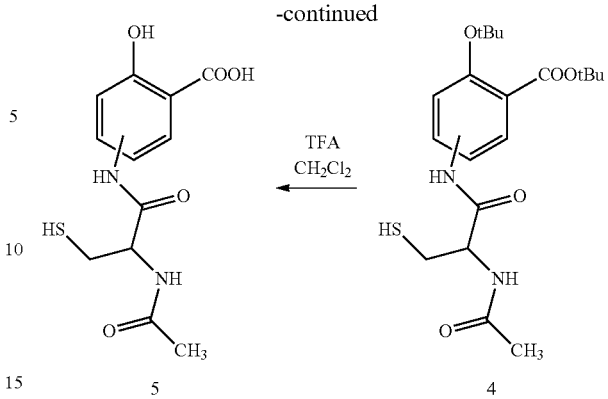

Synthesis of 4 or 5-(9H-Fluoren-9-ylmethoxycarbonylamino)-2-hydroxy-benzoic acid (1)

To the solution of 4- or 5-amino salicylic acid (10.0 mmol) in 25 mL of dioxane and 12.5 mL of water, $Na_2CO_3$ 10% (15 mL) and Fmoc-OSu (15.0 mmol) were added with stirring at 0° C. for ½ h. The reaction mixture was stirred mechanically for 24 h at room temperature. After evaporation of the solvent, 3M HCl (15 mL) was added drop wise to the residue. The precipitate is filtered, washed with water and dried. The residue was loaded on a silica gel open column and eluted with $CH_2Cl_2$/MeOH (9/1), from which 4- or 5-tert-Butoxycarbonylamino-2-hydroxy-benzoic acid (1) was obtained (90% yield).

Synthesis of 4 or 5-Amino-2-tert-butoxy-benzoic acid tert-butyl ester (3)

Compound (1) (12.0 mmol), conc. $H_2SO_4$ (6.0 mmol), and DCM (100 mL) were stirred under isobutylene gas (7 psi) for 24 h at room temperature. The solution was washed with cold 10% $NaHCO_3$ (2×100 mL) and brine (100 mL), dried ($Na_2SO_4$) and evaporated. The residue was dissolved in 1:1 $MeOH/CCl_4$ (400 mL), washed with water (300 mL), and then extracted with 1:1 MeOH/water (2×200 mL). The extract was dried ($Na_2SO_4$) and evaporated to a white solid (2). The crude intermediate (2) was treated with a solution of diethylamine (33%) in THF. After 2 h the solvent was removed to obtain compound (3) as a crude residue. The residue was loaded on a silica gel open column and eluted with $CH_2Cl_2$/MeOH (8/2), from which 4 or 5-Amino-2-tert-butoxy-benzoic acid tert-butyl ester (3) was obtained (67% yield).

Synthesis of 4 or 5-(2-Acetylamino-3-mercapto-propionylamino)-2-hydroxy-benzoic acid (5)

To the solution of 2-acetylamino-3-mercapto-propionic acid (3.0 mmol) in 50 mL of dimethylformamide, hydroxy-benzotriazole (3.3 mmol) and DCC (3.3 mmol) were added with stirring at 0° C. for 1 h. To the reaction mixture, 4 or 5-amino-2-tert-butoxy-benzoic acid tert-butyl ester (3) (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous MgSO$_4$, filtered and the solvent evaporated. The crude intermediate 4 was treated with a solution of TFA (40%) in CH$_2$Cl$_2$. After 2 h the solvent was removed to obtain compound (5) as a crude residue. The residue was loaded on a silica gel open column and eluted with CH$_2$Cl$_2$/MeOH (8/2), from which 4 or 5-(2-Acetylamino-3-mercapto-propionylamino)-2-hydroxy-benzoic acid (5), compound of Formula XI, was obtained (78% yield).

EXAMPLE 15

Synthesis of 4 or 5-Amino-2-(2-mercapto-ethoxysulfonyloxy)-benzoic acid (3) [Compound of Formula XXXIV]

wise to the residue. The precipitate is filtered, washed with water and dried. The residue was loaded on a silica gel open column and eluted with CH$_2$Cl$_2$/MeOH (9/1), from which 4- or 5-tert-Butoxycarbonylamino-2-hydroxy-benzoic acid (1) was obtained (80% yield).

Synthesis of: 4 or 5-Amino-2-(2-mercapto-ethoxysulfonyloxy)-benzoic acid (3)

To the solution of sulfuric acid mono-(2-mercapto-ethyl) ester (3.0 mmol) in 50 mL of dimethylformamide, hydroxybenzotriazole (3.3 mmol) and DCC (3.3 mmol) were added with stirring at 0° C. for 1 h. To the reaction mixture, 4- or 5-tert-Butoxycarbonylamino-2-hydroxy-benzoic acid (2) (3.0 mmol) was added and stirred mechanically for 3 h at 0° C. and 72 h at room temperature. After filtration, the filtrate was evaporated under reduced pressure to remove the solvent.

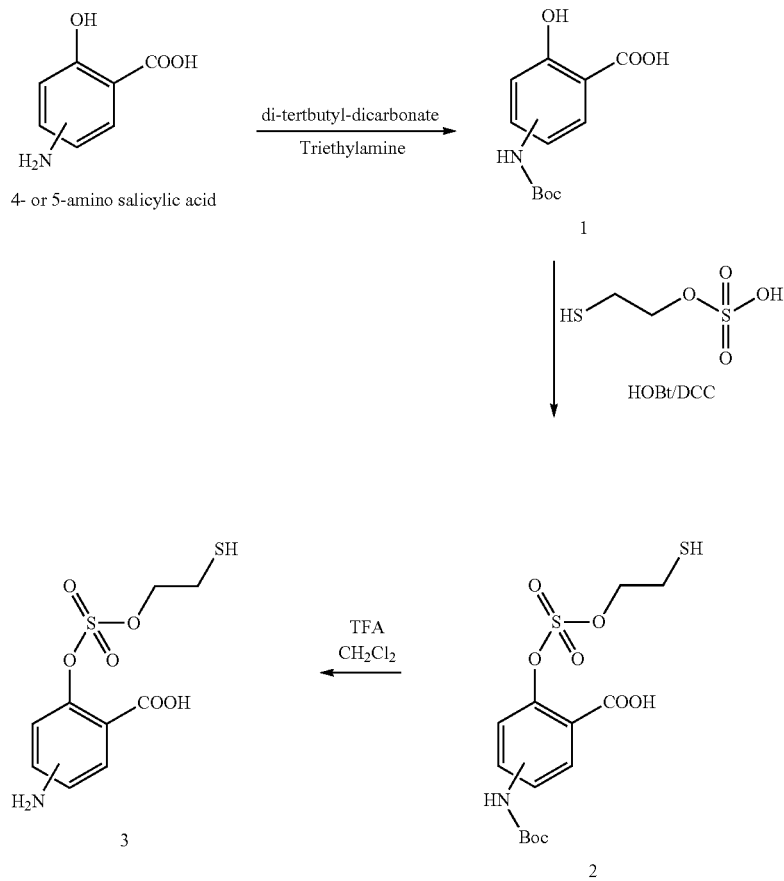

Synthesis of 4- or 5-tert-Butoxycarbonylamino-2-hydroxy-benzoic acid (1)

To the solution of 4- or 5-amino salicylic acid (10.0 mmol) in 25 mL of dioxane and 12.5 mL of water, triethylamine (15.0 mmol) and di-tertbutyl-dicarbonate (15.0 mmol) were added with stirring at 0° C. for ½ h. The reaction mixture was stirred mechanically for 24 h at room temperature. After evaporation of the solvent, 3M HCl (15 mL) was added drop The oily residue thus obtained was dissolved in ethyl acetate; the organic layer was washed with brine, dried on anhydrous MgSO$_4$, filtered and the solvent evaporated. The crude intermediate (2) was treated with a solution of TFA (40%) in CH$_2$Cl$_2$. After 2 h the solvent was removed to obtain compound 3 as a crude residue. The residue was loaded on a silica gel open column and eluted with CH$_2$Cl$_2$/MeOH (8/2), from which 4 or 5-Amino-2-(2-mercapto-ethoxysulfonyloxy)-benzoic acid (3), compound of Formula XXXIV, was obtained (57% yield).

EXAMPLE 16

Synthesis of 4 or 5-Amino-2-hydroxy-benzoic acid anhydride with Sulfuric acid mono-(2-mercapto-ethyl)ester (4) [Compound of Formula XXXIII]

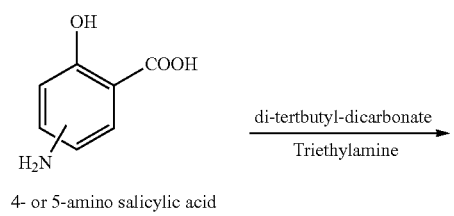

4- or 5-amino salicylic acid

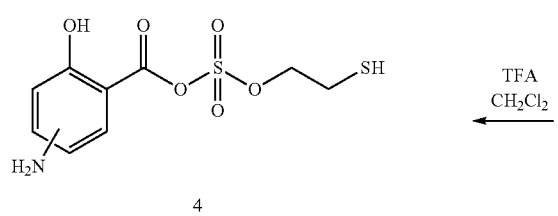

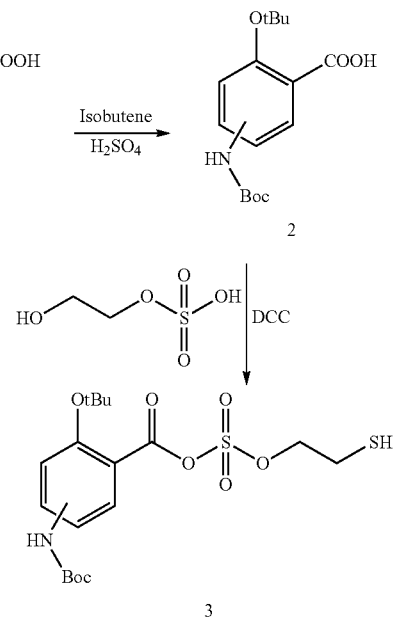

Synthesis of 4- or 5-tert-Butoxycarbonylamino-2-hydroxy-benzoic acid (1)

To the solution of 5-amino salicylic acid (10.0 mmol) in 25 mL of dioxane and 12.5 mL of water, triethylamine (15.0 mmol) and di-tertbutyl-dicarbonate (15.0 mmol) were added with stirring at 0° C. for ½ h. The reaction mixture was stirred mechanically for 24 h at room temperature. After evaporation of the solvent, 3M HCl (15 mL) was added drop wise to the residue. The precipitate is filtered, washed with water and dried. The residue was loaded on a silica gel open column and eluted with $CH_2Cl_2$/MeOH (9/1), from which 4- or 5-tert-Butoxycarbonylamino-2-hydroxy-benzoic acid (1) was obtained (80% yield).

Synthesis of 4- or 5-tert-Butoxycarbonylamino-2-tert-butoxy-benzoic acid (2)

Compound (1) (12.0 mmol), conc. $H_2SO_4$ (6.0 mmol), and DCM (100 mL) were stirred under isobutylene gas (5 psi) for 6 h at rt. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (2), which was recrystallized by DCM/hexane (83% yield).

Synthesis of 4 or 5-Amino-2-hydroxy-benzoic acid anhydride with Sulfuric acid mono-(2-mercapto-ethyl)ester (4)

To the solution of 4- or 5-tert-Butoxycarbonylamino-2-tert-butoxy-benzoic acid (2) (3.0 mmol) in 50 mL of dimethylformamide, DCC (3.3 mmol) was added with stirring at 0° C. for 1 h. To the reaction mixture, sulfuric acid mono-(2-mercapto-ethyl)ester (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layers were washed with brine, dried on anhydrous $MgSO_4$, filtered and the solvent evaporated. The crude intermediate (3) was treated with a solution of TFA (40%) in $CH_2Cl_2$. After 2 h the solvent was removed to obtain compound (4) as a crude residue. The residue was loaded on a silica gel open column and eluted with $CH_2Cl_2$/MeOH (8/2), from which 4 or 5-Amino-2-hydroxy-benzoic acid anhydride with sulfuric acid mono-(2-mercapto-ethyl)ester (4), compound of Formula XXXIII, was obtained (68% yield).

Characterization of Compounds

EXAMPLE 17

5-Amino-2-hydroxy-benzoic acid 4-(5-thioxo-5H-[1,2]dithiol-3-yl)-phenyl ester [Referred to from hereonin as Compound XXXV]

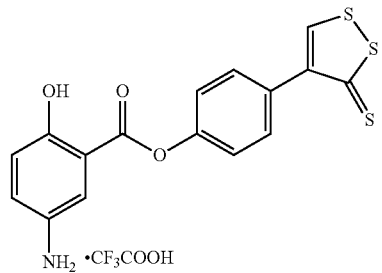

Thin layer chromatography was performed on Macherey-Nagel™ silica gel 50 plates with fluorescent indicator and the plates were visualized with UV light (254 nm). Kieselgel™ 60 was used for column chromatography. All synthetic reagents were purchased from the Aldrich-Sigma Chemical Company and were used without purification. Solvents were analytical reagent grade or higher purity and were used as supplied. Solutions were dried over $Na_2SO_4$ and a Buchi™ R-114 rotavapor was utilized for the removal of the solvents in vacuo. The structures were verified spectroscopically by proton $^1$H-NMR and $^{13}$C-NMR. Spectra were recorded on Varian Mercury Plus 400 instrument. Spectra were recorded in DMSO. The following abbreviations are used to describe peak patterns when appropriate: s (singlet), d (doublet). Chemical shifts are referred to $Me_4Si$ as internal standard. Mass spectra of the synthesized products were performed on Applayed Biosystem™ API 2000 mass spectrometry. Melting point was determined using a Kofler™ hot-stage apparatus and are uncorrected.

$^1$H NMR (DMSO) δ 7.07 (d, 2H), 7.38 (d, 2H), 7.46 (d, 2H), 7.79 (s, 1H), 7.85 (s, 1H), 8.01 (d, 2H), 10.35 (s, —OH);

$^{13}$C NMR (DMSO) δ 114.6; 119.6; 123.9; 127.7; 128.7; 129.4; 129.8; 136.1; 153.8; 158.8; 165.4; 173.2; 189.7; 216.2

MS (EI), m/e 362 ($M^+$);

m.p.: 93-95° C.

EXAMPLE 18

5-Amino-2-hydroxy-benzoic acid 4-thiocarbamoyl-phenyl ester [Referred to hereonin as Compound XXVII]

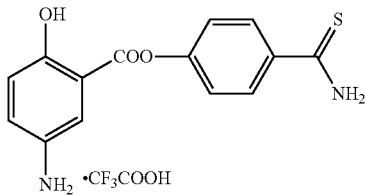

Thin layer chromatography was performed on Macherey-Nagel silica gel 50 plates with fluorescent indicator and the plates were visualized with UV light (254 nm). Kieselgel 60 was used for column chromatography. All synthetic reagents were purchased from the Aldrich-Sigma Chemical Company and were used without purification. Solvents were analytical reagent grade or higher purity and were used as supplied. Solutions were dried over $Na_2SO_4$ and a Buchi R-114 rotavapor was utilized for the removal of the solvents in vacuo. The structures were verified spectroscopically by proton $^1$H-NMR and $^{13}$C-NMR. Spectra were recorded on Varian Mercury Plus 400 instrument. Spectra were recorded in DMSO. The following abbreviations are used to describe peak patterns when appropriate: s (singlet), d (doublet). Chemical shifts are referred to $Me_4Si$ as internal standard. Mass spectra of the synthesized products were performed on Applayed Biosystem API 2000 mass spectrometry. Melting point was determined using a Kofler hot-stage apparatus and are uncorrected.

$^1$H NMR (DMSO): δ 7.03 (d, 1H), 7.31 (d, 2H), 7.32 (s, 1H), 7.71 (d, 1H), 7.97 (d, 1H), 9.55 (s, $NH_2$), 9.91 (s, $NH_2$), 10.25 (s, —OH);

$^{13}$C NMR (DMSO): δ 114.4, 119.5, 122.1, 122.7, 129.2, 129.5, 138.1, 152.1, 157.7, 165.9, 189.7, 199.7

MS (EI), m/e 289 ($M^+$);

m.p.: 193-195° C.

Testing of Compounds

EXAMPLE 19

Dose-Ranging Study of 2-hydroxy-5-amino-benzoic acid 4-(thioxo-5H-[1,2]dithiol-3-yl-phenyl ester hydrochloride (Compound XXXV)

In TNBS-Induced Colitis in Mice

A standard experimental animal model of colitis induced by intracolonic administration of 2,4,6-trinitrobenzene sulfonic acid (TNBS) to mice is used in the following example. A detailed description of this model has been published (Santucci et al. (2003) *Gastroenterology* 124:1381-94) and is incorporated herein by reference. Briefly, 6-8 week old Balb/c mice were given TNBS intracolonically at a dose of 1.5 mg in 0.1 mL of 30% ethanol. The mice were randomized to the various treatment groups (n=6 per group). Beginning one hour later and continuing every 12 h for 5 days, the mice were treated orally with vehicle (1% carboxymethylcellulose (CMC)), 5-ASA (mesalamine) (25, 50 or 75 mg/kg) or with equimolar doses of 2-hydroxy-5-amino-benzoic acid 4-(thioxo-5H-[1,2]dithiol-3-yl)-phenyl ester hydrochloride (Compound XXXV) (130 mg/kg), or with 66% (100 mg/kg), 50% (66 mg/kg) and 25% (33 mg/kg) of that dose. The mice were evaluated (blindly) on the final day of the study for the presence of diarrhea and fecal occult blood, and their body weights were measured. A "disease activity score" was calculated based on these data (0 to 4 scale, as outlined in the paper cited above). After sacrifice, a sample of the colon was excised for measurement of myeloperoxidase (MPO) activity, as a marker of granulocyte infiltration. All results were compared to those obtained with healthy mice as well.

Figure 2:
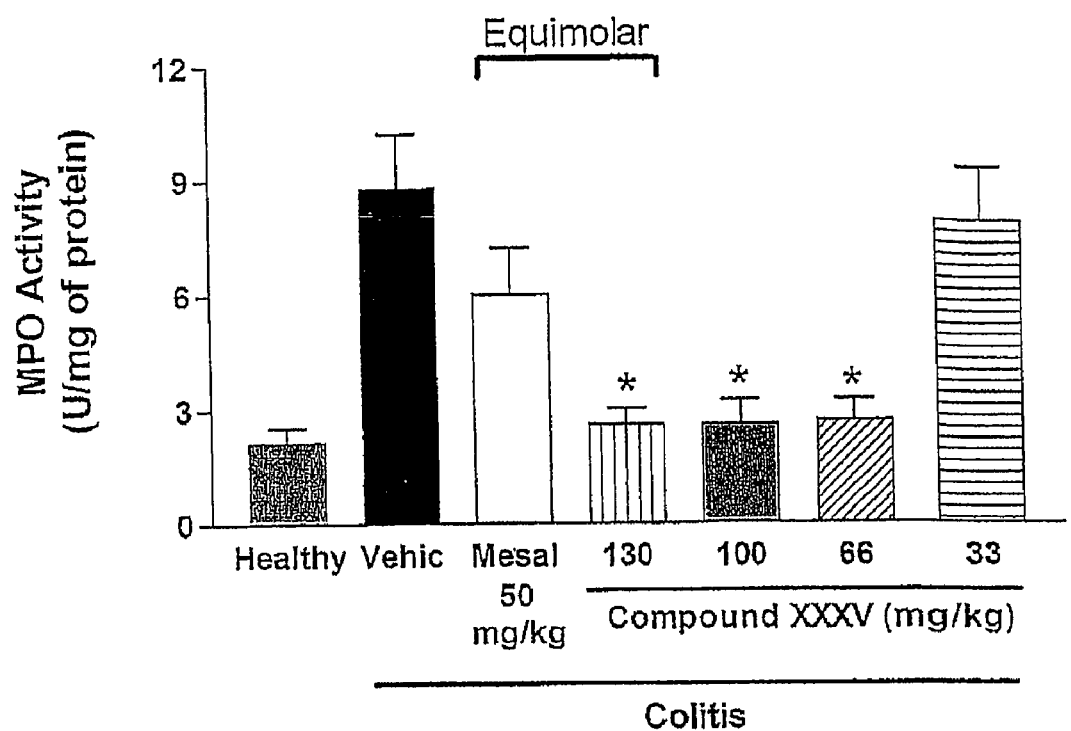
FIG. 2 shows the myeloperoxidase (MPO) activity in mice having TNBS-induced colitis after treatment with increasing doses of mesalamine and Compound XXXV of the present invention.

The results for the disease activity score and MPO activity are shown in FIG. 1 and FIG. 2, respectively. FIG. 1 shows that Compound XXXV was superior to mesalamine in reducing the activity score at equimolar doses of 50 mg/kg and 75 mg/kg. Further, as shown in FIG. 2, MPO activity was significantly reduced (almost in half) at the highest doses tested.

EXAMPLE 20

Figure 3:
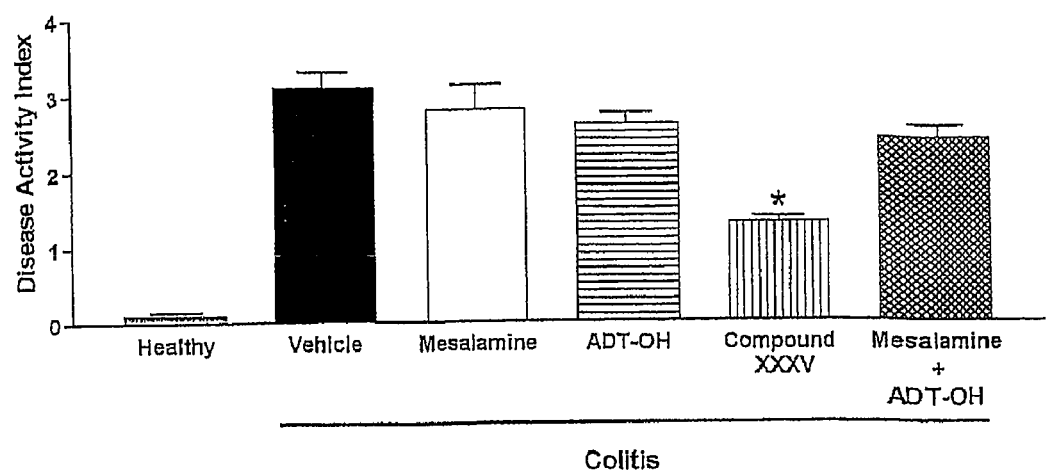
FIG. 3 shows the Disease Activity Score of mice having TNBS-induced colitis after treatment with Compound XXXV, mesalamine alone, 5-p-hydroxyphenyl-1,2-dithione-3-thione (ADT-OH) alone and a mixture of mesalamine and ADT-OH.
Figure 4:
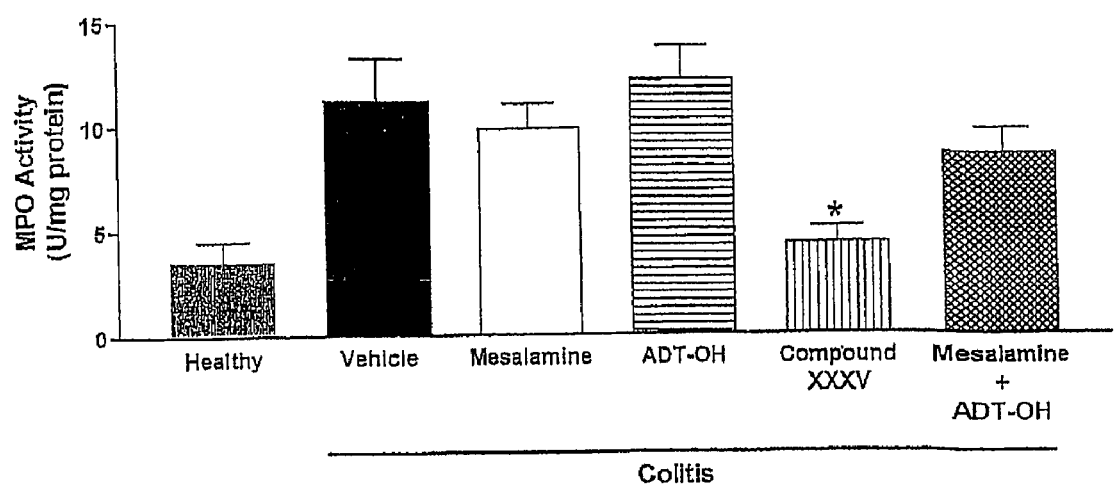
FIG. 4 shows the myeloperoxidase (MPO) activity in mice having TNBS-induced colitis after treatment with Compound XXXV, mesalamine alone, ADT-OH alone and a mixture of mesalamine and ADT-OH.

Comparison of Disease Activity Index and MPO Activity of Compound XXXV with 5-ASA (Mesalamine) Alone, (ADT-OH) Alone, and a Mixture of Mesalamine and ADT-OH FIGS. 3 and 4 show the Disease Activity Index and MPO activity, respectively, using the same experimental animal model of colitis as described above, in which Compound XXXV (130 mg/kg) was compared to equimolar doses of its two constituents, mesalamine (50 mg/kg) and 5-p-hydroxyphenyl-1,2-dithione-3-thione (ADT-OH) (80 mg/kg), and a mixture of mesalamine (50 mg/kg) and ADT-OH (80 mg/kg). *p<0.05 versus the vehicle-treated group. Each group consisted of at least 5 rats.

FIG. 3 shows that Compound XXXV is almost twice as effective as either mesalamine alone, ADT-OH alone or a mixture of mesalamine and ADT-OH in reducing disease symptoms. Further, FIG. 4 shows that Compound XXXV significantly reduced inflammation as indicated by the reduction in granulocyte infiltration (reduced MPO activity).

EXAMPLE 21

Comparison of Disease Activity Index and MPO Activity of 5-Amino-2-(4-thiocarbamoyl-phenoxycarbonyloxy)-benzoic acid (Compound XXVII)

Figure 6:
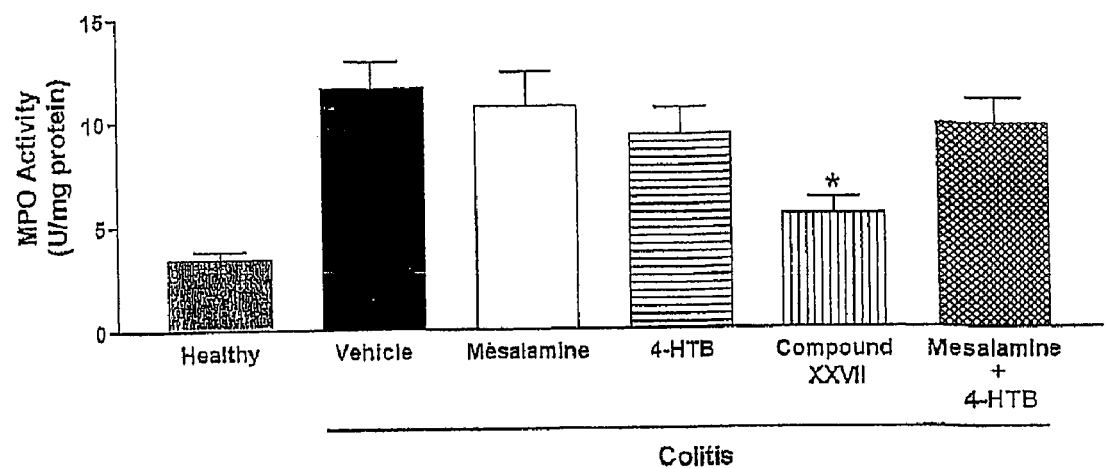
FIG. 6 shows the myeloperoxidase (MPO) activity in mice having TNBS-induced colitis after treatment with Compound XXVII, mesalamine alone, 4-HTB alone and a mixture of mesalamine and 4-HTB.
Figure 7:
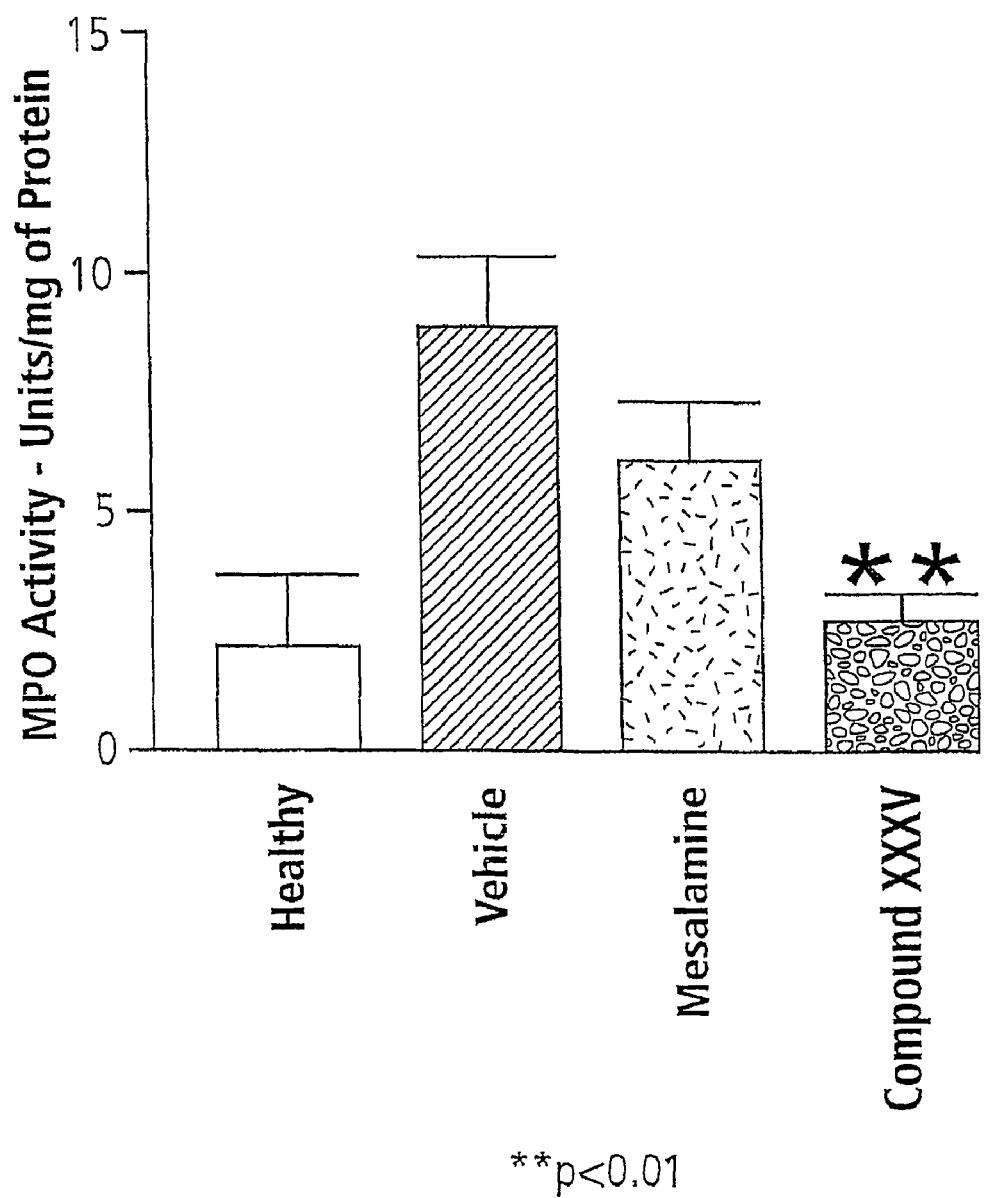
FIG. 7 shows the myeloperoxidase (MPO) activity in mice having TNBS-induced colitis after treatment with 50 mg/kg mesalamine and equimolar dose of Compound XXXV of the present invention.
Figure 8:
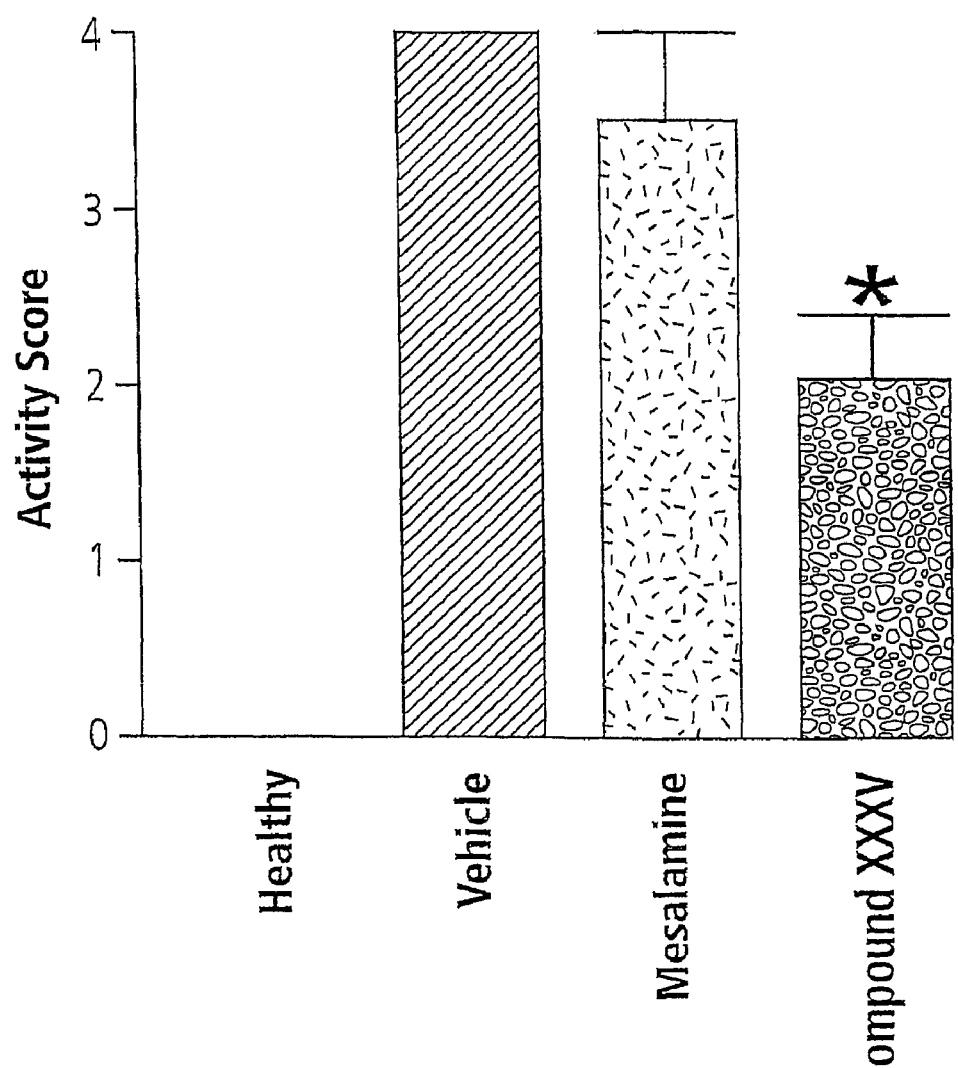
FIG. 8 shows the Disease Activity Score of mice having TNBS-induced colitis after treatment with vehicle (1% CMC), 50 mg/kg mesalamine and equimolar dose of Compound XXXV of the present invention.
Figure 9:
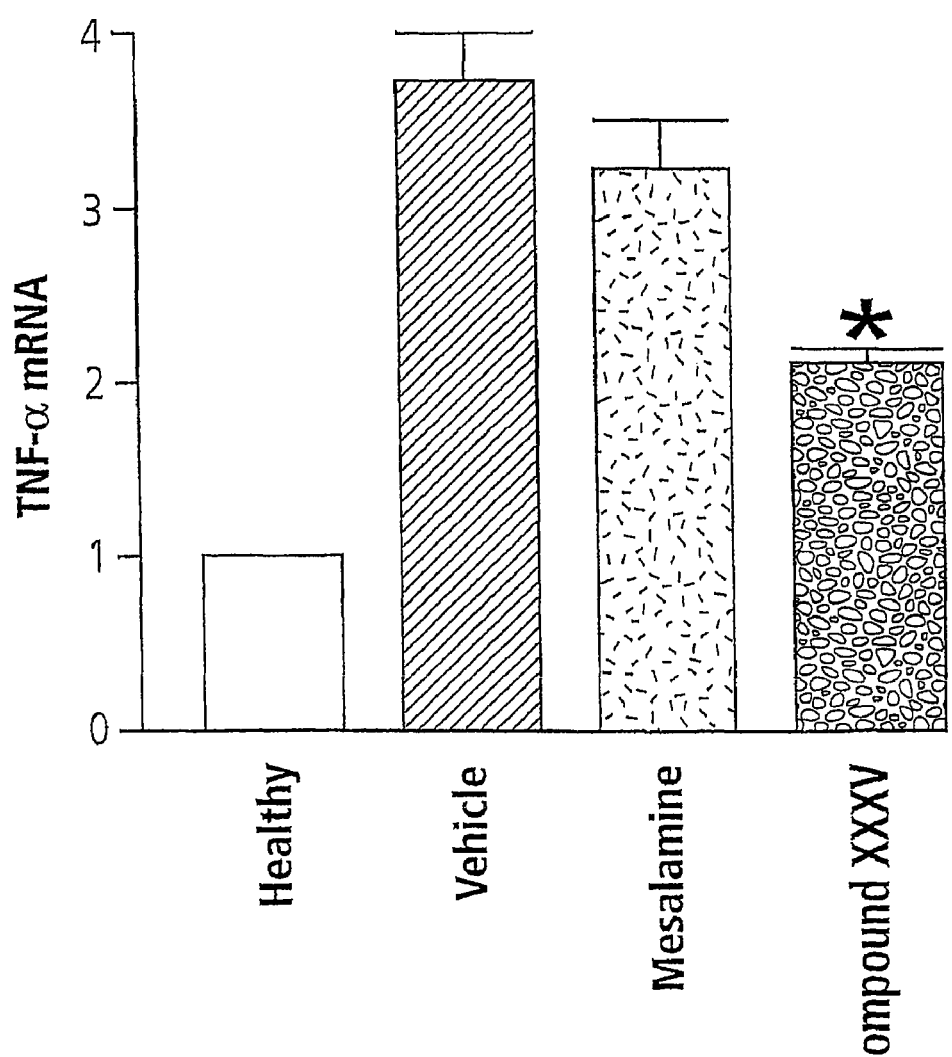
FIG. 9 shows colonic tumour necrosis factor (TNF-α) mRNA expression in mice with TNBS-induced colitis after treatment with vehicle (1% CMC), 50 mg/kg mesalamine and equimolar dose of Compound XXXV of the present invention.
Figure 10:
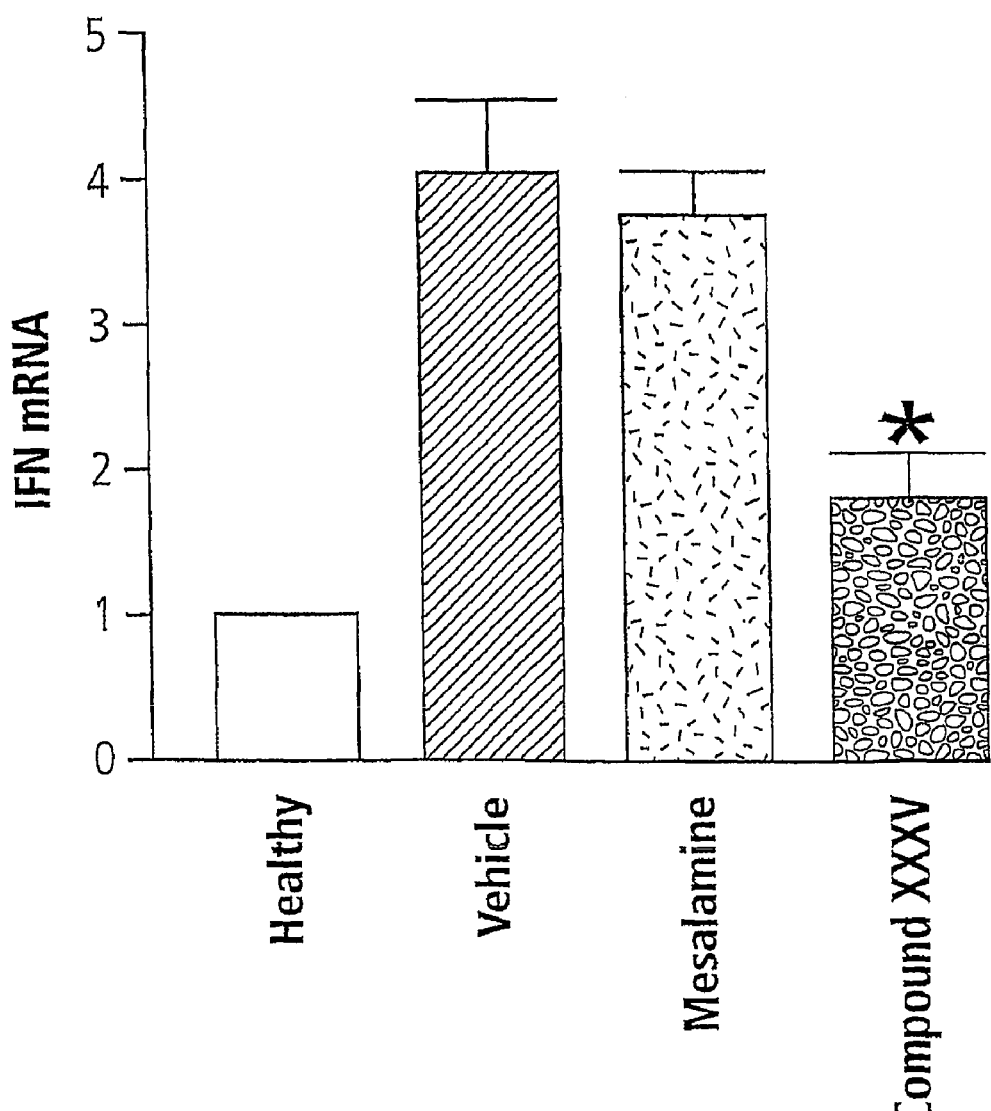
FIG. 10 shows interferon gamma (IFN-γ) mRNA expression in mice with TNBS-induced colitis after treatment with vehicle (1% CMC), 50 mg/kg mesalamine and equimolar dose of Compound XXXV of the present invention.
Figure 11:
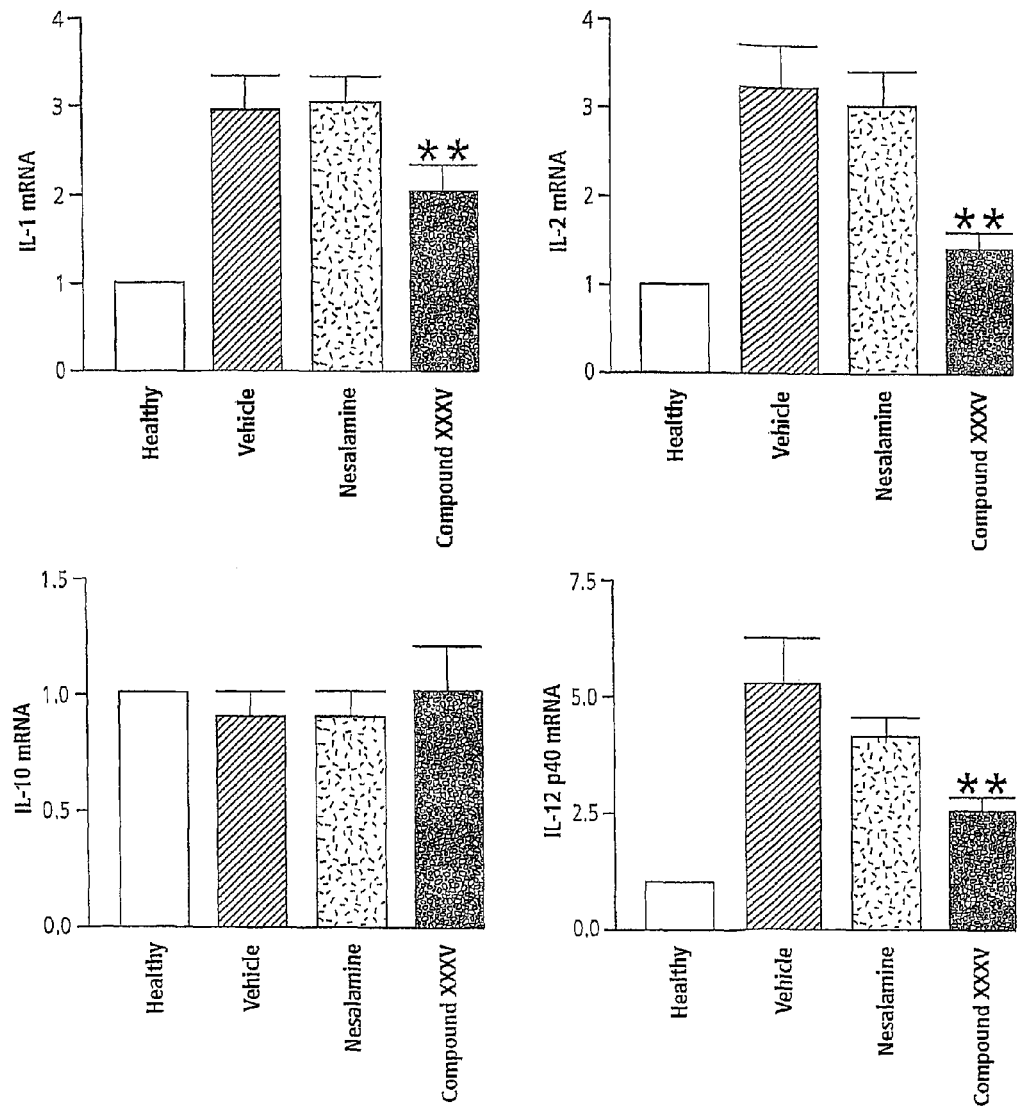
FIG. 11 shows various interleukin (IL) mRNA expression, namely, IL-1, -2, 10 and -12 mRNA, in mice with TNBS-induced colitis after treatment with vehicle (1% CMC), 50 mg/kg mesalamine and equimolar dose of Compound XXXV of the present invention.
Figure 12:
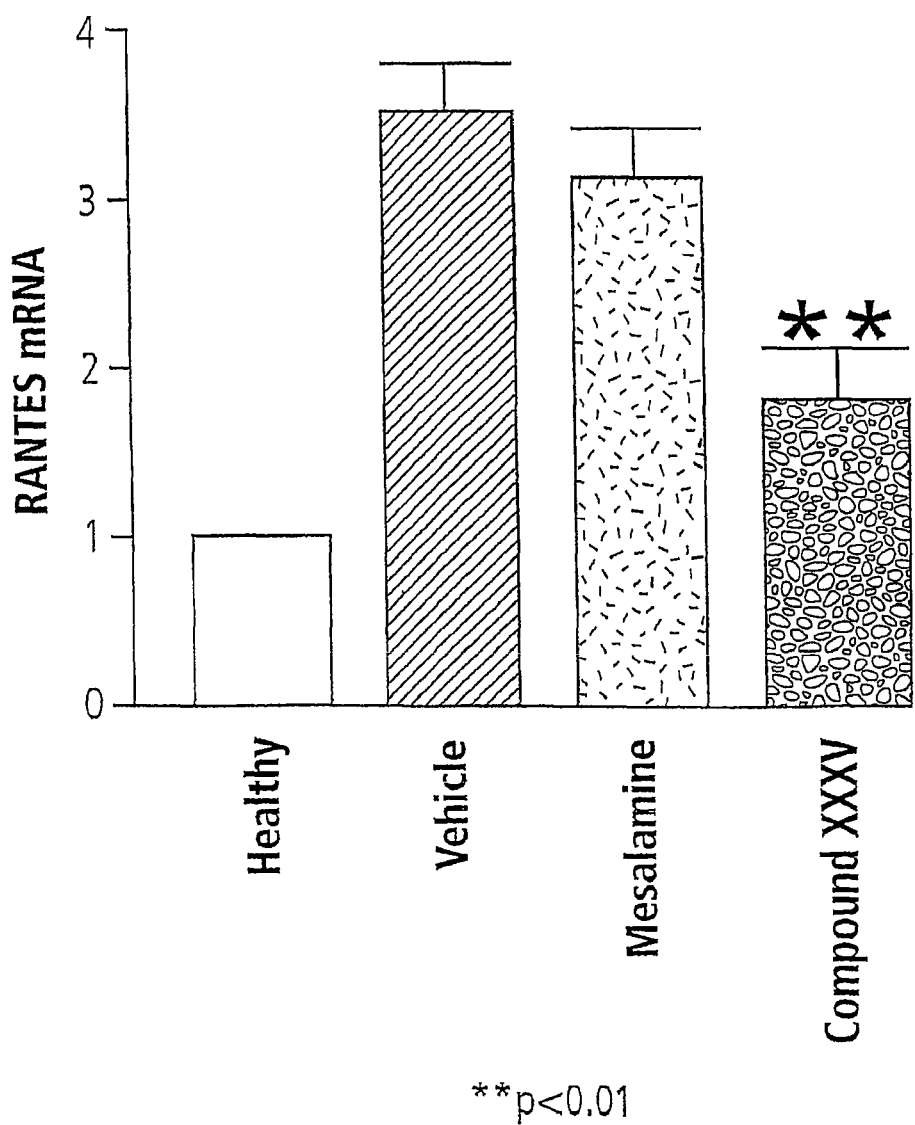
FIG. 12 shows colonic levels of RANTES mRNA in mice with TNBS-induced colitis after treatment with vehicle (1% CMC), 50 mg/kg mesalamine and equimolar dose of Compound XXXV of the present invention.

FIGS. 6 and 7 show the Disease Activity Index and MPO, respectively, using the same experimental animal model of colitis as described above, in which Compound XXVII (100 mg/kg) was compared to equimolar doses of its two constituents, mesalamine (50 mg/kg) and 4-hydroxythiobenzamide (4-HTB) (50 mg/kg), mesalamine alone (50 mg/kg) and 4-HTB alone (50 mg/kg). *p<0.05 versus the vehicle-treated group. Each group consisted of at least 5 rats.

Figure 5:
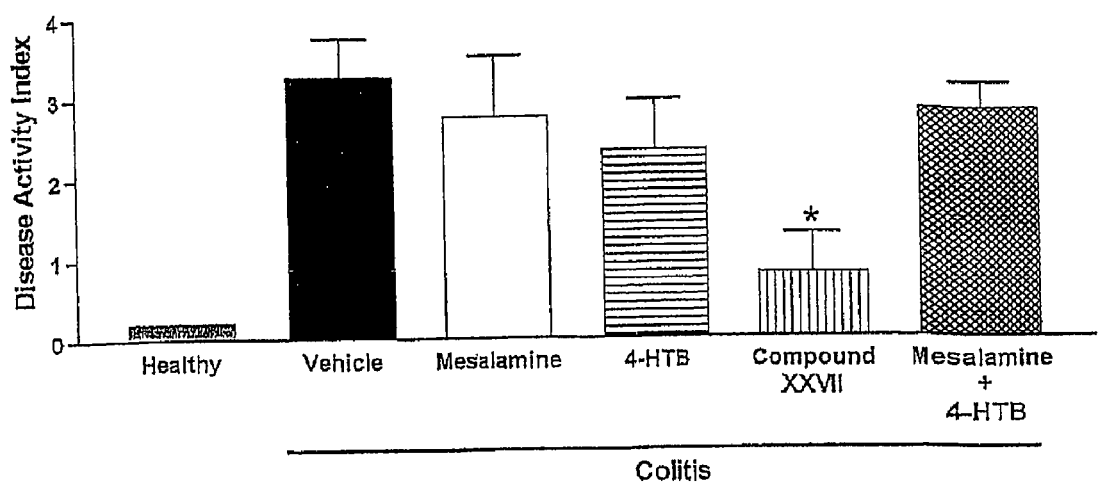
FIG. 5 shows the Disease Activity Score of mice having TNBS-induced colitis after treatment with Compound XXVII, mesalamine alone, 4-hydroxythiobenzamide (4-HTB) alone and a mixture of mesalamine and 4-HTB.

FIG. 5 shows that Compound XXVII is almost three times as effective as either mesalamine alone, 4-HTB alone or a mixture of mesalamine and 4-HTB in reducing disease symptoms. Further, FIG. 6 shows that Compound XXVII significantly reduced inflammation as indicated by the reduction in granulocyte infiltration (reduced MPO activity).

EXAMPLE 22

Effects of Mesalamine and Compound XXXV in TNBS-Induced Colitis in Mice

The same model was used as described above. In this example, the effects of mesalamine (50 mg/kg) were compared to those of equimolar doses of Compound XXXV. In addition to measuring the severity of colitis by measuring disease activity score and MPO activity, tissues were processed for measurement of a number of genes for inflammatory cytokines and other mediators.

In particular, mRNA expression in mice of tumour necrosis factor-alpha (TNF-α), interferon gamma (IFN-γ), colonic interleukin (IL)-1, IL-2, IL-10, IL-12 p40, RANTES, cyclooxygenase (COX)-1, COX-2, constitutive endothelial nitric oxide synthase (eNOS), and inducible NOS (iNOS) was measured as described in Wallace et al. (1999) *Gastroenterology* 117: 557-566, incorporated herein by reference.

Briefly, reverse transcription-polymerase chain reaction (RT-PCR) was used to detect and quantify mRNA of the particular cytokine/chemokine/enzyme. Glyceraldehyde-3-phosphate dehydrogenase (GAPDH) was used as the "housekeeping gene" for mRNA expression (i.e., as an internal control). For each sample, the ratio of the amplification of the target gene to the amplification of GAPDH (expression of each is measured by performing densitometry on gels) was obtained. Comparisons were then made between the relative amplification (expression) of the target gene in tissues for the treatment groups in comparison to the expression in tissues from healthy controls. Thus, the data shown in FIGS. 7-14 represent the relative expression of the target gene (normalized to GAPDH expression) as a ratio to the expression in healthy controls.

With reference to FIGS. 7-14, it is noteworthy that Compound XXXV was superior to mesalamine in every endpoint. It is particularly interesting that Compound XXXV suppressed expression of mRNA for several pro-inflammatory cytokines and chemokines that have been implicated in the pathogenesis of inflammatory bowel disease. However, Compound XXXV did not suppress expression of IL-10 mRNA, which is an anti-inflammatory cytokine.

In addition, Compound XXXV suppressed both COX-1 and COX-2 mRNA. COX-1 and COX-2 are involved in the synthesis of prostaglandins, which are important in inflammation. Further, Compound XXXV also suppressed eNOS and iNOS mRNA. Both eNOS and iNOS have been implicated in diseases of the GI tract

EXAMPLE 23

Comparison of the Effects of Compound XXXV Versus Mesalamine in Inhibiting Viability of HT-29 Human Colon Cancer Cells In Vitro HT-29 cells were grown in culture using standard methods. The cells were exposed to vehicle (DMSO), mesalamine or Compound XXXV. Concentrations ranging from 0.1 to 10 μM were tested, with each concentration tested in 6 wells. At the end of 72 h of exposure to the test drugs, cell viability was measured using the MTT [3-(4,5-dimethylthiaxol-2-yl)-2,5-diphenyltetrazolium bromide] assay (Carmichael et al. (1978) *Cancer Res.* 47, 936-942), incorporated herein by reference. Cell viability rates were calculated as a percent of the vehicle (DMSO)-treated cells and results are given in Table 1.

TABLE 1

| Drug | Concentrations (μM) | | |
| --- | --- | --- | --- |
| | 0.1 | 1 | 10 |
| Mesalamine | 103.8 ± 2.5 | 101.2 ± 3.5 | 91.1 ± 3.2 |
| XXXV | 88.4 ± 2.9** | 87.3 ± 2.3** | 79.6 ± 1.9** |

**p < 0.01 versus the mesalamine-treated group (same concentration)

EXAMPLE 24

Comparison of the Effects of Compound XXXV versus Mesalamine in a Rat Model of Visceral Pain Perception A rat model of visceral pain perception, a pre-clinical model of irritable bowel syndrome, was used in the following example. Rats (male, Wistar, 200-250 g, obtained from Charles River, Monza, Italy), were housed in plastic cages and maintained under controlled conditions with 12-hours light/dark cycle with lights on at 7.00 AM. Tap water and standard laboratory chow were freely available. Before experiments, rats were individually trained by spending 2-3 hours per day in a plexiglass cage for 2-3 days. It allowed them to adjust to a movement-restriction environment. Food was withheld for 12 hours before colorectal distension (CRD) recording were performed. Experiments were performed in awake rats and were conducted in a blind manner in that the observer was not aware of the identity of drug administered to each animal.

In the testing day, rats were sedated with ether inhalation and a 2 cm long latex balloon was inserted intrarectally 2 cm from the anal verge and fixed at the base of the tail. The balloon was connected via a double-barreled cannula to a pressure transducer to continuously monitoring the rectal pressure by a computer (PowerLab PC, A.D. Instruments, Milford, Mass., USA) and to a syringe for inflation/deflation of the balloon. The rats were then housed in a small cage (20×8×8 cm) on an elevated Plexiglas™ platform and allowed to wake up and adapt for 1 hour. After recovery from sedation, animals underwent the CRD procedure and behavioral responses were tested. The night before the experiments, the balloons were inflated and left overnight so the latex stretched and the balloons became compliant.

CRD of 20 seconds, performed every 5 minutes, was applied in increment of 0.4 ml starting from 0.4 ml up to 1.6 ml water. To achieve an accurate measurement of the colonic parameters and perception, the distensions were repeated twice for each intensity and data for each animal were averaged for analysis. Each animal underwent a double set of CRD. Twenty minutes after the first sequence of CRD (0.4 mL-1.6 ml water), drugs were administered intraperitoneally (i.p.) and a second set of CRD was performed. Behavioral responses during the first and the second set of CRD were assessed and compared.

Behavioral response to CRD was assessed by measuring the abdominal withdrawal reflex (AWR) using a semiquantitative score (1). The AWR is an involuntary motor reflex similar to the visceromotor reflex, but it has the great advantage that, in contrast to the latter, it does not require abdominal surgery to implant recording electrodes and wires in the abdominal muscle wall which may cause additional sensitization (see Ness, T. J. and Gebhart, G. F. (1990) *Pain* 41:167-234, incorporated herein by reference).

Measurement of the AWR consisted of visual observation of the animal response to graded CRD by blinded observer and assignment of an AWR score according with the behavioral scale as previously described in Al-Chaer, E. D. et al. (2000) *Gastroenterology* 19: 1276-85, incorporated herein by reference, in which grade 0 corresponds to no behavioral response to CRD, grade 1 corresponds to brief head movement at the onset of the stimulus followed by immobility, grade 2 corresponds to a mild contraction of abdominal muscles although the rats does not lift the abdomen off the platform, grade 3 corresponds to a strong contraction of the abdominal muscles with the lifting of the abdomen off the platform, and grade 4 corresponds to a severe contraction of the abdominal muscle manifested by body arching and the lifting of the abdomen and of the pelvic structures and scrotum.

The effects of mesalamine and Compound XXXV on colonic compliance and sensitivity were determined using a total of 8 fasting rats. To investigate whether the administration of mesalamine and Compound XXXV could revert pain induced by CRD, after the first sequence of CRD, 4 rats were treated with mesalamine at the dose of 100 mg/kg i.p. or Compound XXXV at the dose of 100 mg/kg i.p., after which a second set of CRD was repeated. Results from these experiments are shown in FIGS. 15(a) and (b).

Figure 16:
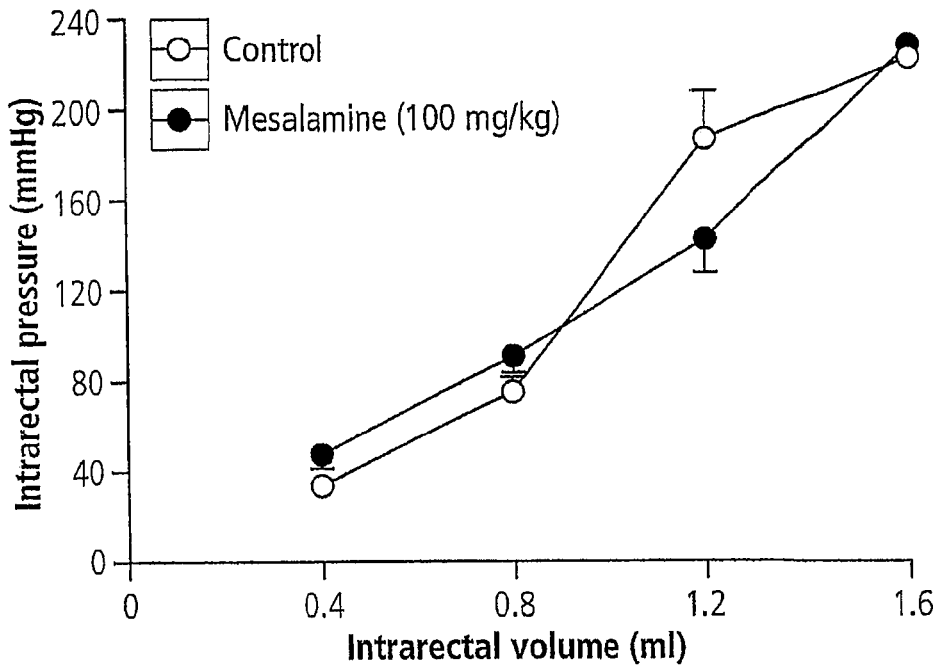
FIGS. 16(*a*) and (*b*) show the intrarectal pressure in a rat model of visceral pain perception using mesalamine and Compound XXXV, respectively, of the present invention.
Figure 16:
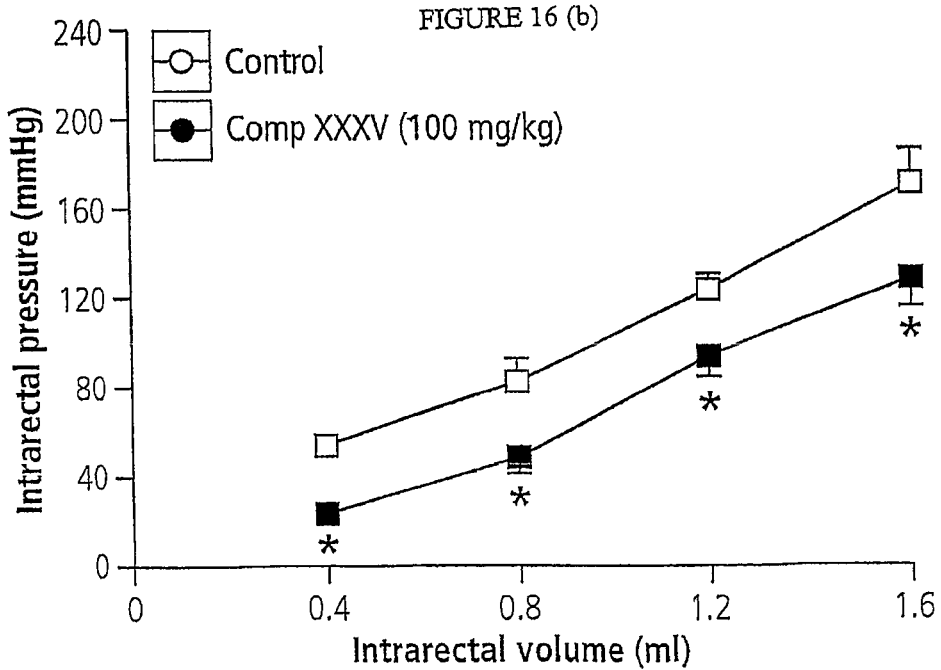

To determine the effect of mesalamine or Compound XXXV on colonic smooth muscle, the compliance of the colo-rectum during CRD was obtained from intracolo-rectal volume and pressure and expressed as mL/mmHg. These results are shown in FIGS. 16(a) and (b).

All data are presented as the mean±SEM, with sample sizes of 4 rats/group; statistical comparison of paired data was performed by the Wilcoxon signed rank test. An associated probability (p value) of less that 5% was considered significant.

Figure 15:
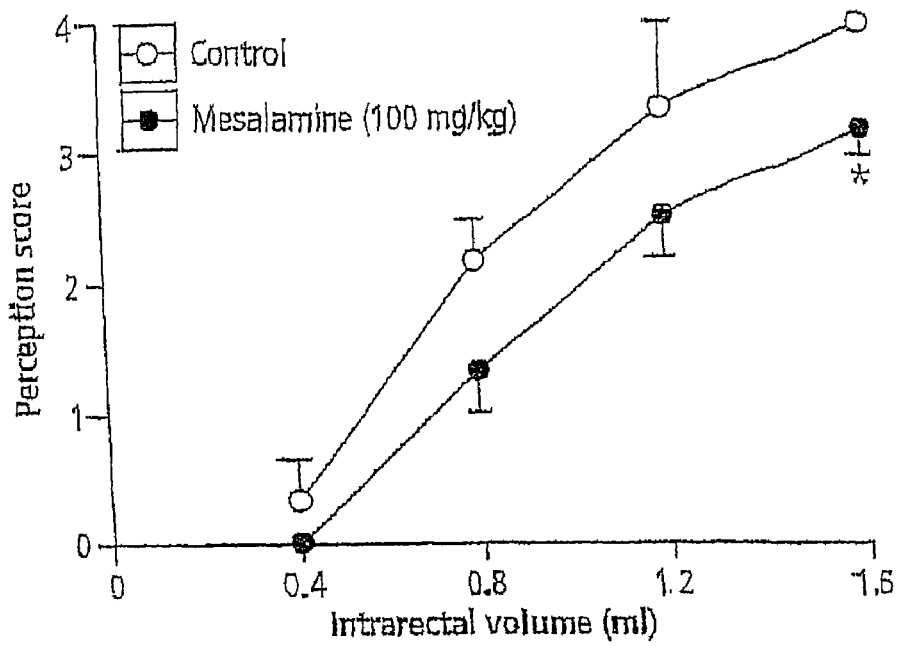
FIGS. 15(*a*) and (*b*) show the perception score in a rat model of visceral pain perception using mesalamine and Compound XXXV, respectively, of the present invention.
Figure 15:
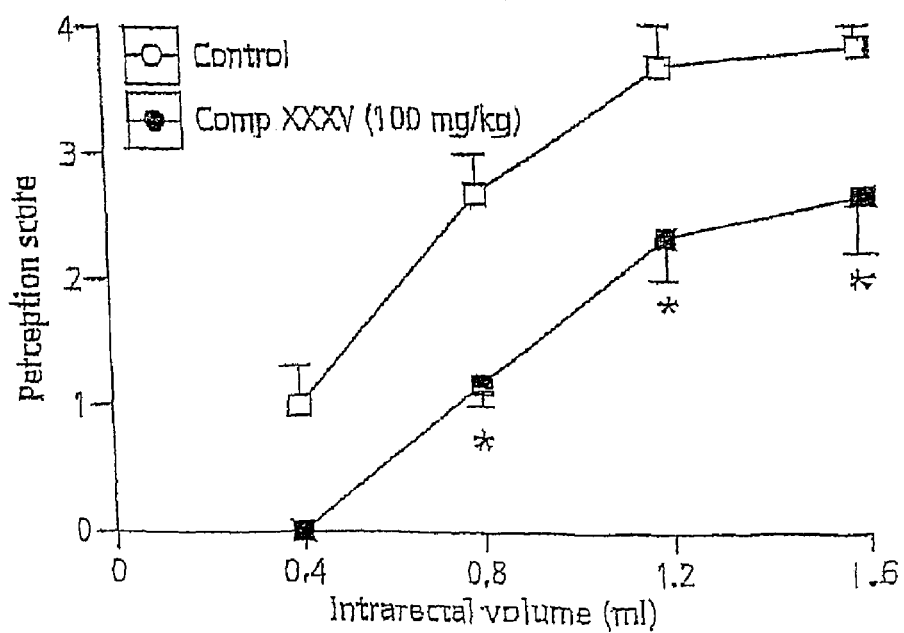

FIGS. 15(a) and (b) show that Compound XXXV is more effective than mesalamine (and vehicle) in reducing visceral pain in response to colorectal distension. Further, Compound XXXV successfully reduced intrarectal pressure, as shown in FIG. 16(b).

Thus, Compound XXXV, which has also been shown to have effective anti-inflammatory activity, is useful in treating various inflammatory conditions of the alimentary tract, as well as functional gastrointestinal disorders such as irritable bowel syndrome, dyspepsia, etc., that are characterized by increased visceral nociception (with or without accompanying inflammation).

EXAMPLE 25

Compound XXXV and Compound XXVII Pain Perception Scores with or without Glibenclamide A rat model of visceral pain perception as described above was used to compare pain perception scores for both Compound XXXV and Compound XXVII with or without glibenclamide, an inhibitor of ATP-sensitive $K^+$ ($K_{ATP}$) channels.

Figure 17:
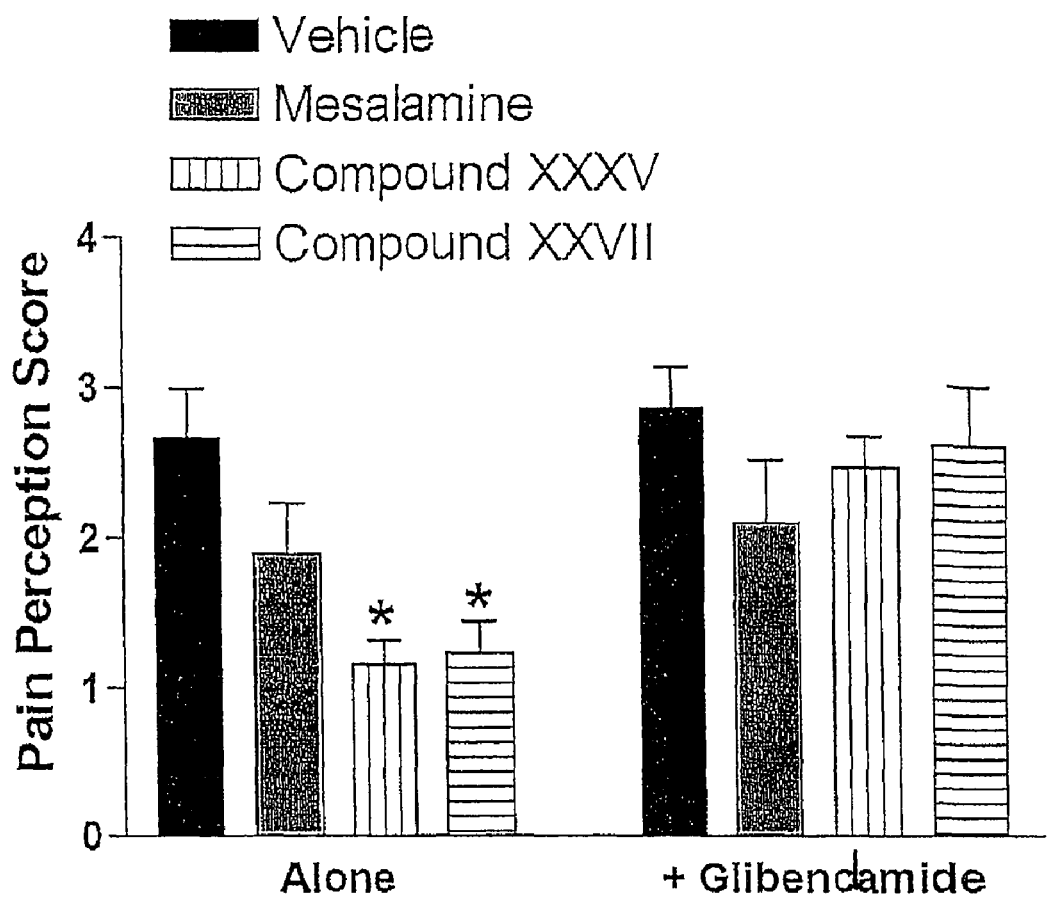
FIG. 17 shows the pain perception scores of mesalamine, Compound XXXV and Compound XXVII with or without glibenclamide.
Figure 18:
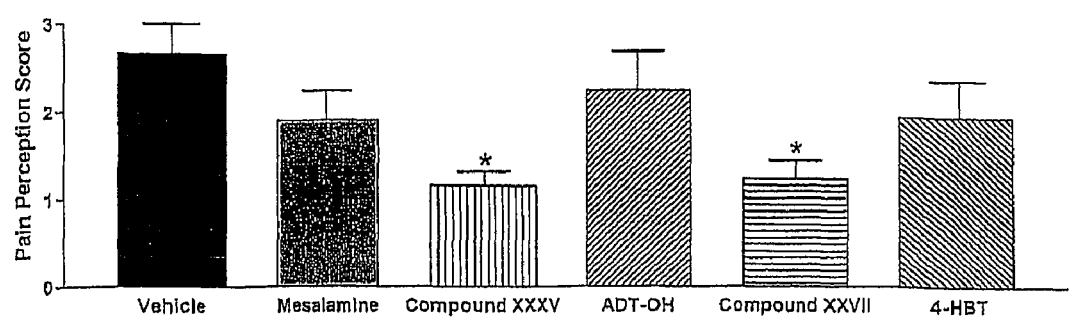
FIG. 18 shows the pain perception scores of Compound XXXV, Compound XXVII, mesalamine, ADT-OH and 4-HBT.

FIG. 17 shows the pain perception score in response to 0.8 mL of colorectal distention in groups of rats (at least 5 per group) treated with vehicle, mesalamine (100 mg/kg), Compound XXXV (100 mg/kg) or Compound XXVII (100 mg/kg). Both Compound XXXV and XXVII significantly reduced the pain perception (*$p<0.05$ versus the vehicle-treated group), while mesalamine had no significant effect. The reduction of pain perception by Compound XXXV and Compound XXVII was reversed by pretreatment with glibenclamide (10 mg/kg i.p. 30 min before), while glibenclamide pretreatment did not affect the pain perception in the groups treated with vehicle or mesalamine, suggesting that the anti-nociceptive activity of Compounds XXXV and XXVII may be mediated by ATP-sensitive $K^+$ ($K_{ATP}$) channels.

EXAMPLE 26

Figure 19:
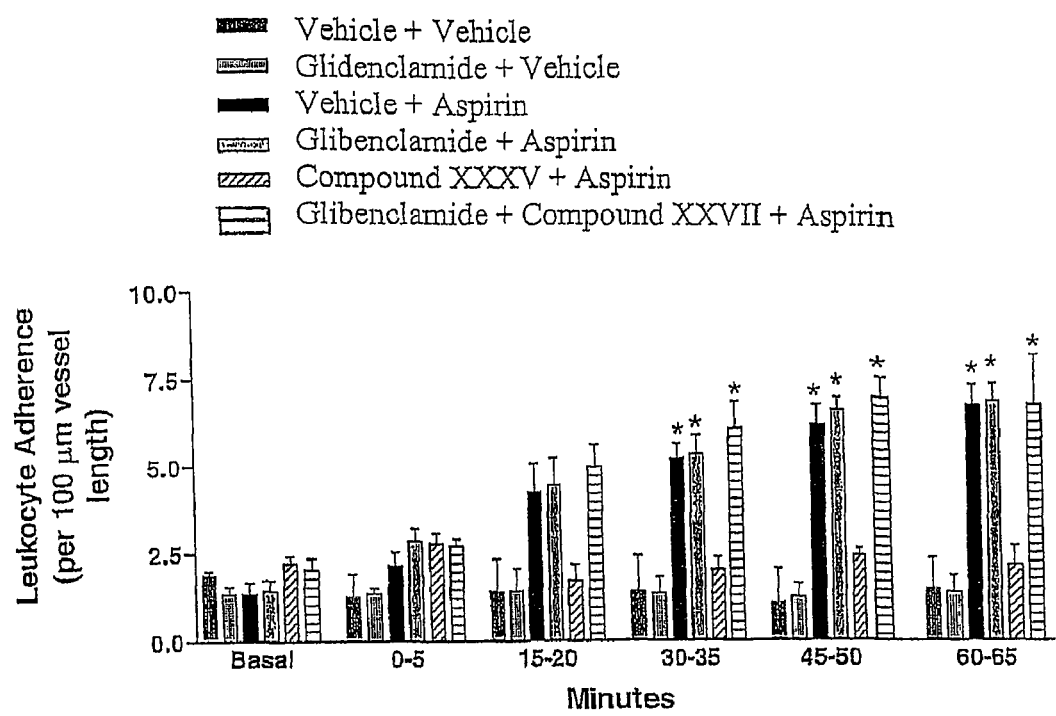
FIG. 19 shows leukocyte adherence in response to intragastric administration of aspirin.

Comparison of Compound XXXV and Compound XXVII Pain Perception Scores with Mesalamine FIG. 19 shows results from an experiment using the same pain model as described above. The effects of treatment with mesalamine (50 mg/kg) were compared to the effects of equimolar doses Compound XXXV (130 mg/kg), ADT-OH (80 mg/kg), Compound XXVII (100 mg/kg) and 4-HTB (50 mg/kg). Only Compound XXXV and Compound XXVII significantly reduced pain perception (*$p<0.05$) when compared to the vehicle-treated group.

EXAMPLE 27

Effects of Compounds XXXV and XXVII on Leukocyte Adherence to the Vascular Endothelium In Vivo Leukocyte adherence was studied using intravital microscopy, as described in detail previously (Wallace et al., (1993) *Am. J. Physiol.* 265: 993-998, incorporated hereto by reference). Rats were anesthetized with pentobarbital sodium (60 mg/kg i.p.) and cautery incisions were made along the abdominal region. A tracheotomy was performed to facilitate breathing. The rats were placed in a supine position, and a segment of the mesentery was exteriorized through the abdominal incision. The mesentery was carefully placed over an optically clear viewing pedestal that allowed for trans-illumination of a 2-cm² segment of tissue. All exposed tissue was covered with saline-soaked gauze to minimize dehydration. The temperature of the pedestal was kept at 37° C. and the mesentery was superfused with warmed bicarbonate-buffered saline (pH 7.4). An intravital microscope (Nikon L25/0.35) and a ×10 eyepiece were used to observe the mesenteric microcirculation. Post-capillary venules with diameters ranging from 20 to 40 µm were selected for the study. A video camera mounted on the microscope (Panasonic™ digital 5000) projected the image onto a monitor, and the images were recorded for playback analysis using a videocassette recorder. Images of the mesenteric microcirculation were recorded 5 minutes prior to aspirin administration (baseline), at the time of aspirin administration (time 0-5) and every 15 minutes for 60 minutes. Leukocyte adherence was blindly quantified from videotaped images of the vessels made over 5-min periods as the number of leukocytes that remained stationary along the vessel wall for 30 s or more (expressed per 100 μm venule length). Groups of rats (at least 5 in each) were pretreated with Compound XXXV (130 mg/kg), Compound XXVII (100 mg/kg), mesalamine (50 mg/kg), or vehicle 60 min prior to aspirin (or vehicle) administration. These drugs were given intragastrically. In some experiments, rats were treated with glibenclamide (10 mg/kg i.p.) or vehicle 30 min prior to administration of these compounds.

FIG. 19 shows leukocyte adherence in response to intragastric administration of aspirin, and the effects of the compounds. Aspirin markedly increased leukocyte adherence over that observed in the baseline period (*p<0.05 versus the vehicle+vehicle group. Pretreatment with compound XXXV, but not with mesalamine, prevented the aspirin-induced increase in leukocyte adherence. Glibenclamide alone did not affect leukocyte adherence, and did not affect the magnitude of aspirin-induced leukocyte adherence. Glibenclamide also had no effect in the group treated with mesalamine plus aspirin. However, glibenclamide reversed the inhibitory effect of Compound XXXV on aspirin-induced leukocyte adherence.

Figure 20:
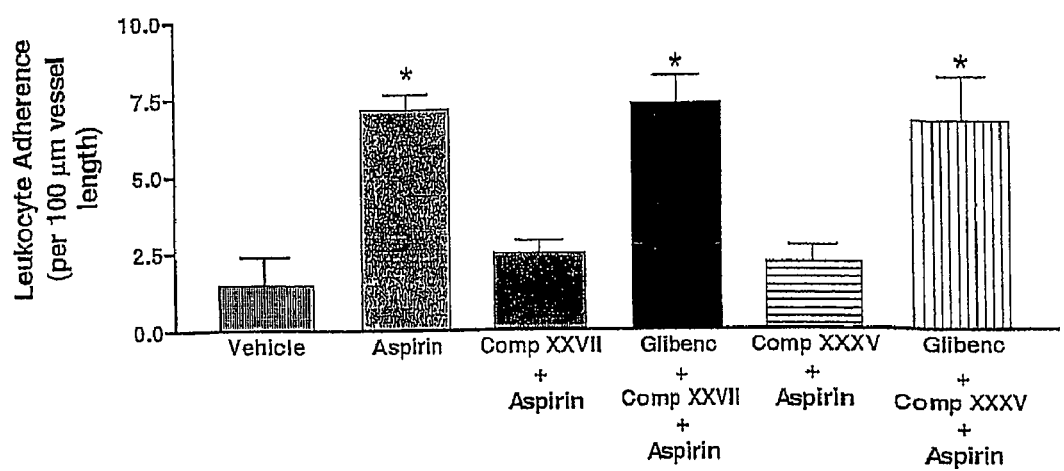
FIG. 20 is a bar graph of the leukocyte adherence for the final time period of the experiment (minutes 60-65).

FIG. 20 shows the leukocyte adherence for the final time period of the experiment (minutes 60-65). This graph illustrates the ability of Compound XXXV and Compound XXVII to suppress aspirin-induced leukocyte adherence, and the ability of glibenclamide pretreatment to reverse this inhibitor effect on leukocyte adherence.

EXAMPLE 28

Generation of $H_2S$ by 5-Amino-2-hydroxy-benzoic acid 4-(5-thioxo-5H-[1,2]dithiol-3-yl)-phenyl ester (Compound XXXV) and 4- or 5-Amino-2-(4-thiocarbamoyl-phenoxycarbonyloxy)-benzoic acid (referred to as Compound XXVII)

Figure 13:
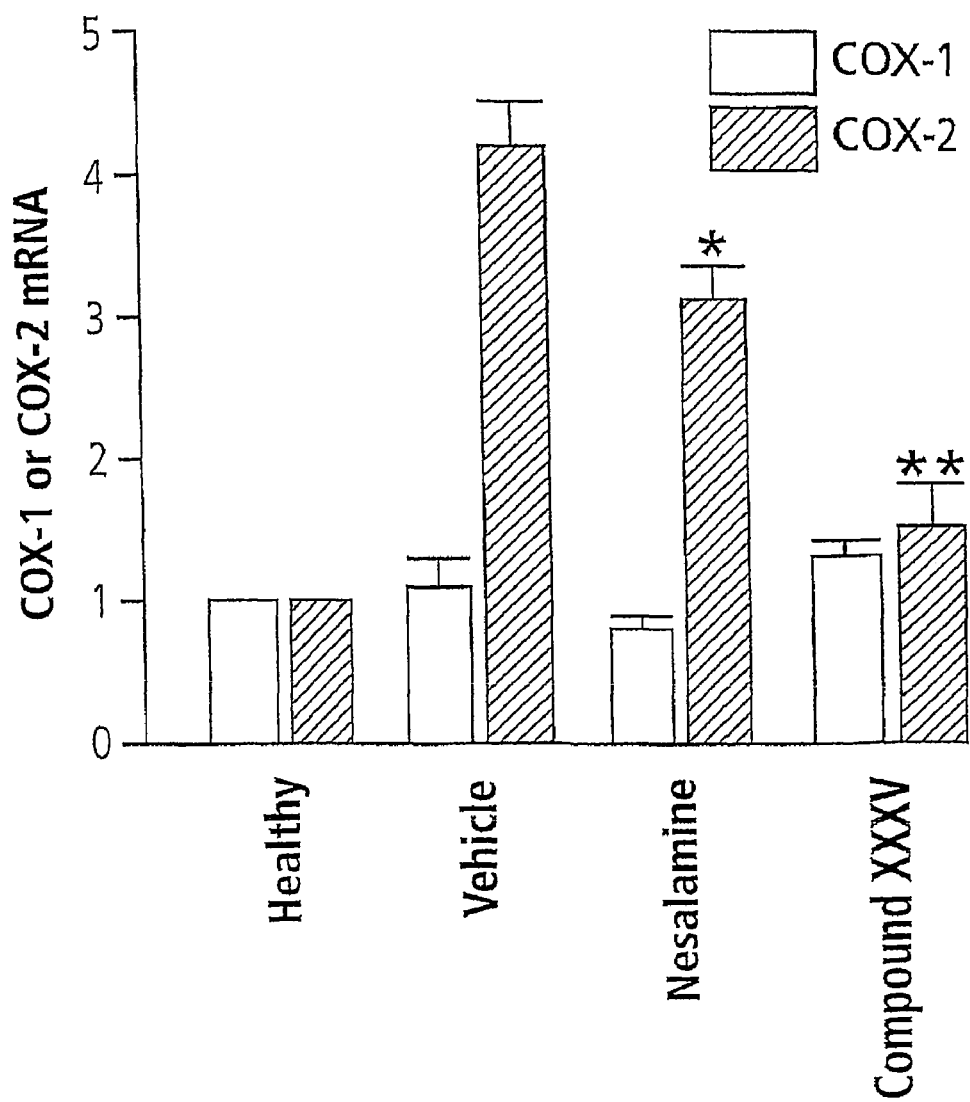
FIG. 13 shows colonic COX-1 and COX-2 mRNA expression in mice with TNBS-induced colitis after treatment with vehicle (1% CMC), 50 mg/kg mesalamine and equimolar dose of Compound XXXV of the present invention.
Figure 14:
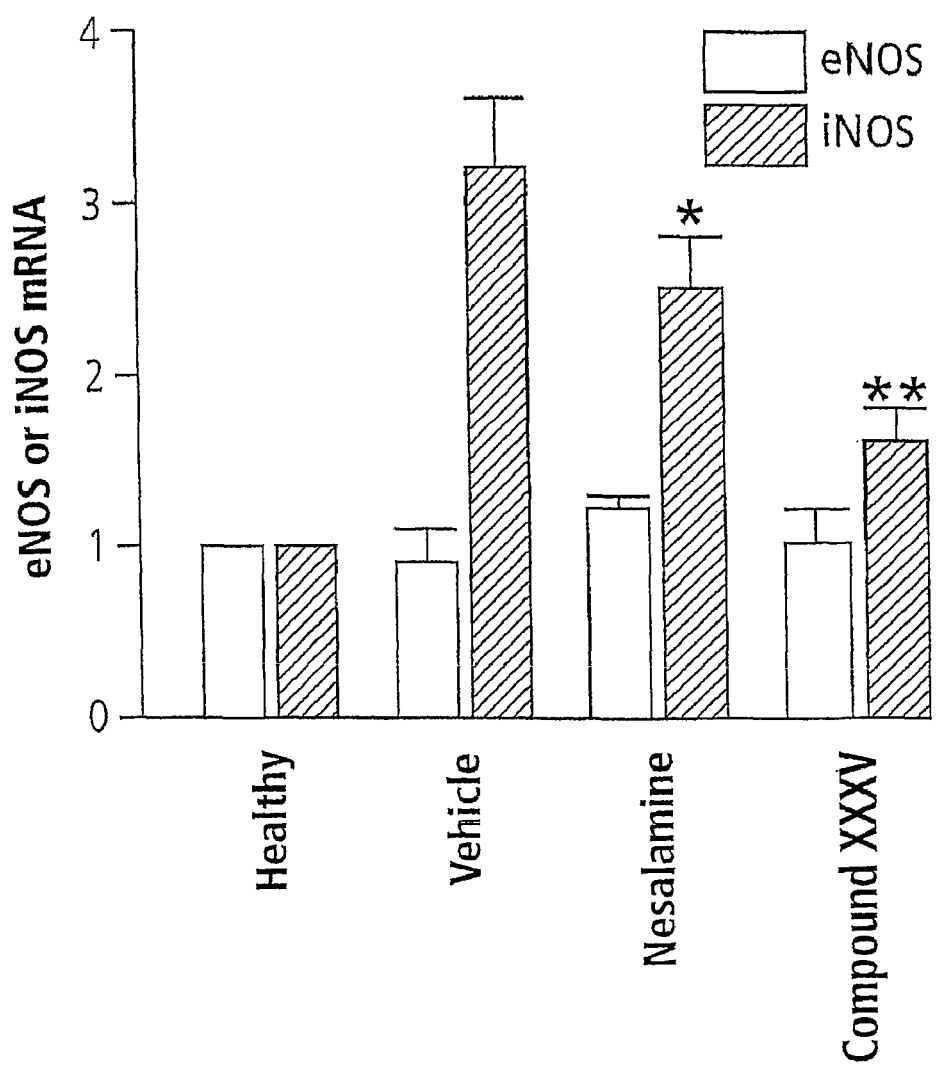
FIG. 14 shows colonic eNOS and iNOS mRNA expression in mice with TNBS-induced colitis after treatment with vehicle (1% CMC), 50 mg/kg mesalamine and equimolar dose of Compound XXXV of the present invention.

Two compounds were tested, Compound XXXV and Compound XXVII, for $H_2S$ generation under three different conditions. Concentrations of $H_2S$ that were generated within 1 hour from 1 mM concentrations of L-cysteine, the $H_2S$-releasing moiety of Compound XXXV, ADT-OH (5-(4-Aminophenyl)-[1,2]dithiole-3-thione, the $H_2S$ releasing moiety of Compound XXVII, 4-HBT (4-hydroxythiobenzamide) were also measured. $H_2S$ release was tested under three conditions: (i) when the compound was in buffer, (ii) when the compound was in a liver homogenate, and (iii) when the compound was in the liver homogenate together with an inhibitor of cystathionine γ-lyase (PAG=DL-propargylglycine; 2 mM). Results are shown in FIG. 13. *p<0.05 compared to the release from the vehicle group. ᵛp>0.05 versus the corresponding 'homogenate' group. The enzymatic capacity for $H_2S$ production was determined using the same reactor as described previously (Khan et al. (1980) *Microchem J.* 25: 388-395, incorporated herein by reference). Two ml of an assay reaction mixture was introduced in the reactor. The mixture contained 1 mM L-cysteine (or compound), 2 mM pyridoxal 5'-phosphate, 100 mM potassium phosphate buffer (pH=7.4). A constant stream of nitrogen was passed through the mixture via gas-inlet capillary. Reactions were initiated by transferring the tubes from ice bath to a 37° C. water bath. The stream of nitrogen carried the sulfide acid in the second reactor containing 4 ml of sulfide anti-oxidant buffer (SAOB) solution, consisting of 2M KOH, 1M salicylic acid and 0.22M ascorbic acid at pH 12.8[5]. After incubating at 37° C. for 90 minutes, 1 ml of 10% trichloroacetic acid solution was added to mixture to stop the reaction. The remainder $H_2S$ in the mixture was carried out via nitrogen stream by other 60 minutes of incubation at 37° C. The concentration of sulfide in SAOB solution was measured with a sulfide sensitive electrode (Model 9616 $S^{2-}/Ag^+$ electrode, Orion Research, Beverly, Mass., USA. For studies in which the test compounds were incubated in liver homogenate, 100-150 mg of isolated rat livers were homogenized in 1 ml of ice-cold T-PER protein extractor. The homogenates were added to the reaction mixture at a concentration of 10% (wt/vol). DL-propargylglycine 2 mM was incubated with liver homogenates for 5 min at 37° C. prior the enzyme reaction. Khan, S. U. Morris, G. F. and Hidiroglou, M. (1980) Rapid estimation of sulfide in rumen and blood with a sulfide-specific ion electrode. *Microchem J.* 25:388-395, incorporated herein by reference.

Figure 21:
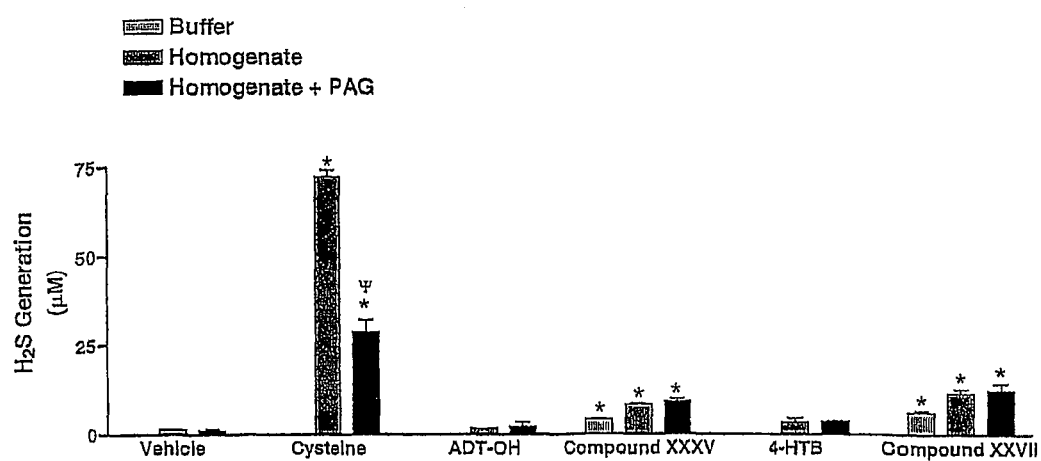
FIG. 21 is a bar graph showing H2S generation of cysteine, ADT-OH, Compound XXXV, 4-HTB and Compound XXVII.

The results shown in FIG. 21 suggest that 4- or 5-ASA derivatives of the present invention and, in particular, Compound XXXV and XXVII, have the following distinct features:

1. The derivatives release $H_2S$ spontaneously (in buffer), which is desirable for a topical effect in the gut. The $H_2S$-releasing moieties alone, ADT-OH and 4-HTB, and L-cysteine did not release significant $H_2S$ when incubated only in buffer;
2. The release of $H_2S$ is greater when in the presence of tissue;
3. The release of $H_2S$ from 4- or 5-ASA derivatives (other than 4- or 5-amino-2-hydroxy-benzoic acid anhydride with N-acetyl cysteine (Formula X), occurs independent of the activity of the two main enzymes for endogenous synthesis of $H_2S$ (cystathionine β-synthase and cystathionine-γ-lyase). This is demonstrated by lack of effect of an inhibitor of those enzymes (PAG; DL-propargylglycine), on $H_2S$ generation from Compound XXXV and Compound XXVII. In contrast, the release of $H_2S$ from L-cysteine is markedly inhibited by PAG;
4. The concentrations of $H_2S$ produced from Compound XXXV and Compound XXVII are in the 10-20 uM range when 1 mM of the compound was used. Concentrations of up to 5 mM mesalamine can be measured in the colonic lumen after patients have taken the usual doses of this drug (*Dig. Dis. Sci.* 1989; 34: 573-578). Endogenous concentrations of $H_2S$ can be as much as 160 μM (*Antioxid. Redox Signal.* 2003; 5, 493-501). Both Compound XXXV and XXVII release $H_2S$ at concentrations within the physiological range thereby minimizing the chances of $H_2S$-related toxicity. It is understood, however, that when n-acetylcysteine is the $H_2S$ releasing moiety (compounds of Formula X), a lower dose will be used due to the greater release of $H_2S$ from cysteine.

EXAMPLE 29

Vasorelaxant Effects of $H_2S$ Releasing Moieties

The following experiments were performed essentially using the protocol as disclosed in Bucci, M. et al. (2004) Diabetic mouse angiopathy is linked to progressive sympathetic receptor deletion coupled to an enhanced caveolin-1 expression. *Arterioscler Thromb Vasc Biol* 24: 721-726, incorporated herein by reference. CD-1 mice were sacrificed and thoracic aorta was rapidly dissected and cleaned from fat and connective tissue. Rings of 1.5-2 mm length were cut and mounted on isolated organ bath (Fort 10 World Precision Instruments, USA) filled with gassed Krebs solution (95% O2+5% CO2) at 37° C. Changes in isometric tension were recorded with PowerLab™ data acquisition system (Ugo Basile, Italy). The composition of the Krebs solution was as follows (mol/l): NaCl 0.118, KCl 0.0047, MgCl2 0.0012, KH2PO4 0.0012, CaCl2 0.0025, NaHCO3 0.025 and glucose 0.010. Rings were initially stretched until a resting tension of 1.5 g was reached and allowed to equilibrate for at least 40 minutes during which tension was adjusted, when necessary, to 1.5 g and bathing solution was periodically changed. In a preliminary study a resting tension of 1.5 g was found to develop the optimal tension to stimulation with contracting agents.

In each experiment rings were standardized using L-phenylephrine (PE) 1 μmol/l until the responses were reproducible. To evaluate the vasorelaxant effect of tested compounds, cumulative concentration-response curves were performed (10 nM-3 mM) on PE (1 μM) precontracted rings for the following compounds:

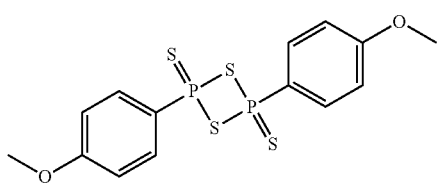

2,4-bis(4-methoxyphenyl)-1,3,2,4-dithiadiphosphetane-2,4-disulfide (Lawesson's Reagent), thioacetamide, NaHS, 4-HTB and Na$_2$S. Vehicle represents buffer but no compound. Curves to tested compounds were constructed in presence of endothelium. To assess endothelium integrity cumulative concentration-response curve to Ach (10 nM-30 μM) was performed on PE precontracted rings.

Figure 22:
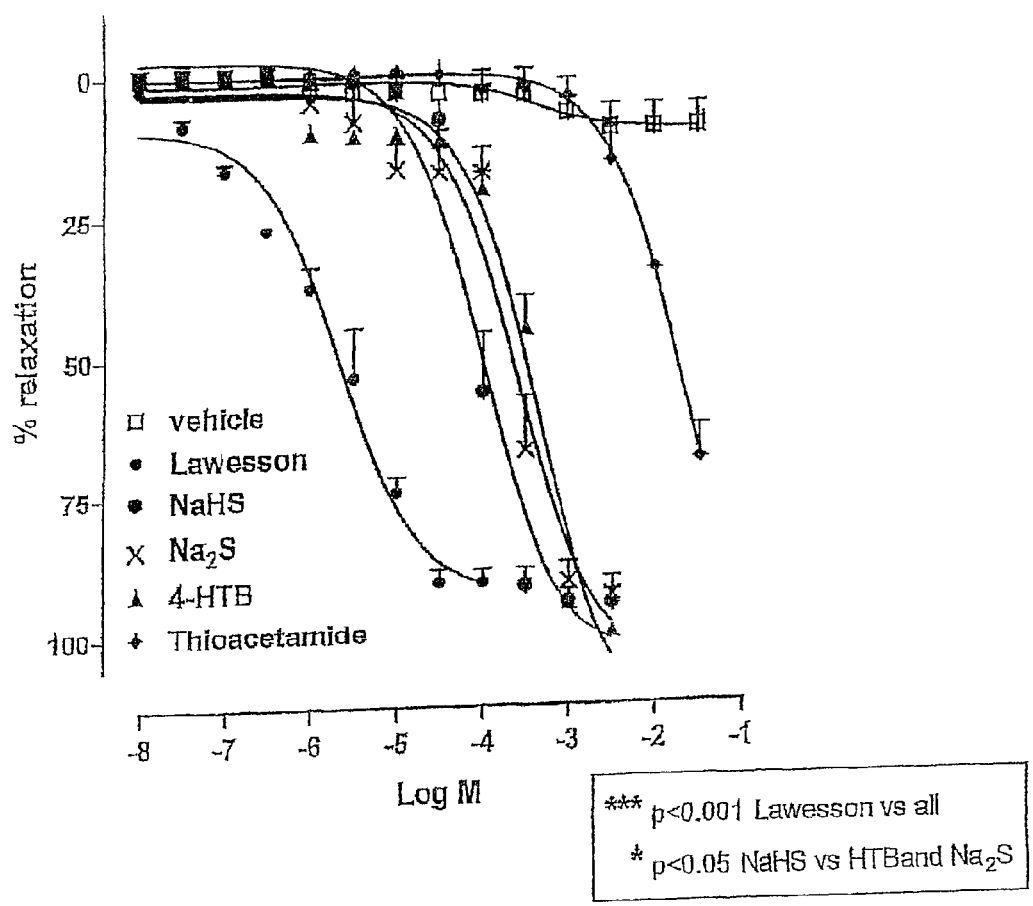
FIG. 22 is a Concentration-Response curve showing the vasorelaxant effects of $H_2S$ releasing moieties of the present invention.

Data obtained are shown in FIG. 22 and are expressed as mean±SEM. The level of statistical significance was determined by 2-way analysis of variance (ANOVA) followed by Bonferroni's test for multiple comparison, using the GraphPad™ software.

FIG. 22 shows that the H2S releasing moieties of the present invention, namely, Lawesson's Reagent, 4-HTB and thioacetamide, all showed significant vasorelaxant effects, which were concentration dependent, when compared to vehicle. Further, the % relaxation curves were all comparable to those obtained when using NaHS and Na$_2$S.

We claim:

1. A method of treating an inflammatory condition of the gastrointestinal tract selected from the group consisting of Crohn's disease, ulcerative colitis and irritable bowel syndrome in a subject in need of such treatment, said method comprising administering to the subject an amount effective to treat the inflammatory condition of the gastrointestinal tract of a compound of the general formula:

A-L-R (I)

where:
A is

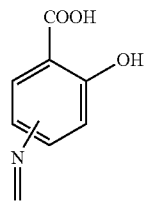

where —N= is either at position 4 or 5,

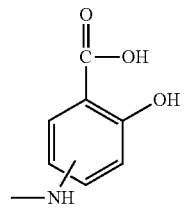

where —NH is either at position 4 or 5,

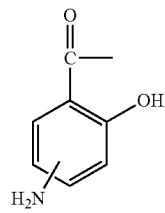

where —NH$_2$ is either at position 4 or 5, or

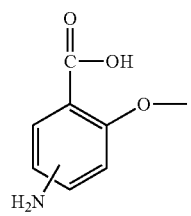

where —NH$_2$ is either at position 4 or 5;

L is either O, O—C=O, S, N or a covalent bond, to form an ester linkage, an anhydride linkage, a thioester linkage, an amide linkage or an azo linkage; and R is a hydrogen sulfide releasing moiety selected from the group consisting of:

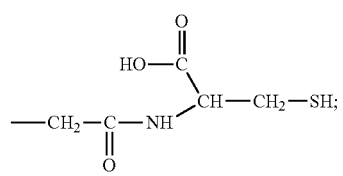

-continued

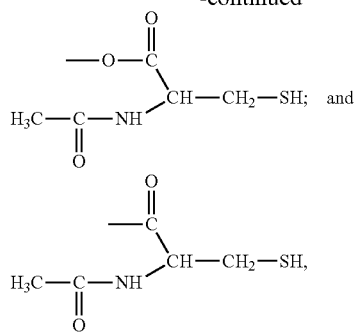

or a pharmacologically acceptable salt thereof.

2. The method according to claim 1 wherein the compound is 4- or 5- amino-2-hydroxy-benzoic acid anhydride with N-acetyl cysteine, or a pharmacologically acceptable salt thereof.

3. The method according to claim 1 wherein the inflammatory condition of the gastrointestinal tract is Crohn's disease.

4. The method according to claim 1 wherein the inflammatory condition of the gastrointestinal tract is ulcerative colitis.

5. The method according to claim 1 wherein the inflammatory condition of the gastrointestinal tract is irritable bowel syndrome.

* * * * *